United States Patent [19]

Blankley et al.

[11] Patent Number: 5,733,914
[45] Date of Patent: Mar. 31, 1998

[54] PYRIDO[2, 3-D]PYRIMIDINES FOR INHIBITING PROTEIN TYROSINE KINASE MEDIATED CELLULAR PROLIFERATION

[75] Inventors: Clifton John Blankley, Ann Arbor; Diane Harris Boschelli, Plymouth; Annette Marian Doherty, Ann Arbor; James Marino Hamby, Ann Arbor; Sylvester Klutchko, Ann Arbor; Robert Lee Panek, Canton, all of Mich.

[73] Assignee: Warner-Lambert Company, Morris Plains, N.J.

[21] Appl. No.: 611,279

[22] Filed: Apr. 3, 1996

Related U.S. Application Data

[63] Continuation-in-part of Ser. No. 433,294, May 3, 1995, Pat. No. 5,620,981.
[51] Int. Cl.$^6$ .................... A61K 31/505; C07D 487/02
[52] U.S. Cl. ............................... 514/258; 544/279
[58] Field of Search ..................... 544/279; 514/258

[56] References Cited

U.S. PATENT DOCUMENTS

| | | | |
|---|---|---|---|
| 3,534,039 | 10/1970 | Davoll | 260/256.4 |
| 3,639,401 | 2/1972 | Meyer | 260/256.4 |
| 4,271,164 | 6/1981 | Blankley et al. | 424/251 |
| 5,364,860 | 11/1994 | Bru-Magniez et al. | 514/300 |
| 5,409,930 | 4/1995 | Spada et al. | 514/248 |
| 5,620,981 | 4/1997 | Blankley et al. | 514/258 |

FOREIGN PATENT DOCUMENTS

| | | |
|---|---|---|
| 0537463 | 4/1993 | European Pat. Off. . |
| 9500513 | 5/1995 | WIPO . |
| 96/15128 | 5/1996 | WIPO . |

OTHER PUBLICATIONS

Proc. Natl. Acad. Sci., USA, vol. 88, May 1991, Lindner et al., Cell Biology, pp. 3739–3743.
Circulation Research, vol. 73, No. 3, Sep. 1993, Lindner et al., pp. 589–595.
Proc. Natl. Acad. Sci., USA, vol. 92, Mar. 1995, Buchdunger et al., pp. 2558–2562.
Bilder, et al., Drug Development Research, 29:158–166 (1993).
Oddie, et al., Journal of Neuroscience Research, 24:38–48 (1989).
Ely, et al., Journal of Neurochemistry, 62:P923–933 (1994).
Lynch, et al., Leukemia, vol. 7, No. 9, 1416–1422 (1993).
Luttrell, et al., Proc. Natl. Acad. Sci. USA, 91:83–87 (1994).
Pahlman, et al., Am. Rev. Respir. Dis., 142:S54–S56 (1990).
Mazurenko, et al., Eur. J. Cancer, vol. 28, No. 2/3, 372–377 (1992).
Fanning, et al., Cancer Research, 52:1457–1462 (1992).
Ottenhoff–Kalff, et al., Cancer Research, 52:4773–4778 (1992).
Cartwright, et al., Proc. Natl. Acad. Sci. USA, 87:558–562 (1990).
Talamonti, et al., J. Clin. Invest., 91:53–60 (1993).
Termuhlen, et al., Journal of Surgical Research, 54:293–298 (1993).
Novotny–Smith, et al., Journal of Immunotherapy, 11:159–168 (1992).
Muthuswamy, et al., Molecular and Cellular Biology, vol. 14, No. 1, 735–743 (1994).
Twamley–Stein, et al., Proc. Natl. Acad. Sci. USA, 90:7696–7700 (1993).
Guy, et al., Genes & Development, 8:23–32 (1994).
Loganzo, Jr. et al., Oncogene, 8:2637–2644 (1993).
Buchdunger, et al., Proc. Natl. Acad. Sci. USA, 92:2558–2562 (1995).
Blankley et al., J. Med. Chem., 26(3):403–411 (1983).
Bennett, et al., Chem. Abstracts, 24(4):382–389 (1981).
Davoll, et al., Chem. Abstracts, vol. 72, No. 72:66,973 (1970) Eq. of GB 1,171,218 and US 3,534,039.
Science, vol. 253, Apr. 1991, Ferns et al., pp. 1129–1132.
J. Clin. Invest., vol. 89, Feb. 1992, Jawein et al., pp. 507–511.
Journal of Cell Biol., vol. 111, Nov. 1990, Majesky et al., pp. 2149–2158.

Primary Examiner—Matthew V. Grumbling
Attorney, Agent, or Firm—Charles W. Ashbrook

[57] ABSTRACT

6-Aryl pyrido[2,3-d]pyrimidine 7-imines, 7-ones, and 7-thiones are inhibitors of protein tyrosine kinases, and are thus useful in treating cellular proliferation mediated thereby. The compounds are especially useful in treating cancer, atherosclerosis, restenosis, and psoriasis.

31 Claims, No Drawings

PYRIDO[2,3-D]PYRIMIDINES FOR INHIBITING PROTEIN TYROSINE KINASE MEDIATED CELLULAR PROLIFERATION

This is a continuation-in-part of U.S. application Ser. No. 08/433,294 filed May 3, 1995.

FIELD OF THE INVENTION

This invention relates to inhibition of protein tyrosine kinase (PTK) mediated cellular proliferation. More specifically, this invention relates to pyrido-[2,3-d] pyrimidines and their use in inhibiting cellular proliferation and protein tyrosine kinase enzymatic activity.

BACKGROUND OF THE INVENTION

Many disease states are characterized by the uncontrolled proliferation and differentiation of cells. These disease states encompass a variety of cell types and maladies such as, cancer, atherosclerosis, and restenosis. Growth factor stimulation, autophosphorylation, and the phosphorylation of intracellular protein substrates are important biological events in the pathomechanisms of proliferative diseases.

In normal cells, the phosphorylation of tyrosine residues on protein substrates serves a critical function in intracellular growth signaling pathways initiated by stimulated extracellular growth factor receptors. For example, the association of growth factors such as Platelet Derived Growth Factor (PDGF), Fibroblast Growth Factor (FGF), and Epidermal Growth Factor (EGF) with their respective extracellular receptors activates intracellular tyrosine kinase enzyme domains of these receptors, thereby catalyzing the phosphorylation of either intracellular substrates or the receptors themselves. The phosphorylation of growth factor receptors in response to ligand binding is known as autophosphoryllationo For example, the EGF receptor has as its two most important ligands EGF and Transforming Growth Factor α, (TGFα). The receptors appear to have only minor functions in normal adult humans, but are implicated in the disease processes of a large portion of all cancers, especially colon and breast cancer. The closely related Erb-B2 and Erb-B3 receptors have a family of Heregulins as their major ligands, and receptor overexpression and mutation have been unequivocally demonstrated as the major risk factor in poor prognosis breast cancer. The proliferation and directed migration of vascular smooth muscle cells (VSMC) are important components in such processes as vascular remodeling, restenosis and atherosclerosis. Platelet-derived growth factor has been identified as one of the most potent endogenous VSMC mitogens and chemoattractants. Elevated vascular mRNA expression of PDGF-A and -B chains and PDGF receptors has been observed in balloon-injured rat carotid arteries (*J. Cell. Biol.*, 111: 2149–2158 (1990)). In this injury model, infusion of PDGF also greatly increases intimal thickening and migration of VSMC (*J. Clin. Invest.*, 89: 507–511 (1992)). Furthermore, PDGF-neutralizing antibodies significantly reduce intimal thickening following balloon injury (*Science*, 253: 1129–1132 (1991)). Tyrphostin receptor tyrosine kinase inhibitors which block the PDGF signal transduction pathway have been shown to inhibit PDGF stimulated receptor tyrosine kinase phosphorylation in vivo in the rat cuff injury model (*Drug Develop. Res.*, 29: 158–166 (1993)).

Both acidic fibroblast growth factor (aFGF) and basic fibroblast growth factor (bFGF) have many biological activities, including the ability to promote cellular proliferation and differentiation. Direct evidence in support of FGF involvement in VSMC has been reported by Lindner and Reidy (*Proc. Natl. Acad. Sci. USA*, 88: 3739–3743 (1991)), who demonstrated that the systemic injection of a neutralizing antibody against bFGF prior to balloon angioplasty of rat carotid arteries inhibited injury-induced medial SMC proliferation by greater than 80% when measured 2 days after injury. It is likely that bFGF released from damaged cells is acting in a paracrine manner to induce VSMC growth. Recently, Lindner and Reidy (*Cir. Res.*, 73: 589–595 (1993)) demonstrated an increased expression of both mRNA for bFGF and FGFR-1 in replicating VSMCs and endothelium in en face preparations of balloon-injured rat carotid arteries. The data provides evidence that in injured arteries the ligand/receptor system of bFGF and FGFR-1 may be involved in the continued proliferative response of VSMCs leading to neointima formation.

Buchdunger, et al., *Proc. Natl. Acad. Sci.*, Vol. 92, March 1995, 2558–2562, reported the inhibition of the PDGF signal transduction pathway both in vitro and in vivo by a PDGF receptor tyrosine protein kinase inhibitor. The compound showed antitumor activity in tumor models using astrocytoma cell lines.

Thus, EGF, PDGF, FGF, and other growth factors play pivotal roles in the pathomechanisms of cellular proliferative diseases such as cancer, atherosclerosis, and restenosis. Upon association with their respective receptors, these growth factors stimulate tyrosine kinase activity as one of the initial biochemical events leading to DNA synthesis and cell division. It thereby follows that compounds which inhibit protein tyrosine kinases associated with intracellular growth factor signal transduction pathways are useful agents for the treatment of cellular proliferative diseases. We have now discovered that certain pyrido[2,3-d]-pyrimidines inhibit protein tyrosine kinases, and are useful in treating and preventing atherosclerosis, restenosis, and cancer.

Several pyrido[2,3-d]pyrimidines are known. For example, U.S. Pat. No. 3,534,039 discloses a series of 2,7-diamino-6-arylpyrido[2,3-d]pyrimidine compounds as diuretic agents; U.S. Pat. No. 3,639,401 discloses a series of 6-aryl-2,7-bis[(trialkylsilyl)amino]-pyrido[2,3-d]pyrimidine compounds as diuretic agents; U.S. Pat. No. 4,271,164 discloses a series of 6-substituted-arylpyrido[2,3-d] pyrimidin-7-amines and derivatives as antihypertensive agents; European Published Application 0 537 463 A2 discloses a series of substituted-pyrido[2,3-d]pyrimidines useful as herbicides. None of the foregoing references teach the compounds of this invention or suggest such compounds are useful for treating atherosclerosis, restenosis, psoriasis, and cancer.

SUMMARY OF THE INVENTION

This invention provides new compounds characterized as pyrido[2,3-d]pyrimidines which are useful in inhibiting protein tyrosine kinases, and thus are effective in treating cellular proliferative diseases of atherosclerosis, restenosis, psoriasis, and cancer. The invention is more particularly directed to compounds defined by the Formula I

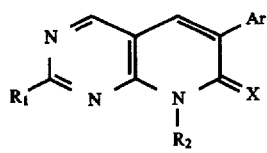

wherein

X is NH, N-Acyl, O, or S;

$R_1$ is $NR_3R_4$, $S(O)_{0,1}$ or $_2$-$R_3$, or $OR_3$;

$R_2$, $R_3$, and $R_4$ independently are hydrogen, $(CH_2)_nPh$, where Ph is phenyl or substituted phenyl and n is 0, 1, 2, or 3; heteroaromatic, cycloalkyl, $C_1$-$C_6$alkanoyl, $C_1$-$C_6$ alkyl, $C_2$-$C_6$ alkenyl, and C2-$C_6$alkynyl, where the alkyl, alkenyl, and alkynyl groups may be substituted by $NR_5R_6$, phenyl, substituted phenyl, thioalkyl, alkyloxy, hydroxy, carboxy, halogen, cycloalkyl, and where $R_5$ and $R_6$ are independently hydrogen, $C_1$-$C_6$ alkyl, $C_2$-$C_6$ alkenyl, $C_2$-$C_6$ alkynyl, $(CH_2)_nPh$ where Ph is phenyl or substituted phenyl and n is 0, 1, 2, or 3; cycloalkyl, heteroaromatic, and $R_5$ and $R_6$ taken together with the nitrogen to which they are attached can complete a ring having 3 to 7 carbon atoms and optionally containing 1, 2, or 3 heteroatoms selected from nitrogen, substituted nitrogen, oxygen, and sulfur;

$R_4$ can additionally be —C(=O)$R_3$, —C(=O)O$R_3$, —SO$_2$$R_3$, —SO$_2$NR$_5$R$_6$, —C(=O)NR$_5$R$_6$, —C(=S)NR$_5$R$_6$, —C(=NH)$R_3$, —C(=NH)NR$_5$R$_6$, and $R_3$ and $R_4$ can be taken together with the nitrogen to which they are attached to complete a ring having 3 to 7 carbon atoms and optionally containing 1, 2, or 3 heteroatoms selected from nitrogen, oxygen, and sulfur;

Ar is phenyl, substituted phenyl, or heteroaromatic; and the pharmaceutically acceptable salts thereof.

Preferred compounds have the above formula wherein Ar is phenyl or phenyl substituted with 1 or 2 groups selected from $C_1$-$C_6$ alkyl and halo, especially halo such as chloro or bromo.

Further preferred compounds are those wherein $R_2$ is $C_1$-$C_6$ alkyl, $C_2$-$C_6$ alkenyl, $(CH_2)_nPh$ such as phenyl and benzyl, or $C_3$-$C_6$ cycloalkyl such as cyclopropyl.

An especially preferred group of compounds have the above formula wherein X is O.

Another preferred group of compounds are those wherein X is NH. These are the imines, and are especially useful as intermediates leading to compounds where X is O.

Further preferred compounds have the above formula wherein $R_1$ is $NH_2$ or $NHR_3$, where $R_3$ is $C_1$-$C_6$ alkyl optionally substituted with $NR_5R_6$.

An especially preferred group of invention compounds have the formula

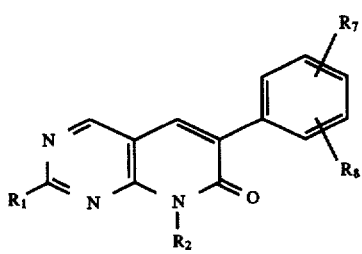

wherein $R_1$ is $NR_3R_4$, $OR_3$ or $SR_3$, where $R_3$ is hydrogen or $C_1$-$C_6$ alkyl, and $R_4$ is hydrogen or $C_1$-$C_6$ alkanoyl; $R_2$ is $C_1$-$C_6$ alkyl, and $R_7$ and $R_8$ independently are $C_1$-$C_6$ alkyl or halo, especially chloro, fluoro, or bromo. Preferred alkyl groups are substituted with $NR_5R_6$, where $R_5$ and $R_6$ are hydrogen or alkyl, or together with the nitrogen to which they are attached complete a cyclic ring having 2 heteroatoms, for example

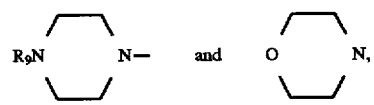

where $R_9$ is hydrogen, $C_1$-$C_6$ alkyl or $(CH_2)_nPh$.

Another preferred group of compounds have the formula

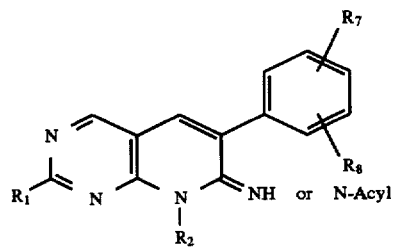

where $R_1$, $R_2$, $R_7$, and $R_8$ are as defined above.

Another preferred group of compounds have the formula

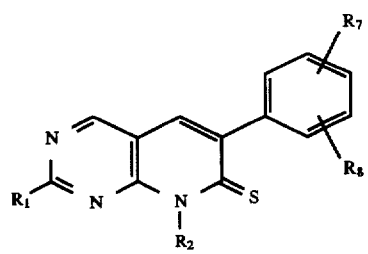

where $R_1$, $R_2$, $R_7$, and $R_8$ are as defined above.

It should be appreciated that when $R_2$ is hydrogen, the compounds can exist in tautomeric form as follows

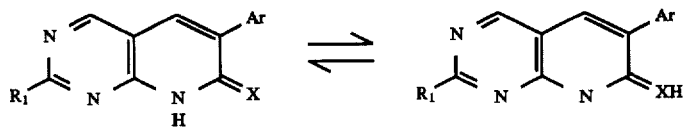

The most preferred compounds of the invention have the formula

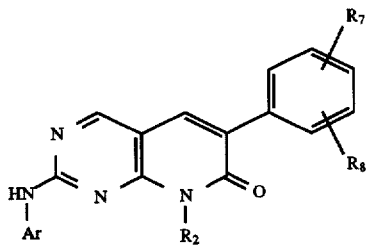

where $R_2$, $R_7$, $R_8$, and Ar are as defined above. Ideally, $R_2$ is alkyl such as methyl or ethyl, and $R_7$ and $R_8$ are halo such as chloro or bromo. The most preferred Ar group is phenyl, ideally phenyl substituted with one, two, or three groups selected from halo, $C_1$–$C_6$ alkyl, hydroxy, $C_1$–$C_6$ alkoxy, carboxy, $C_1$–$C_6$ alkoxycarbonyl, and $C_1$–$C_6$ alkyl substituted with hydroxy, carboxy, alkoxycarbonyl, amino, $C_1$–$C_6$ alkylamino, and di-$C_1$–$C_6$ alkylamino. An especially preferred group of such compounds have the formula

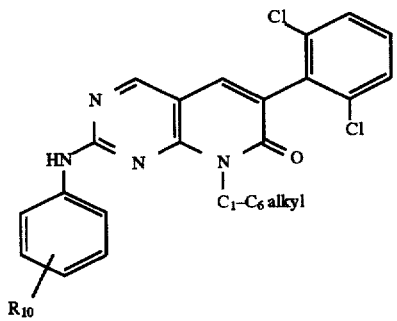

where $R_{10}$ is phenyl, chloro, bromo, methyl, methoxy, hydroxy, hydroxymethyl, 2-diethylaminoethoxy, methoxycarbonylmethyl, carboxy, carboxymethyl, ethoxycarbonyl, 2-carboxyethyl, or 2-ethoxycarbonylethyl.

This invention also provides pharmaceutical formulations comprising a compound of Formula I together with a pharmaceutically acceptable carrier, diluent, or excipient therefor.

Compounds within the scope of the present invention have a specific affinity towards one or more of the substrate sites of the tyrosine kinase domains of EGF, and other EGF family of receptors such as erb B2, 3, and 4; FGFs, PDGF, V-src and C-src. Compounds within the scope of the present invention have effectively inhibited PDGF autophosphorylation of the receptor and inhibited vascular smooth muscle cell proliferation and migration.

As inhibitors of protein kinases, the compounds of the instant invention are useful in controlling proliferative disorders including leukemia, cancer, psoriasis, vascular smooth muscle proliferation associated with atherosclerosis, and postsurgical vascular stenosis and restenosis in mammals.

A further embodiment of this invention is a method of treating subjects suffering from diseases caused by vascular smooth muscle proliferation. The method entails inhibiting vascular smooth muscle proliferation and/or migration by administering an effective amount of a compound of Formula I to a subject in need of treatment.

DETAILED DESCRIPTION OF THE INVENTION

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

In the compounds of Formula I, the term "$C_1$–$C_6$ alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

"Halo" includes fluoro, chloro, bromo, and iodo.

"$C_2$–$C_6$ Alkenyl" means straight and branched hydrocarbon radicals having from 2 to 6 carbon atoms and 1 double bond and includes ethenyl, 3-buten-1-yl, 2-ethenylbutyl, 3-hexen-1-yl, and the like. Typical $C_2$–$C_6$ alkynyl groups include propynyl, 2-butyn-1-yl, 3-pentyn-1-yl, and the like.

"$C_3$–$C_6$ Cycloalkyl" means a cyclic hydrocarbyl group such as cyclopropyl, cyclobutyl, cyclohexyl, and cyclopentyl.

"$C_1$–$C_6$ Alkoxy" refers to the alkyl groups mentioned above binded through oxygen, examples of which include methoxy, ethoxy, isopropoxy, tert-butoxy, and the like.

"$C_1$–$C_6$ Alkanoyl" groups are alkyl linked through a carbonyl, i.e.,

Such groups include formyl, acetyl, propionyl, butyryl, and isobutyryl.

"Acyl" means an alkyl or aryl (Ar) group bonded through a carbonyl group

For example, acyl includes a $C_1$–$C_6$ alkanoyl, including substituted alkanoyl, wherein the alkyl portion can be substituted by $NR_5R_6$ or a carboxylic or heterocyclic group. Typical acyl groups include acetyl, benzoyl, and the like.

The alkyl, alkenyl, alkoxy, and alkynyl groups described above may be substituted. The substituent groups which may be part of the alkyl, alkenyl, alkoxy, and alkynyl groups are $NR_5R_6$, phenyl, substituted phenyl, thioalkyl ($C_1$–$C_6$), $C_1$–$C_6$ alkoxy, hydroxy, carboxy, $C_1$–$C_6$ alkoxycarbonyl, halo, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_n$Ph.

Examples of substituted alkyl groups thus include 2-aminoethyl, 2-diethylaminoethyl, 2-dimethylaminopropyl, ethoxycarbonylmethyl, 3-phenylbutyl, methylsulfanylmethyl, methoxymethyl, 3-hydroxypentyl, 2-carboxybutyl, 4-chlorobutyl, 3-cyclopropylpropyl, 3-morpholinopropyl, piperazinylmethyl, and 2-(4-methylpiperazinyl) ethyl.

Examples of substituted alkenyl groups thus include 2-diethylaminoethenyl, 3-amino-2-butenyl, 3-(1-piperazinyl)-1-propenyl, 3-hydroxy-1-propenyl, 2-(1-s-triazinyl)ethenyl, 3-phenyl-3-pentenyl, and the like.

Examples of substituted alkynyl groups include 2-methoxyethynyl, 2-ethylsulfanyethynyl, 4-(1-piperazinyl) -3-(butynyl), 3-phenyl-5-hexynyl, 3-diethylamino-3-butynyl, 4-chloro-3-butynyl, 4-cyclobutyl-4-hexynyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxyhexyloxy, and the like.

Further, examples of substituted alkyl, alkenyl, and alkynyl groups include dimethylaminomethyl, carboxymethyl, 4-diethylamino-3-buten-1-yl, 5-ethylmethylamino-3-pentyn-1-yl, 4-morpholinobutyl, 4-tetrahydropyridinylbutyl-3-imidazolidin-1-ylpropyl, 4-tetrahydrothiazol-3-yl-butyl, phenylmethyl, 3-chlorophenylmethyl, and the like.

The term "Ar" refers to unsubstituted and substituted aromatic and heteroaromatic groups. Heteroaromatic groups have from 4 to 9 ring atoms, from one to four of which are selected from O, S, and N. Preferred groups have 1 or 2 heteroatoms in a 5- or 6-membered aromatic ring. Mono and bicyclic ring systems are included. Typical Ar groups include phenyl, 3-chlorophenyl, 2,6-dibromophenyl, pyridyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, and the like.

Preferred Ar groups are phenyl and phenyl substituted by 1, 2, or 3 groups independently selected from halo, alkyl, alkoxy, thio, thioalkyl, hydroxy, alkanoyl, —CN, —NO$_2$, —COOR$_8$, —CF$_3$, alkanoyloxy, or amino of the formula —NR$_5$R$_6$. The alkyl and alkoxy groups can be substituted as defined above. For example, typical groups are carboxyalkyl, i.e.,

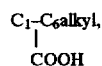

alkoxycarbonylalkyl

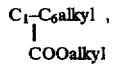

hydroxyalkyl and hydroxyalkoxy,

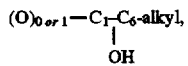

and alkoxyalkyl, i.e.,

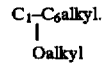

Disubstituted phenyl is most preferred, and 2,6-disubstituted phenyl is especially preferred.

Typical Ar substituted phenyl groups which are preferred thus include 2-aminophenyl, 3-chloro-4-methoxyphenyl, 2,6-dimethylphenyl, 2,6-diethylphenyl, 2-n-hexyl-3-fluorophenyl, 3-hydroxyphenyl, 4-hydroxymethylphenyl, 3,4-dimethoxyphenyl, 2,6-dichlorophenyl, 4-(3-aminopropoxy)phenyl-, 2,6-difluorophenyl, 2-chloro-6-methylphenyl, 2,4,6-trichlorophenyl, 2,6-dimethoxyphenyl, 4-(diethylaminoethoxy)phenyl, 2,6-dihydroxyphenyl, 2,6-dibromophenyl, 2,6-dinitrophenyl, 2,6-di-(trifluoromethyl) phenyl, 3-(dimethylaminoethyl)phenyl, 2,6-dimethylphenyl, 2,3,6-trimethylphenyl, 2,6-dibromo-4-methylphenyl, and the like.

In a preferred embodiment, R$_1$ in Formula I is a group NR$_3$R$_4$, where R$_3$ and R$_4$ independently are hydrogen, C$_1$–C$_6$-alkyl, C$_1$–C$_6$-alkyl substituted with the group NR$_5$R$_6$, and where R$_3$ is hydrogen and R$_4$ is C$_1$–C$_5$-alkanoyl or alkanoyl substituted with COOH. Examples of such NR$_3$R$_4$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. R$_3$ and R$_4$ can be taken together with the nitrogen to which they are attached to complete a ring, which may contain 2 or more heteroatoms, preferably nitrogen. Examples of such cyclic NR$_3$R$_4$ groups include pyrrolidinyl, piperazinyl, 4-methylpiperazinyl, 4-benzylpiperazinyl, pyridinyl, piperidinyl, pyrazinyl, morpholinyl, and the like. R$_3$ and R$_4$ can additionally complete a cyclic ring which is substituted with 1 or 2 oxo groups. For example, when R$_3$ is hydrogen and R$_4$ is alkanoyl (i.e.,

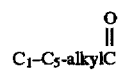

in which the alkyl bears a substituent such as carboxy or halo, such groups can be cyclized to form cyclic ketones. Typical groups include 2-keto-pyrrolidinyl and 1-pyrrolidinyl-2,5-dione. As noted above, a preferred group of compounds are those wherein R$_3$ is hydrogen and R$_4$ is aryl, especially phenyl and phenyl substituted with groups such as aminoalkyl and aminoalkoxy, e.g., dimethylaminoethyl and dimethylaminoethoxy.

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 66: 1–19 (1977)).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'- dibenzylethylenediamine, chloroprocaine, choline, diethanolamine, ethylenediamine, N-methylglucamine, and procaine (see, for example, Berge S. M., et al., "Pharmaceutical Salts," *J. of Pharmaceutical Science*, 66: 1–19 (1977)).

The base addition salts of acidic compounds (for example when $R_3$ is a carboxy alkyl group such as carboxymethyl or 3-carboxybutyl) are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

Compounds of Formula I may be prepared according to the syntheses outlined in Schemes I–VII. Although these schemes often indicate exact structures, the methods apply widely to analogous compounds of Formula I, given appropriate consideration to protection and deprotection of reactive functional groups by methods standard to the art of organic chemistry. For example, hydroxy groups, in order to prevent unwanted side reactions, generally need to be converted to ethers or esters during chemical reactions at other sites in the molecule. The hydroxy protecting group is readily removed to provide the free hydroxy group. Amino groups and carboxylic acid groups are similarly derivatized to protect them against unwanted side reactions. Typical protecting groups, and methods for attaching and cleaving them, are described fully by Greene and Wuts in *Protective Groups in Organic Synthesis*, John Wiley and Sons, New York, (2nd Ed; 1991), and McOmie, *Protective Groups in Organic Chemistry*, Plenum Press, New York, 1973.

Scheme I describes a typical method for preparing the pyrido[2,3-d]pyrimidin-7(8H)-ones and the 7-(8H)-imides of the invention, compounds of Formula I wherein X is O or NH. The synthesis starts by reacting a cyanoacetate such as ethyl ethoxymethylenecyanoacetate with a thiopseudourea such as 2-methyl-2-thiopseudourea sulfate to provide 5-cyano-4-hydroxy-2-(methylsulfanyl)pyrimidine. This reaction is described more fully in *Helv. Chim. Acta.*, 42: 763–772 (1959). The 4-hydroxypyrimidine is next reacted with a halogenating agent such as phosphorous oxychloride or thionyl chloride to provide a 4-halo pyrimidine, for example, 5-cyano-4-chloro-2-(methylsulfanyl)pyrimidine. The halopyrimidine next is reacted with an amine $R_2NH_2$ to provide a 5-cyano-4-substituted amino-2-(methylsulfanyl) pyrimidine. The amine utilized can have $R_2$ be the group desired in the final product of Formula I, for example, alkyl such as methyl, or $R_2$ can be a group that can be later removed, for example, benzyl or the like, to generate Formula I compounds wherein $R_2$ is hydrogen. Compounds where $R_2$ is hydrogen can be alkylated and acylated by standard methods.

The reaction between the halopyrimidine and the amine $R_2NH_2$ typically is carried out by mixing equimolar quantities of the halopyrimidine and amine in an unreactive organic solvent such as toluene, xylene, methylene chloride, or the like, at a temperature of about 50° C. to about 150° C. Excess amine can be utilized if desired. The 4-aminopyrimidine that is produced is next reacted with hydrazine or a substituted hydrazine to displace the 2-methylsulfanyl group to provide a 2-hydrazino-4-substituted amino-5-cyano-pyrimidine. The hydrazinopyrimidine is reacted with sodium nitrite in aqueous mineral acid to effect diazotization of the hydrazine group to provide a 2-azido-4-(substituted amino)-5-cyano-pyrimidine. Reaction of this compound with a reducing agent such as Raney Nickel effects hydrogenation of both the cyano group and the azido group to produce a 2-amino-4-(substituted amino) -5-pyrimidinecarboxaldehyde.

The 4-(substituted amino)-5-pyrimidine carboxaldehydes can alternatively be prepared by starting with a commercially available 4-halo-5-pyrimidinecarboxylic acid ester. For example, 2-methylsulfanyl-4-chloro-5-pyrimidinecarboxylic acid ethyl ester (available from Aldrich Co.) can be reacted with an amine $R_2NH_2$, such as methylamine, benzylamine, or the like, to displace the 4-chloro group and provide the corresponding 2-methylsulfanyl-4-(substituted amino)-5-pyrimidinecarboxylic acid ethyl ester. The ester group is reduced to an alcohol, for instance by reaction with lithium aluminum hydride in tetrahydrofuran, and the alcohol group is then oxidized to an aldehyde by reaction with an oxidant such as sodium dichromate, manganese II oxide, or the like, to give the corresponding 2-methylsulfanyl-4-(substituted amino)-5-pyrimidinecarboxaldehyde. The 2-methyl sulfanyl group is displaced with hydrazine, and the hydrazino group is diazotized and subsequently reduced as described above to provide the desired 2-amino-4-(substituted amino)-5-pyrimidinecarboxaldehyde.

The pyrimidinecarboxaldehyde is next reacted with an arylacetonitrile in the presence of a base and in a solvent such as xylene, 2-ethoxyethanol, dioxane, or the like, as shown in Scheme I. Typical bases that can be utilized include sodium hydride, sodium methoxide, sodium metal, potassium carbonate, and the like. The pyrimidine carboxaldehyde and arylacetonitrile are typically utilized in approximately equimolar quantities. Typical arylacetonitriles which can be employed include phenylacetonitrile, 2,6-dichlorophenylacetonitrile, 2,6-dimethylphenylacetonitrile, o-tolylacetontrile, pyridylacetonitrile, furanylacetonitrile, naphthylacetonitrile, and the like. The reaction typically is carried out in an unreactive solvent such as methyl or ethyl cellosolve, diglyme, dimethylformamide, or the like, and at an elevated temperature of about 50° C. to about 200° C., and generally is substantially complete within about 2 to about 24 hours. The product, a 6-aryl-7-imino-8-substituted-7,8-dihydropyrido[2,3-d]pyrimidin-2-ylamine of Formula I, wherein X is NH, and $R_1$ is $NR_3R_4$, is readily isolated by adding water to the reaction mixture, which generally causes precipitation of the product. The product imine can be further purified if needed by recrystallization from solvents such as ethyl acetate, acetone, isopropanol, and the like, or by chromatography over solid supports such as silica gel.

The 6-aryl-7-imino-8-substituted-7,8-dihydropyrido[2,3-d]pyrimidin-2-ylamine thus prepared has the formula

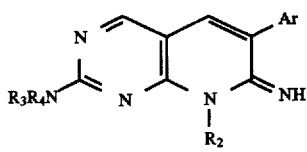

wherein $R_2$, $R_3$, $R_4$, and Ar are as defined above. Typical imines thus provided include the following:

| $R_2$ | $R_3$ | $R_4$ | Ar |
|---|---|---|---|
| $CH_3$ | H | $CH_3$ | phenyl |
| cyclopropyl | $CH_3$ | $CH_3$ | 3-methoxyphenyl |
| 3-butynyl | Et | acetyl | 1-naphthyl |
| 3-chlorophenyl | H | H | 3-pyridyl |
| 3-aminopropyl | H | 2-furyl | 2-thienyl |
| benzyl | $-CH_2-CH_2-CH_2-CH_2$ | | 2,3,5-tribromophenyl.HCl |
| Et | Et | Et | phenyl |
| Et | H | $-CH_2CH_2-N\underset{\phantom{x}}{\diagup\!\!\!\!\diagdown}N-CH_3$ | phenyl |
| Et | H | phenyl ring | 2-iodophenyl |
| Me | H | phenyl ring with $OCH_2CH_2N(CH_3)_2$ | 2,6-dibromophenyl |

The 6-aryl-7-imino-8-substituted-7,8-dihydropyrido[2,3-d]pyrimidine-2-ylamines are useful therapeutic agents, as well as intermediates since they are readily converted to the corresponding 7-keto derivative by simply heating in a mineral acid such as hydrochloric acid, sulfuric acid, phosphoric acid, or the like. The hydrolysis generally is substantially complete after about 5 to about 24 hours when carried out at about 60° C. to about 200° C. The product, a 2-amino-6-aryl-8-substituted-pyrido[2,3-d]pyrimidin-7(8H)-one, is readily isolated by removal of the reaction solvent, for example by evaporation under reduced pressure, and crystallization from common solvents such as ethyl acetate, acetone, tetrahydrofuran, and the like.

The 7-oxo-pyrido[2,3-d]pyrimidines of the invention can alternatively be prepared by simply hydrolyzing a 7-aminopyridopyrimidine in a mineral acid, as illustrated in Scheme II. The 7-amino-pyridopyrimidines are readily available by the methods described in U.S. Pat. No. 3,534,039. The 7-amino-pyridopyrimidine is simply dissolved in a mineral acid such as concentrated hydrochloric acid, sulfuric acid, phosphoric acid, or the like. The hydrolysis reaction generally is complete after about 12 to about 24 hours when carried out at about 80° C. to about 200° C. The product is readily isolated by removal of the reaction solvent and crystallization from a solvent such as dimethylsulfoxide, dimethylformamide, dioxane, or the like.

The 7-oxo-pyrido[2,3-d]pyrimidines can alternatively be prepared by reacting a 2,4-diamino-5-pyrimidinecarboxaldehyde with an aryl acetoester as shown below:

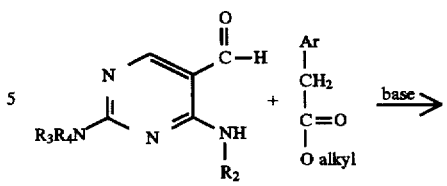

-continued

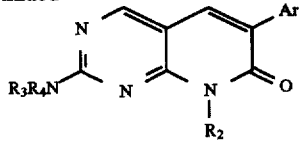

where $R_2$, $R_3$, $R_4$, and Ar are as defined above, and alkyl is a lower alkyl group such as methyl, ethyl, isobutyl, and the like. The reactants generally are mixed together in an unreactive solvent such as dimethylformamide, tetrahydrofuran, or ethyl cellosolve, and the aryl acetoester generally is utilized in excess, for instance in a 0.5 to 1.0 molar excess relative to the pyrimidine. The reaction is carried out in the presence of a base such as sodium methoxide or sodium hydride, and generally is complete within about 2 to about 24 hours when carried out at an elevated temperature of about 50° to about 120° C. The product 7-oxo-pyrido[2,3-d]pyrimidines are recovered by removing the reaction solvents and crystalizing the product from an organic solvent such as methanol, ethyl acetate, or the like. The process can be carried out with 2-oxy ($R_1$=—$OR_3$) and 2-thio ($R_1$=—$SR_3$) 4-amino-5-pyrimidinecarboxaldehydes to provide the corresponding 7-oxo-2-oxy and 2-thio pyrido[2,3-d]-pyrimidines of the invention.

Invention compounds wherein $R_2$ in Formula I is other than hydrogen are readily prepared by utilizing a substituted amine $R_2NH_2$ in the reaction described above, or alternatively by alkylating a pyridopyrimidine wherein $R_2$ is hydrogen, for example as illustrated in Scheme II. The reaction generally is carried out by mixing the pyridopyrimidine with an equimolar quantity or excess of alkylating agent, for instance an alkyl halide such as methyl iodide, benzyl bromide, 3-hexen-1-yl iodide, or the like, in a mutual solvent such as toluene, xylene, dimethylformamide, or the like. A base such as sodium hydride can be added to catalyze the reaction and to act as an acid scavenger. The product, an 8-substituted pyridopyrimidine, is readily isolated by removal of the reaction solvents, and further purified if desired by chromatography or crystallization from toluene, acetone, or the like.

Scheme III illustrates the reaction of 2-amino-pyridopyrimidines with acylating agents and diacylating agents to form amides and cyclic amino systems. For example, a 2-amino-pyridopyrimidine of the formula

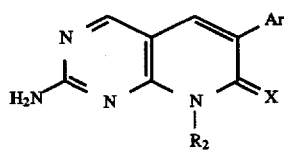

wherein $R_2$ is other than hydrogen, X is O or S, and Ar is as defined above, can be reacted with an equimolar quantity or slight excess of an acid halide or an acid anhydride to effect acylation of the 2-amino group. Typical acid halides include acetyl chloride, benzoyl bromide, propionyl iodide, and the like. Commonly used anhydrides include acetic anhydride, propionyl anhydride, and mixed anhydrides such as acetic butyric anhydride. Acylating agents such as succinic anhydride and the like can be utilized to form cyclic imides as described in Scheme III.

Invention compounds wherein X is S have the formula

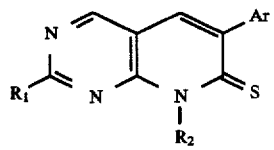

wherein $R_1$, $R_2$, and Ar are as defined above. These pyridopyrimidine thiones are prepared by reacting the corresponding 7-oxo compounds (i.e., where X=O) with an equivalent amount of Lawesson's Reagent or phosphorus pentasulfide in a solvent, preferably pyridine or toluene, at an elevated temperature of about 90° C. to about 125° C. for a period of about 1 to about 24 hours. The product is readily isolated by simply removing all reaction solvent, and further purification can be achieved, if desired, by routine methods such as crystallization, chromatography, and the like.

The 2-oxy, 2-thio, and 2-amino-pyridopyrimidines of the invention, compounds of the formula

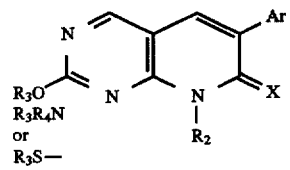

can alternatively be prepared as described in Schemes IV and V.

Scheme IV describes a method of synthesis of compounds having a basic side chain at the 2-position of the pyrido[2,3-d]pyrimidine ring system, for example, where $R_1$ is $NR_3R_4$ and $R_3$ is hydrogen or $C_1$–$C_6$alkyl substituted with $NR_5R_6$, and $R_4$ is hydrogen. In the first step, an aldehyde such as 4-methylamino-2-methylsulfanyl-pyrimidine-5-carbaldehyde is condensed with a arylacetonitrile derivative such as 2,6-dichlorophenylacetonitrile, in a mutual solvent such as N,N-dimethylformamide, and in the presence of a 1 to 5 molar excess of a base, preferably powdered potassium carbonate or cesium carbonate, at temperatures preferably in the range of 110° C. to 153° C. for a time period of 0.5 to 25 hours. The resulting 7-imino-2-methylsulfanyl derivatives are useful for preparing a variety of 2-amino derivatives. For example, treatment with a 100 to 500 percent molar excess of a primary amine such as N,N-diethylaminopropylamine, at temperatures in the range of 100° C. to 150° C. for about 1 to about 24 hours, gives the corresponding 2-substituted amino derivatives. In the case of amines that boil at less than about 100° C., e.g., methylamine, ethylamine, propylamine, and the like, an appropriate pressure bomb can be utilized to reach the desired reaction temperatures. The resulting 2-amino-7-imino derivatives are readily hydrolyzed, if desired, to the 2-amino-7-oxo derivatives by reaction with a strong mineral acid, such as concentrated hydrochloric acid or sulfuric acid, at reflux temperatures for prolonged periods of time, in the range of 6 hours to 7 days.

Alternatively, the 7-imino-2-methylsulfanyl derivatives can be acylated by reaction with an acyl halide or acyl anhydride, for example acetyl chloride or propionic anhydride, to provide the corresponding 7-acylimino-2-methylsulfanylpyridopyrimidines. These compounds can be reacted with an amine as described above to effect displacement of the 2-methylsulfanyl group and provide a 2-aminopyridopyrimidine having an acylimino group at the 7-position (i.e., X=N Acyl). The 7-acylimido derivatives can be reacted with a strong acid as described above to effect hydrolysis of the 7-acylimino group to a 7-oxo group.

The sulfanyl compounds of Formula I, i.e., where $R_1$ is $SR_3$, are readily oxidized to the corresponding sulfoxides and sulfones by reaction with agents such as m-chloroperbenzoic acid, hydrogen peroxide, sodium perborate, potassium hydrogen persulfate, and the like. As noted above, the sulfanyl, sulfinyl, and sulfonyl derivatives of Formula I are especially useful to make the corresponding amino derivatives, because they readily react with amines ($HNR_3R_4$) to undergo nucleophilic displacement. This is an especially preferred method for making the 2-arylamino and 2-heteroarylamino compounds of the invention (e.g., where $R_3$ is phenyl or pyridyl). The foregoing oxidation and nucleophilic displacement reactions are illustrated in Scheme VI.

The oxidation of a sulfanyl compound of Formula I is accomplished by reacting it with an equimolar quantity of an oxidant, preferably m-chloroperbenzoic acid, to produce the corresponding sulfoxide, or with a two molar equivalent to produce the corresponding sulfone. The oxidation typically is carried out in an organic solvent such as chloroform or dichloromethane, and typically is complete within 1 to 24 hours when carried out at 25° C. to 45° C. Larger quantities of oxidant and longer reaction times ensure complete formation of the sulfone. The corresponding sulfoxide or sulfone is readily isolated by filtration, or by removal of the reaction solvent by evaporation under reduced pressure.

Amines readily displace the sulfanyl, sulfinyl, and sulfonyl groups to produce compounds of Formula I where $R_1$ is $NR_3R_4$. This is an especially preferred method for making aryl amino compounds, i.e., phenylamino, substituted phenylamino, heteroarylamino (e.g., pyridylamino, thienylamino), and substituted heteroarylamino (e.g., ethylpyridylamino). The displacement is accomplished by mixing the sulfanyl, sulfinyl, or sulfonyl compound with an amine, preferably a primary or secondary amine. The amine generally is utilized in excess, for instance from about 20 to 500 molar excess relative to the sulfanyl, sulfinyl, or sulfonyl compound. The reactants generally are mixed neat or in a mutual organic solvent, for example dimethylformamide, (ethoxyethyl)ether, glacial acetic acid, dimethylsulfoxide, and the like. The reaction generally is complete after about 5 minutes to about 6 hours when carried out at an elevated temperature of about 100° C. to about 250° C. The product, a compound of Formula I, where $R_1$ is $NR_3R_4$, is readily isolated by filtration, or by removing the reaction solvent by evaporation. The product can be purified further, if desired, by crystallization, chromatography, or the like.

The 2-amino pyridopyrimidines of the invention (Formula I where $R_1$ is $NR_3R_4$) can alternatively be prepared by reacting a 2,4-diamino-5-pyrimidine-carboxaldehyde with an aryl acetonitrile ($ArCH_2CN$). The 2,4-diamino-5-pyrimidinecarboxaldehydes can be prepared from readily available 2-sulfanyl or sulfinyl pyrimidines by nucleophilic displacement with an amine as described above. For example, a 2-sulfanyl-4-substituted amino-5-alkoxycarbonylpyrimidine can be reacted with an oxidizing agent such as oxaziridine to give the corresponding sulfoxide or sulfone. The sulfoxide or sulfone substituent is readily displaced by reaction with an amine ($HNR_3R_4$), to provide the corresponding 2,4-diamino-5-alkoxycarbonylpyrimidine. The alkoxycarbonyl moiety can be converted to an aldehyde moiety by standard methods (i.e., reduction to an alcohol and oxidation of the alcohol to an aldehyde). The 2,4-diamino-5-pyrimidinecarboxaldehyde readily reacts with an arylacetonitrile to produce a 2-amino-6-aryl-pyridopyrimidine of the invention. The foregoing reactions are depicted in Scheme VII.

As noted above, some of the compounds of the invention are basic in nature, by virtue of a substituent group which is basic, such as amino groups for example. Compounds of Formula I wherein $R_1$ is $NR_3R_4$ are typically basic. Such basic compounds readily form pharmaceutically acceptable salts with any number of inorganic and organic acids. The salts typically are crystalline, and generally are water soluble and are thus well suited to oral administration and the like.

Scheme V describes the synthesis of 2-oxypyridopyrimidines. The 2-methylsulfanyl intermediates, such as described above, can be reacted with an alcoholate, such as ethoxyethanol sodium salt, which generally is generated with an equivalent amount of sodium hydride and an alcohol. The ethoxyethanol is typically employed as the reaction solvent. The reaction is best accomplished at elevated temperatures of about 100° C. to about 150° C., and normally is complete after about 15 minutes to 6 hours. The resulting 2-(2-ethoxy)-ethoxy ether is readily converted to the 2-hydroxy compound by reaction with a strong mineral acid, preferably 6N hydrochloric acid, for about 5 minutes to about 1 hour. The 2-hydroxy-7-imino derivative can be hydrolyzed to the 7-oxo compound by prolonged reaction with a strong mineral acid, preferably concentrated hydrochloric acid, at reflux temperatures for a period of 6 hours to 7 days. Alkylations and aralkylations of the 2-hydroxy derivative (preferably when $R_2$ is other than hydrogen) may be carried out as desired by reaction with an alkylating agent such as methyl iodide, benzyl bromide, diethylaminoethyl chloride, and the like, in a mutual solvent, preferably dimethylformamide, typically in the presence of base such as powdered potassium carbonate. Such reactions normally are complete within about 2 hours when carried out at temperatures of about 25° C. to 100° C. The product is readily isolated by removing the reaction solvents, and further purification can be accomplished by crystallization, chromatography, or the like.

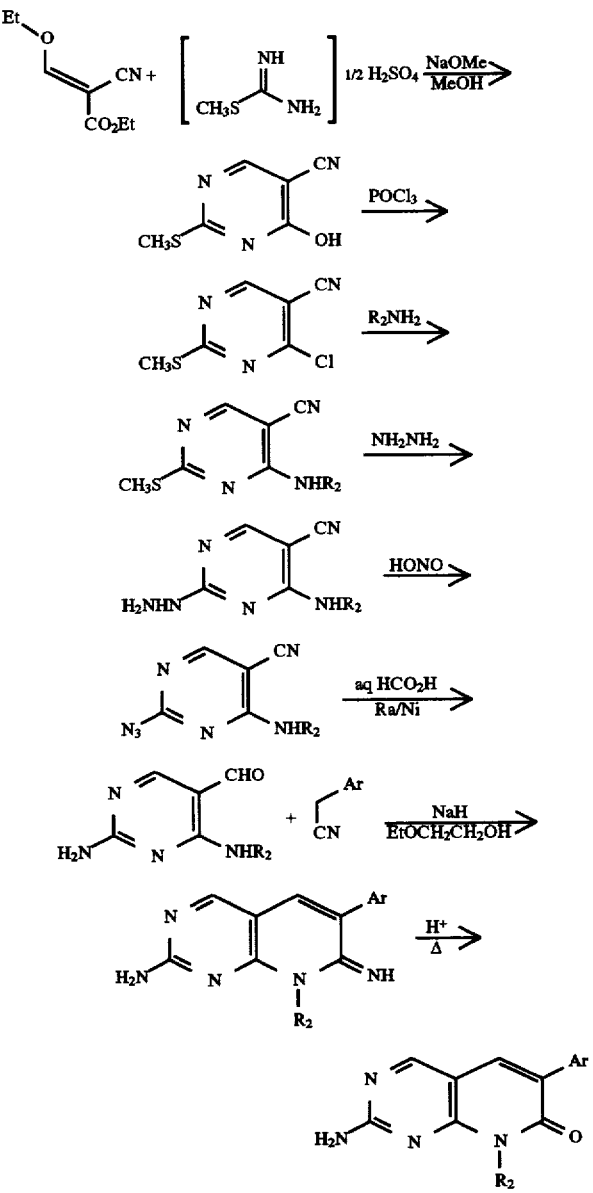

SCHEME I

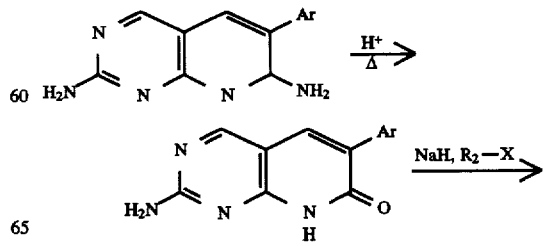

SCHEME II

17
-continued
SCHEME II
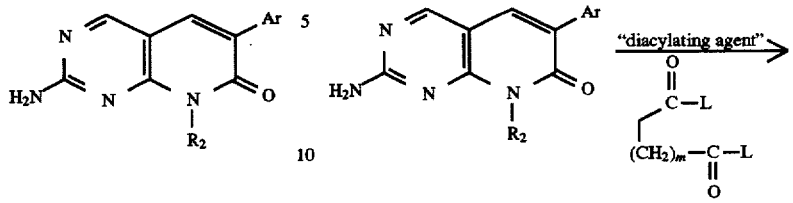
SCHEME III
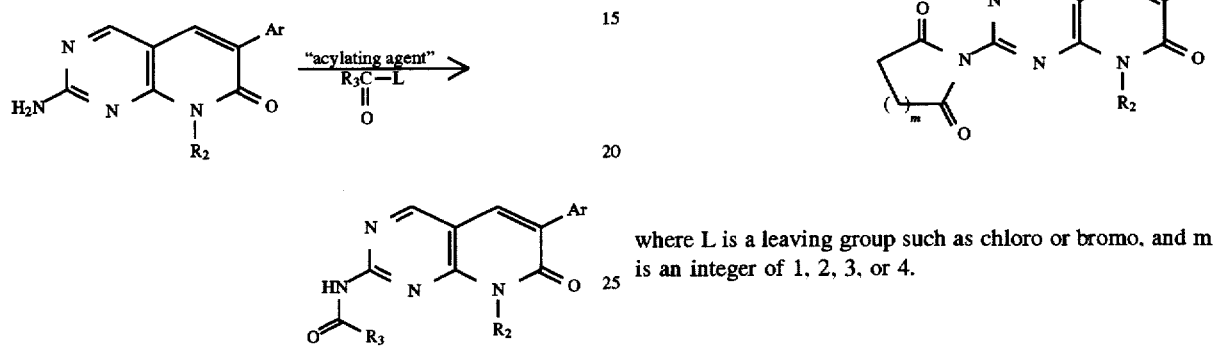
18
-continued
SCHEME III
where L is a leaving group such as chloro or bromo, and m is an integer of 1, 2, 3, or 4.
SCHEME IV
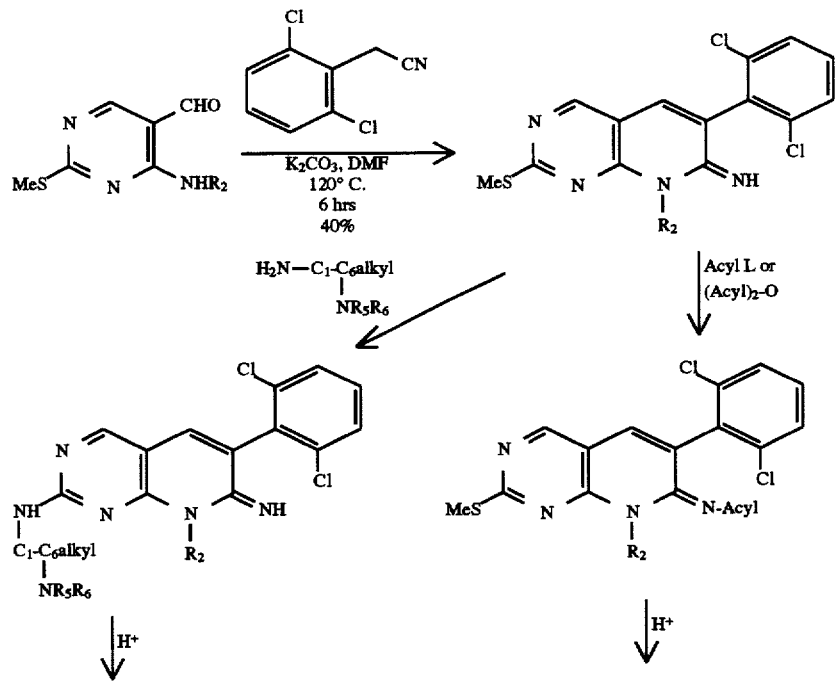

-continued
SCHEME IV
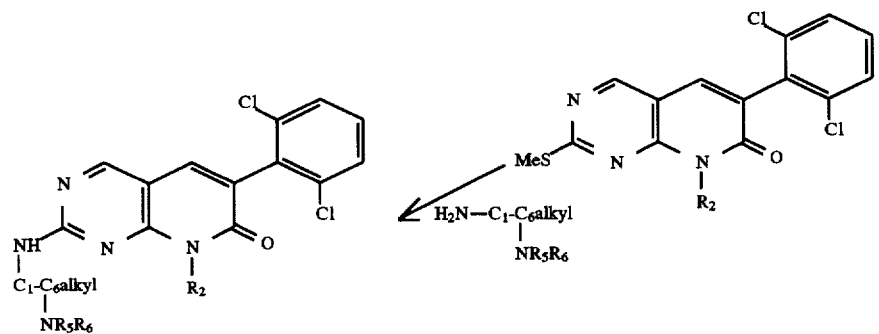
SCHEME V
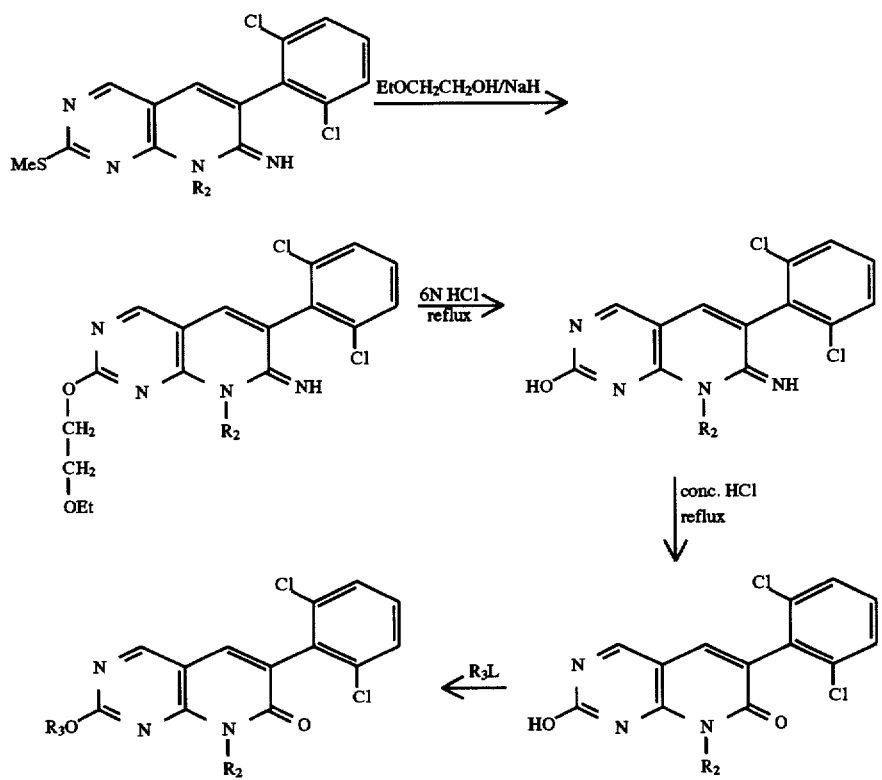
Scheme VI
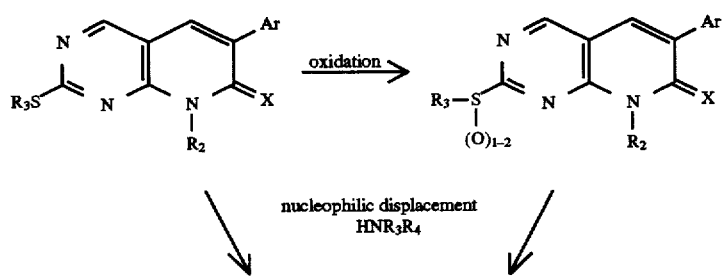

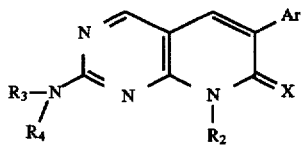

Scheme VII

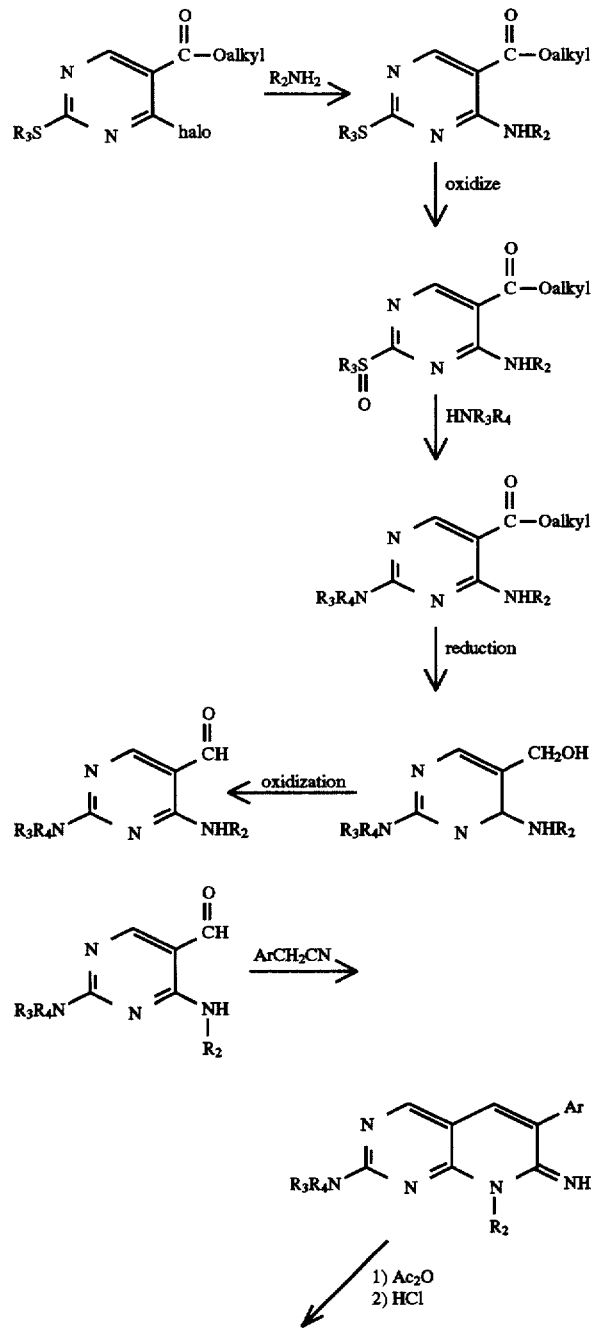

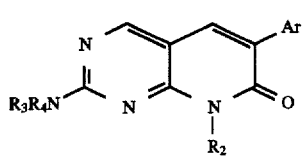

The following detailed examples further illustrate synthesis of the compounds of this invention. The examples are illustrative only, and are not to be construed as limiting the invention in any respect.

EXAMPLE 1

5-Cyano-4-hydroxy-2-(methylsulfanyl)-pyrimidine

To a solution of freshly distilled ethyl ethoxymethylene cyanoacetate (118.99 g) in methanol (800 mL) at 5° C. was added 2-methyl-2-thiopseudourea (107.69 g). To this mixture was added a solution of sodium methoxide in methanol prepared by dissolving sodium metal (35.59 g) in methanol (800 mL). The reaction was allowed to warm to room temperature and stirred for 6 hours. After standing overnight, the solvent was removed under reduced pressure, the residue was dissolved in 1500 mL of water at 50° C. with stirring, and the solution was filtered hot. The filtrate was acidified to pH 2 with concentrated HCl and allowed to stand overnight at room temperature. The product was collected by filtration and dried to give 48.33 g of 5-cyano-4-hydroxy-2-methylsulfanyl-pyrimidine. This product was used directly in the next step without further purification.

EXAMPLE 2

4-Chloro-5-cyano-2-methylsulfanyl-pyrimidine

A mixture of 5-cyano-4-hydroxy-2-methylsulfanylpyrimidine (48.33 g) from Example 1 and phosphorus oxychloride (150 mL) was heated at reflux for 3 hours. The reaction mixture was allowed to cool to room temperature, filtered, and the filtrate was concentrated to dryness under vacuum. The residue was partitioned between methylene chloride and ice water. The organic layer was separated, washed with water, dried over magnesium sulfate, filtered, and evaporated under reduced pressure. The residue was heated to reflux in hexane (750 mL) with stirring. The hot hexane solution was decanted from the insoluble material and allowed to cool to room temperature to afford 32 g of the title compound 4-chloro-5-cyano-2-methylsulfanyl-pyrimidine.

EXAMPLE 3

5-Cyano-4-methylamino-2-methylsulfanyl-pyrimidine

Through a cold (5° C.) solution of 4-chloro-5-cyano-2-methylsulfanyl-pyrimidine from Example 2 in diethyl ether (700 mL) was bubbled methylamine gas for a period of 20 minutes. The reaction mixture was stirred for 30 minutes at 5° C., then allowed to warm to room temperature and stirred overnight. Thin layer chromatography on silica gel plates indicated the reaction was incomplete. The reaction mixture was recooled to 5° C. and methylamine gas bubbled through the suspension with stirring for another 20 minutes. The reaction mixture was stirred at 25° C. for 6 hours, then allowed to stand overnight. The insoluble product was collected and suspended in water with stirring. The suspension was filtered and the product dried in vacuo to afford 25.87 g of the title compound 5-cyano-4-methylamino-2-methylsulfanyl-pyrimidine; mp 185–187° C.

Analysis calculated for $C_7H_8N_4S$: C, 46.65; H, 4.47; N, 31.09; Found: C, 46.62; H, 4.61; N, 31.43.

EXAMPLE 4

5-Cyano-4-methylamino-4-methylamino-pyrimidine

A mixture of 5-cyano-4-methylamino-2-methylsulfanyl-pyrimidine (25.86 g) from Example 3 and hydrazine hydrate (52 mL) in ethanol (250 mL) was heated at reflux with stirring for 3 hours. The reaction mixture was cooled to room temperature and the insoluble product was collected by filtration, washed with cold aqueous ethanol (1:1) to give 23 g of the title compound. Crystallization from ethanol afforded an analytically pure sample of 5-cyano-2-hydrazino-4-methylamino-pyrimidine; mp 247°–249° C.

Analysis calculated for $C_6H_8N_6$: C, 43.90; H, 4.91; N, 51.21; Found: C, 44.05; H, 4.92; N, 51.39.

EXAMPLE 5

2-Azido-5-cyano-4-methylamino-pyrimidine

To a cold (5° C.) solution of 5-cyano-2-hydrazino-4-methylamino-pyrimidine (21.7 g) from Example 4 in a mixture of water (260 mL) and concentrated HCl (26.5 mL) was added dropwise a solution of $NaNO_2$ (10.03 g) in water (25 mL) with overhead mechanical stirring. A white precipitate formed and after the addition was completed, the reaction was stirred for an additional 20 minutes at 5° C. The insoluble product was filtered and washed with cold water to give 22.4 g of the title compound after drying at 23° C. under high vacuum overnight. Crystallization from ethanol provided an analytically pure sample of 2-azido-5-cyano-4-methylamino-pyrimidine; mp 225°–230° C.

Analysis calculated for $C_6H_5N_7$: C, 41.14; H, 2.88; N, 55.99; Found: C, 40.88; H, 2.81; N, 55.82.

EXAMPLE 6

2-Amino-4-methylamino-5-pyrimidinecarboxaldehyde

To a suspension of 2-azido-5-cyano-4-methylaminopyrimidine (22.24 g) from Example 5 in 400 mL of 50% aqueous formic acid was added Raney Nickel catalyst (5 g). The reaction mixture was shaken under an atmosphere of hydrogen (40.1 psi) in a Parr hydrogenation apparatus. There was a vigorous evolution of gas as the mixture was shaken at room temperature. After 30 minutes the apparatus was vented, additional Raney Nickel (5 g) was added, the apparatus recharged with hydrogen, and the mixture shaken overnight. The catalyst was removed by filtration and the filtrate was evaporated under high vacuum. The residue was suspended in water and filtered. The insoluble material was collected and dissolved in 450 mL of boiling water. The aqueous solution was filtered and the pH of the filtrate was adjusted to 7 with 1N sodium hydroxide. The precipitated product was collected by filtration and recrystallized from ethanol to give 5.0 g of 2-amino-4-methylamino-5-pyrimidinecarboxaldehyde.

EXAMPLE 7

6-(2,6-Dimethylphenyl)-7-imino-8-methyl-7,8-dihydro-pyrido[2,3-d]pyrimidin-2-ylamine To 2-ethoxyethanol (7 mL) at –10° C. was added cautiously sodium hydride (60% suspended in mineral oil, 83 mg, 2.08 mmol) with stirring. The mixture was allowed to warm to room temperature and 2,6-dimethylphenylacetonitrile (1.5 g, 10.33 mmol) was added, followed by 2-amino-4-methylamino-5-pyrimidinecarboxaldehyde (1.5 g, 9.86 mmol) from Example 6. The resulting reaction mixture was heated at reflux for 2 hours, allowed to cool to room temperature, and poured into water. The insoluble crude product was collected and dried on the filter. The product was purified by dissolving in boiling ethyl acetate and adding hot hexane to the point just before precipitation. The hot solution was filtered and upon cooling the product precipitated to give 1.22 g of 6-(2,6-dimethylphenyl)-7-imino-8-methyl-7,8-dihydropyrido[2,3-d]pyrimidin-2-ylamine; mp 197°–198° C.

Analysis calculated for $C_{16}H_{17}N_5 \cdot 0.15 H_2O$: C, 68.14; H, 6.18; N, 24.83; Found: C, 68.19; H, 6.14; N, 24.60.

EXAMPLE 8

6-(2-Methylphenyl)-7-imino-8-methyl-7,8-dihydro-pyrido[2,3-d]pyrimidin-2-ylamine The title compound was prepared in similar manner to that described above in Example 7 starting from 2-methylphenylacetonitrile (0.72 g, 5.45 mmol) and 2-amino-4-methylamino-5-pyrimidinecarboxaldehyde (0.79 g, 5.19 mmol). As described above, sodium hydride (60% suspension in mineral oil, 0.083 g, 2.08 mmol), and 2-ethoxyethanol were employed as the respective base and solvent. The product was purified by crystallization from ethyl acetate-hexane to give 0.68 g of 6-(2-methylphenyl)-7-imino-8-methyl-7,8-dihydro-pyrido[2,3-d]pyrimidin-2-ylamine; mp 189°–190° C.

Analysis calculated for $C_{15}H_{15}N_5$: C, 67.91; H, 5.70; N, 26.40; Found: C, 67.52; H, 5.71; N, 26.33.

EXAMPLE 9

6-Phenyl-7-imino-8-methyl-7,8-dihydro-pyrido[2,3-d]-pyrimidin-2-ylamine

The title compound was prepared in a similar manner as described above in Example 7 starting from phenylacetonitrile (6.5 mL) and 2-amino-4-methylamino-5-pyrimidinecarboxaldehyde (8.10 g). However, sodium methoxide (0.5 g) was used in place of sodium hydride in this reaction. The product was purified by recrystallization from isopropyl alcohol to give 9.2 g of 6-phenyl-7-imino-8-methyl-7,8-dihydro-pyrido[2,3-d]-pyrimidin-2-ylamine; mp 201°–203° C.

Analysis calculated for $C_{14}H_{13}N_5$: C, 66.91; H, 5.21; N, 27.87; Found: C, 66.74; H, 5.22; N, 27.90.

EXAMPLE 10

2,7-Diamino-6-(2,6-dichlorophenyl)-pyrido[2,3-d]-pyrimidine (Prepared by the method of U.S. Pat. No. 3,534,039). To a solution of sodium 2-ethoxyethoxide prepared from 0.14 g of sodium and 60 mL of 2-ethoxyethanol was added 2.07 g of 2,4-diamino-5-pyrimidinecarboxaldehyde, and 2.79 g of 2,6-dichlorophenylacetonitrile. The mixture was heated at reflux for 4 hours, allowed to cool to room temperature, and the precipitated product was filtered and washed with diethyl ether to give 2,7-diamino-6-(2,6-dichlorophenyl)-pyrido[2,3-d]-pyrimidine; mp 325°–332° C.

EXAMPLE 11

2-Amino-6-(2,6-dichlorophenyl)-pyrido[2,3-d]pyrimindin-7-ol

A solution of 2,7-diamino-6-(2,6-dichlorophenyl)pyrido[2,3-d]pyrimidine (30.6 g) from Example 10 in concentrated HCl (200 mL) was heated at reflux for 24 hours. The reaction mixture was allowed to cool to room temperature, filtered, washed with water, and dried in vacuo to give 16.5 g of the crude product. The filtrate was refluxed for another 24 hours and upon cooling, yielded an additional 8.8 g of product. The two crops were combined and recrystallized from dimethylformamide, washed twice with diethyl ether, and dried in vacuo to afford 5.9 g of 2-amino-6-(2,6-dichlorophenyl)-pyrido[2,3-d]pyrimidin-7-ol; mp dec 410° C.

Analysis calculated for $C_{13}H_8Cl_2N_4O$: C, 50.84; H, 2.62; N, 18.24; Found: C, 50.45; H, 2.87; N, 18.09.

EXAMPLE 12

2-Amino-6-(2,6-dichlorophenyl)-8-methyl-pyrido[2,3-d]-pyrimindo-7(8H)-one

To a mixture of 2-amino-6-(2,6-dichlorophenyl)-pyrido[2,3-d]pyrimidin-7-ol (3.7 g) from Example 11 in dimethylformamide was added NaH (50% suspension in mineral oil, 0.64 g). The resulting slurry was heated at 65° C. for 0.5 hour until a solution formed. It was then cooled to 50° C. and a solution of methyl iodide (2.0 g) in dimethylformamide (10 mL) was added dropwise to the reaction. The reaction mixture was warmed and kept between 60° C.–80° C. for 3 hours. Upon cooling to room temperature, the reaction mixture was poured into ice water. The insoluble white product was filtered, washed with water, and recrystallized from ethanol using charcoal to give 1.9 g of 2-amino-6-(2,6-dichlorophenyl)-8-methyl-pyrido[2,3-d]pyrimidin-7(8H)-one; mp 235°–237° C.

Analysis calculated for $C_{14}H_{10}Cl_2N_4O$: C, 52.36; H, 3.14; N, 17.44; Found: C, 52.03; H, 3.24; N, 17.46.

EXAMPLE 13

2-Amino-6-(2,6-dimethylphenyl)-8-methyl-pyrido[2,3-4]-pyrimindin-7(8H)-one

A mixture of 6-(2,6-dimethylphenyl)-7-imino-8-methyl-7,8-dihydro-pyrido[2,3-d]pyrimidin-2-ylamine (0.96 g) from Example 7 and aqueous 6N HCl (25 mL) was heated at reflux for 2 days. The mixture was allowed to cool to room temperature and stand overnight at ambient temperature. An insoluble white solid was collected by filtration, washed with water, and air dried. The crude product was dissolved in hot ethanol, adding hot ethyl acetate to the point just before precipitation, and filtering the hot solution. Upon cooling, the pure product crystallized to give 25 mg of 2-amino-6-(2,6-dimethylphenyl)-8-methyl-pyrido[2,3-d]-pyrimidin-7(8H)-one; mp gradually dec over 235° C.

Analysis calculated for $C_{16}H_{16}N_4O \cdot 1$ HCl·0.15 $H_2O$; C, 59.38; H, 5.53; N, 17.31; Found: C, 59.42; H, 5.37; N, 17.53.

EXAMPLE 14

2-Amino-6-(2-methylphenyl)-8-methyl-pyrido[2,3-d]-pyrimidin-7(8H)-one

To a mixture of 6-(2-methylphenyl)-7-imino-8-methyl-7,8-dihydro-pyrido[2,3-d]pyrimidin-2-ylamine (0.30 g) from Example 8 and concentrated HCl (0.6 mL) was added water (11 mL). The reaction mixture was refluxed for 20 hours, then allowed to cool to room temperature. The white precipitate from the reaction mixture was filtered and washed with water. The product was dried in vacuo to give 0.21 g of 2-amino-6-(2-methylphenyl)-8-methyl-pyrido[2,3-d] pyrimidin-7(8H)-one; mp 239°–241° C.

Analysis calculated for $C_{15}H_{14}N_4O \cdot 1.46$ HCl: C, 56.45; H, 4.88; N, 17.55; Found: C, 56.47; H, 4.68; N, 17.59.

EXAMPLE 15

N-[6-(2,6-Dichlorophenyl)-8-methyl-7-oxo-7,8-dihydro-pyrido[2,3-d]pyrimidin-2-yl]acetamide A mixture of 64.2 mg (0.20 mmol) of 2-amino-6-(2,6-dichlorophenyl)-8-methyl-pyrido[2,3-d]pyrimidin-7(8H)-one (from Example 12) and 1 mL of acetic anhydride was heated to reflux. The resulting solution was maintained at reflux for 20 minutes and concentrated at atmospheric pressure to about 0.25 mL volume. The solution was cooled to 25° C. and diluted with diethyl ether (1 mL). The separated crystals were filtered and washed with diethyl ether to provide N-[6-(2,6-dichlorophenyl)-8-methyl-7-oxo-7,8-dihydro-pyrido[2,3-d]pyrimidin-2-yl]acetamide, wt 44.0 mg; mp 258°–260° C.

MS (CI) 363 ($M^+$+1).

Analysis calculated for $C_{16}H_{12}Cl_2N_4O_2$: C, 52.91; H, 3.33; N, 15.43; Found: C, 52.73; H, 3.47; N, 15.09.

EXAMPLE 16

N-[[6-(2,6-Dichlorophenyl)-7-oxo-8-methyl-7,8-dihydro-pyrido[2,3-d]pyrimidin-2-yl]-succinamic acid A mixture of 0.40 g (1.25 mmol) of 2-amino-6-(2,6-dichlorophenyl)-8-methyl-pyrido[2,3-d]pyrimidin-7(8H)-one (from Example 12) and 2.00 g (10.0 mmol) of succinic anhydride was reacted at 145° C. After 10 minutes the homogeneous melt was cooled and triturated with 25 mL of water. The mixture was heated at the boiling point for 5 minutes to hydrolyze excess anhydride. The mixture was filtered hot, and the cake was washed with 10 mL of boiling water. The dried cake (wt 0.50 g) was triturated with 8 mL of methanol: chloroform (1:20). The insoluble solid was filtered and washed with 1 mL of the same solvent to give 0.037 g of the pure title compound; mp 214°–218° C.

Analysis calculated for $C_{18}H_{14}Cl_2N_4O_4 \cdot 0.8$ $H_2O$; C, 49.62; H, 3.61; N, 12.86; Found: C, 49.26; H, 3.16; N, 12.83.

EXAMPLE 17

1-[6-(2,6-Dichlorophenyl)-7-oxo-8-methyl-7,8-dihydro-pyrido[2,3-d]pyrimadin-2-yl]pyrrolidine-2,5-diode The methanol-chloroform filtrate from Example 16 was chromatographed on silica gel, eluting with 1:20 v/v methanol:chloroform to give 0.161 g of pure crystalline N-[[6-(2,6-dichlorophenyl)-7-oxo-8-methyl-7,8-dihydro-pyrido[2,3-d]pyrimidin-2-yl]-pyrrolidine-2,5-dione; mp 303°–305° C.

Analysis calculated for $C_{18}H_{12}Cl_2N_4O_3$: C, 53.62; H, 3.00; N, 13.89; Found: C, 53.75; H, 2.90; N, 13.79.

EXAMPLE 18

4-Methylamino-2-methylsulfanyl-pyrimidine-5-carboxaldehyde

A solution of 4.00 g (0.022 mol) of 5-cyano-4-methylamino-2-methylsulfanyl-pyrimidine (from Example 3) in 150 mL of 50% aqueous formic acid was reacted with 6.0 g of water-wet Raney Nickel. The mixture was stirred at 25° C. for 12 hours. The solids were filtered and washed with 40 mL of 50% aqueous formic acid. With ice bath cooling, a cold saturated solution of potassium carbonate was added slowly to the green filtrate until complete precipitation of a solid was achieved (pH is still acidic; pH about 5). The solid was extracted into 200 mL of ethyl acetate, and the solution was dried (potassium carbonate), filtered, and concentrated; wt 2.30 g (57%); mp 98°–100° C.; tlc (1:1 hexane:ethyl acetate) one spot Rf 0.5.

Mass spectrum (CI) 184 (M+1).

Analysis calculated for $C_7H_9N_3OS$: C, 45.89; H, 4.95; N, 22.93. Found: C, 46.24; H, 4.88; N, 23.11.

EXAMPLE 18A

Alternative synthesis of 4-methylamino-2-methylsulfanyl-pyrimidine-5-carboxaldehyde To a solution of 4-chloro-2-methylsulfanyl-5-pyrimidinecarboxylate ethyl ester (18.66 g, 80.4 mmol) in 260 mL of tetrahydrofuran was added triethylamine (34 mL, 244 mmol), followed by 30 mL of a 40% aqueous solution of methylamine. The solution was stirred for 30 minutes at 25° C. then concentrated in vacuo and partitioned between chloroform and saturated aqueous sodium bicarbonate. The organic layer was washed with brine, dried over $MgSO_4$, filtered, and concentrated to provide a white solid. The solid was suspended in hexane and filtered to provide 14.70 g (81%) of 4-methylamino-2-methylsulfanyl-5-pyrimidinecarboxylate ethyl ester; mp 91°–93° C.

Analysis calculated for $C_9H_{13}N_3O_2S$: C, 47.56; H, 5.76; N, 18.49. Found: C, 47.93; H, 5.67; N, 18.58.

A solution of 4-methylamino-2-methylsulfanyl-5-pyrimidinecarboxylate ethyl ester (4.36 g, 19.3 mmol) in 60 mL of tetrahydrofuran was added dropwise to a room temperature suspension of lithium aluminum hydride (1.10 g, 29.0 mmol) in 40 mL of tetrahydrofuran. After 10 minutes the reaction was carefully quenched with 2 mL of water, 2 mL of 15% NaOH, and an additional 7 mL of water. The mixture was stirred for 1 hour, and the white precipitate which had formed was removed by filtration, and was washed with ethyl acetate. The filtrate was concentrated in vacuo and 3:1 hexane:ethyl acetate was added. The solids were collected to give 2.99 g (84%) of 4-methylamino-2-methylsulfanyl-5-pyrimidinemethanol; mp 155°–157° C.

Analysis calculated for $C_7H_{11}N_3OS$: C, 45.39; H, 5.99; N, 22.68. Found: C, 45.42; H, 5.93; N, 22.42.

4-Methylamino-2-methylsulfanyl-5-pyrimidine-methanol (2.40 g, 13.0 mmol) in 7 mL of acetic acid was added to a solution of sodium dichromate-dihydrate (1.30 g, 4.4 mmol) in 6 mL of acetic acid. After 2 hours at room temperature, additional sodium dichromate-dihydrate (0.3 g, 1.0 mmol) in 1 mL of acetic acid was added. After a total reaction time of 3.5 hours, the bright yellow solid was removed by filtration. Water (30 mL) was added to the filtrate, followed by aqueous ammonium hydroxide until basic (pH 9.0). The mixture was cooled in the refrigerator for 30 minutes. The precipitate was collected and dissolved in ethyl acetate, and the solution was dried over $MgSO_4$. Filtration and concentration in vacuo gave 0.72 g (30%) of 4-methylamino-2-methylsulfanyl-5-pyrimidinecarboxaldehyde; mp 99°–101° C.

Analysis calculated for $C_7H_9N_3OS$: C, 45.89; H, 4.95; N, 22.93. Found: C, 45.80; H, 4.96; N, 22.86.

EXAMPLE 19

6-(2,6-Dichlorophenyl)-8-methyl-2-methylsulfanyl-8H-pyrido[2,3-d]pyrimidin-7-ylideneamine Powdered potassium carbonate (0.8 g; 5.8 mmol) was added to a solution of 0.220 g (1.2 mmol) of the aldehyde from Example 18 and 0.235 g (1.26 mmol) (ca. 5% excess) of 2,6-dichlorophenylacetonitrile in 2.0 mL of dimethylformamide. The mixture was heated with stirring at 125° C. for 6 hours. Ethyl acetate (5 mL) was added to the cooled mixture, and the solids were filtered and washed with ethyl acetate. The filtrate was concentrated under reduced pressure. The residual gum was triturated with 10 mL of water, and the resulting solid was filtered, washed well with water, and dried. This crude material was chromatographed by placing a chloroform solution on a silica gel column wet with chloroform. The column was eluted with 1:1 (v/v) hexane:ethyl acetate, collecting the fractions that contain the Rf 0.25 spot on tlc (1:1 hexane:ethyl acetate). Evaporation of the solvents gave a solid. The solid product was dissolved in about 0.5 mL of methylene chloride. Crystals develop. Petroleum ether (ca. 2 mL) was added, and the crystals were filtered to provide 0.168 g (40%) of 6-(2,6-dichlorophenyl)-8-methyl-2-methylsulfanyl-8H-pyrido[2,3-d]pyrimidin-7-ylideneamine, mp 198°–200° C.

Mass spectrum (CI) 351 (M+1).

Analysis calculated for $C_{15}H_{12}Cl_2N_4S$: C, 51.29; H, 3.44; N, 15.95. Found: C, 51.31; H, 3.41; N, 15.73.

EXAMPLE 20

[6-(2,6-Dichlorophenyl)-7-imino-8-methyl-7,8-dihydropyrido[2,3-d]pyrimidin-2-yl]-(3-diethylaminopropyl)amine A solution of 0.275 g (0.78 mmol) of the methylsulfanyl derivative from Example 19 in 3 mL of N,N-diethylaminopropylamine was heated with stirring in a 135° C. oil bath (pot T=ca. 125° C.) for 16 hours. The excess amine was evaporated at reduced pressure, and the remaining oil was dissolved in 10 mL of diethyl ether. The turbid solution was clarified with "celite", filtered, and concentrated. The residue was triturated with petroleum ether and filtered; wt 0.288 g (85% yield). Recrystallization from ethyl acetate-petroleum ether gave pure product identified as [6-(2,6-dichlorophenyl)-7-imino-8-methyl-7,8-dihydro-pyrido[2,3-d]pyrimidin-2-yl]-(3-diethylaminopropyl)-amine; mp 154°–156° C.

Mass spectrum (CI) 433 ($M^+$).

Analysis calculated for $C_{21}H_{26}Cl_2N_6 \cdot 0.25 H_2O$; C, 57.60; H, 6.10; N, 19.19. Found: C, 57.46; H, 5.85; N, 19.16.

EXAMPLE 21

[6-(2,6-Dichlorophenyl)-8-methyl-7-oxo-7,8-dihydro-pyrido[2,3-d]pyrimidin-2-yl]-(3-diethylaminopropyl)amine A solution of 0.111 g (0.25 mmol) of the imino derivative from Example 20 in 5 mL of concentrated hydrochloric acid was heated at reflux for 6 days. The aqueous acid was evaporated at reduced pressure, and the residue was dissolved in 1.0 mL of water. Aqueous 10% potassium carbonate solution was added to completely precipitate a gum. The solvent was decanted, and the gum was dissolved in 15 mL of methylene chloride. The solution was dried over anhydrous potassium carbonate, filtered, and the filtrate was evaporated. The remaining gum was dissolved in 0.5 mL of diethyl ether. The crystalline product which developed was filtered and dried to provide [6-(2,6-dichlorophenyl)-8-methyl-7-oxo-7,8-dihydropyrido[2,3-d]pyrimidin-2-yl]-(3-diethylaminopropyl)-amine.

Mass spectrum (CI) 434(M$^+$).

EXAMPLE 22

6-(2,6-Dichlorophenyl)-2-(2-ethoxy-ethoxy)-8-methyl-8H-pyrido[2,3-d]pyrimidin-7-ylideneamine A quantity of 40.0 mg (1.0 mmol) of 60% sodium hydride-mineral oil was added with stirring to 5.0 mL of ethoxyethanol. After liberation of hydrogen ceased, 0.351 g (1.0 mmol) of the methylsulfanyl derivative of Example 19 was added. The solution was heated at 135° C. for 15 minutes. The reaction was cooled. Ice water (50 mL) was added to precipitate a gummy solid. This material was extracted into diethyl ether, the solution was dried (potassium carbonate), and concentrated to 15 mL volume. The separated crystals were filtered and washed with diethyl ether to afford the product identified as 6-(2,6-dichlorophenyl)-2-(2-ethoxy-ethoxy)- 8-methyl-8H-pyrido[2,3-d]pyrimidin-7-ylideneamine; mp 133°–135° C.

Mass spectrum (CI) 393 (M+1).

Analysis calculated for $C_{18}H_{18}Cl_2N_4O_2$: C, 54.97; H, 4.61; N, 14.25. Found: C, 55.05; H, 4.65; N, 14.15.

EXAMPLE 23

6-(2,6-Dichlorophenyl)-2-hydroxy-8-methyl-8H-pyrido-[2,3-d]pyrimidin-7-ylideneamine A solution of 78.0 mg (0.20 mmol) of the ethoxyethyl ether from Example 22 in 1.0 mL of 6N hydrochloric acid was heated at reflux for 5 minutes. The solvent was removed by evaporation under reduced pressure. The remaining solid hydrochloride salt was recrystallized from ethanol-ethyl acetate to afford crystalline 6-(2,6-dichlorophenyl)-2-hydroxy-8-methyl-8H-pyrido[2,3-d]pyrimidin-7-ylideneamine, hydrochloride; mp 255°–260° C.

Mass spectrum (CI) 321 (M+1).

Analysis calculated for $C_{14}H_{10}Cl_2N_4O \cdot HCl \cdot 0.3\ C_2H_5OH$: C, 47.21; H, 3.48; N, 15.08. Found: C, 47.21; H, 3.40; N, 14.73.

EXAMPLE 24

6-(2,6-Dichlorophenyl)-2-hydroxy-8-methyl-8H-pyrido[2,3-d]pyrimidin-7-one

A solution of 76.0 mg (0.19 mmol) of the imino derivative from Example 23 in 5.0 mL of concentrated hydrochloric acid was heated at reflux for 3 days, and the solvent was then removed by evaporation. The residue was triturated with water, filtered, and dried to afford 6-(2,6-dichlorophenyl)-2-hydroxy-8-methyl-8H-pyrido[2,3-d]pyrimidin-7-one, as a hydrate.

Mass spectrum (CI) 322 (M$^+$).

Analysis calculated for $C_{14}H_9Cl_2N_3O_2 \cdot 1.25\ H_2O$; C, 48.78; H, 3.37; N, 12.19. Found: C, 48.68; N, 3.25; N, 11.96.

EXAMPLE 25

6-(2,6-Dichlorophenyl)-2-[2-(diethylamino)ethoxy]-8-methyl-8H-pyrido[2,3-d]pyrimidin-7-one A mixture of 0.173 g (0.5 mmol) of the 2-hydroxy derivative from Example 24, 0.086 g (0.5 mmol) of 2-diethylaminoethyl chloride hydrochloride, 3 mL of dimethylformamide and 1.0 g of powdered anhydrous potassium carbonate was stirred at room temperature for 24 hours. Water (25 mL) was added to precipitate the crude product. Purification was effected by silica gel chromatography to provide the desired compound identified as 6-(2,6-dichlorophenyl)-2-[2-(diethyl-amino)ethoxy]-8-methyl-8H-pyrido[2,3-d]pyrimidin-7-one.

EXAMPLE 26

2-Amino-6-phenyl-8-methyl-pyrido[2,3-d]pyrimidin-7(8H)-one

This compound was prepared from 6-phenyl-7-imino-8-methyl-7,8-dihydro-pyrido[2,3-d]pyrimidin-2-ylamine of Example 9 by an acid hydrolysis procedure similar to that of Example 14; mp 250°–255° C.

EXAMPLE 27

2-Amino-6-(2,6-dichlorophenyl)-8-methyl-pyrido[2,3-d]-pyrimidin-7(8H)-thione

A mixture of 0.321 g (1.0 mmol) of 2-amino-6-(2,6-dichlorophenyl)-8-methyl-pyrido[2,3-d]pyrimidin-7-(8H)-one from Example 12 and 0.404 g (1.0 mmol) of Lawesson's Reagent in 10 mL of pyridine was heated at reflux with stirring for 24 hours. The solvent was evaporated under reduced pressure, and the residue was triturated with 20 mL of water, filtered, and the cake washed well with water. Purification was by silica gel chromatography to afford the desired compound identified as 2-amino-6-(2,6-dichlorophenyl)-8-methyl-pyrido[2,3-d]-pyrimidin-7(8H)-thione.

EXAMPLE 28

N-[6-(2,6-Dichlorophenyl)-8-methyl-2-methylsulfanyl -8H-pyrido[2,3-d]pyrimidin-7-ylidene]-acetamide

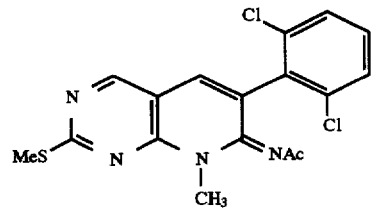

A mixture of 0.161 g (0.46 mmol) of 6-(2,6-dichlorophenyl)-8-methyl-2-methylsulfanyl-8H-pyrido[2,3-d]pyrimidin-7-ylideneamine from Example 19 and 1.0 mL of acetic anhydride was heated to solution at the boiling point. After 2 minutes of reflux, the solution was concentrated to one-half volume, whereupon crystals formed. The mixture was cooled, 2 mL of ether was added, and the product was filtered and washed with ether; mp 229°–231° C.

Mass spectrum (CI) 393 (M$^+$).

Analysis calculated for $C_{17}H_{14}Cl_2N_4OS$: C, 51.92; H, 3.59; N, 14.25. Found: C, 52.12; H, 3.62; N, 14.20.

EXAMPLE 29

N-6-(2,6-Dichlorophenyl)-2-(4-diethylaminobutylamino)-8-methyl-8H-pyrido[2,3-d]pyrimidin-7-ylidene]-acetamide

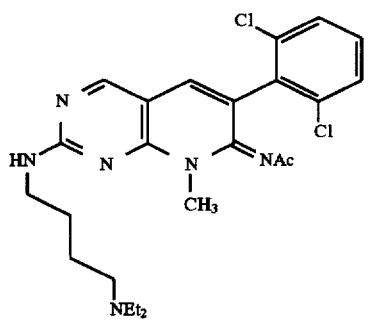

A mixture of 0.112 g (0.29 mmol) of N-[6-(2,6-dichlorophenyl)-8-methyl-2-methylsulfanyl-8H-pyrido[2,3-d]pyrimidin-7-ylidene]-acetamide of Example 28 and 1.0 mL (large excess) of 4-(diethyl-amino)butylamine was heated in a 135° C. oil bath with stirring. After 1 hour, the solution was concentrated at reduced pressure, and the residue was triturated with 1 mL of ethyl acetate. Petroleum ether (1 mL) was added, and the product was filtered.

Mass spectrum (CI) 489 ($M^+$).

EXAMPLE 30

2-Amino-6-(2,6-dichlorophenyl)-8-ethyl-pyrido[2,3-d]-pyrimindin-7(8H)-one

To a suspension of NaH (60% in mineral oil, 27 mg) in 5 mL of dimethylformamide was added 2-amino-6-(2,6-dichlorophenyl)-pyrido[2,3-d]pyrimidin-7(8H)-one (172 mg, 0.56 mmol) from Example 11. The mixture was heated at 50° C. for 1 hour resulting in a clear solution. Ethyl iodide (60 µL, 0.75 mmol) was added, and the solution was stirred at 50° C. for 3.5 hours, cooled to room temperature, and poured into 30 mL of ice water. The resulting precipitate was removed by filtration and partitioned between ethyl acetate and water. The organic layer was separated and dried over $MgSO_4$, filtered, and concentrated in vacuo. Flash chromatography, eluting with ethyl acetate, provided 104 mg (55%) of 2-amino-6-(2,6-dichlorophenyl)-8-ethyl-pyrido[2,3-d]pyrimidin-7(8H)-one; mp 207°–209° C.

Analysis calculated for $C_{15}H_{12}Cl_2N_4O$: C, 53.75; H, 3.61; N, 16.71. Found: C, 53.84; H, 3.67; N, 16.57.

EXAMPLE 31

2-Amino-6-(2,6-dichlorophenyl)-8-propyl-8H-pyrido[2,3-d]pyrimidin-7-one

To a suspension of NaH (60% in mineral oil, 31 mg) in 6 mL of dimethylformamide was added 2-amino-6-(2,6-dichlorophenyl)-pyrido[2,3-d]pyrimidin-7(8H)-one from Example 11 (205 mg, 0.67 mmol). The mixture was heated at 50° C. for 1 hour resulting in a clear solution. 1-Iodopropane (100 µL, 1.03 mmol) was added, and the solution was stirred at 50° C. for 10 minutes, then cooled to room temperature and poured onto 40 mL of ice water. The resulting precipitate was removed by filtration and washed with water. The residue was dried and purified by flash chromatography, eluting with 1:1 hexane:ethyl acetate to provide 159 mg (68%) of 2-amino-6-(2,6-dichlorophenyl)-8-propyl-8H-pyrido[2,3-d]pyrimidin-7-one; mp 196°–197° C.

Analysis calculated for $C_{16}H_{14}Cl_{12}N_4O$: C, 55.03; H, 4.04; N, 16.04. Found: C, 55.28; H, 4.22; N, 15.81.

EXAMPLE 32

2-Amino-8-butyl-6-(2,6-dichlorophenyl)-8H-pyrido[2,3-d]pyrimidin-7-one

To a suspension of NaH (60% in mineral oil, 34 mg) in 6 mL of dimethylformamide was added 2-amino-6-(2,6-dichlorophenyl)-pyrido[2,3-d]pyrimidin-7(8H)-one (202 mg, 0.66 mmol). The mixture was heated to 50° C., resulting in a clear solution. 1-Iodobutane (105 µL, 0.92 mmol) was added, and the solution was stirred at 50° C. for 30 minutes, then cooled to room temperature and poured onto 40 mL of ice water. The resulting precipitate was removed by filtration and washed with water. The residue was dried and purified by flash chromatography, eluting with a gradient of 1:1 hexane:ethyl acetate to all ethyl acetate to provide 152 mg (64%) of 2-amino-8-butyl-6-(2,6-dichlorophenyl)-8H-pyrido[2,3-d]pyrimidin-7-one; mp 202°–205° C.

Analysis calculated for $C_{17}H_{16}Cl_2N_4O \cdot 0.08$ EtOAc: C, 56.18; H, 4.52; N, 15.13. Found: C, 56.39; H, 4.64; N, 14.99.

EXAMPLE 33

2-Amino-6-(2,6-dichlorophenyl)-8-isobutyl-8H-pyrido[2,3-d]pyrimidin-7-one

To a suspension of NaH (60% in mineral oil, 36 mg) in 8 mL of dimethylformamide was added 2-amino-6-(2,6-dichlorophenyl)-pyrido[2,3-d]pyrimidin-7(8H)-one (205 mg, 0.67 mmol). The mixture was heated at 60° C. for 20 minutes resulting in a clear solution. 1-Iodo-2-methylpropane (110 µL, 0.94 mmol) was added, and the solution was stirred at 50° C. for 30 minutes. An additional amount of 1-iodo-2-methylpropane (40 µL, 0.34 mmol) was added, and the solution was stirred at 50° C. for 40 minutes, then cooled to room temperature and poured onto 40 mL of ice water. The resulting precipitate was removed by filtration and washed with water. The gummy residue was dissolved in ethyl acetate and washed with water. The organic layer was dried over magnesium sulfate, filtered, and concentrated in vacuo. The resulting solid was purified by flash chromatography, eluting with 1:1 hexane:ethyl acetate to provide 123 mg (51%) of 2-amino-6-(2,6-dichlorophenyl)-8-isobutyl-8H-pyrido[2,3-d]pyrimidin-7-one; mp 193°–195° C.

Analysis calculated for $C_{17}H_{16}Cl_2N_4O$: C, 56.21; H, 4.44; N, 15.42. Found: C, 56.60; H, 4.59; N, 15.11.

EXAMPLE 34

2-Amino-6-(2,6-dichlorophenyl)-8-(3-dimethylamino-propyl)-8H-pyrido[2,3-d]pyrimidin-7-one To a suspension of NaH (60% in mineral oil, 50 mg) in 8 mL of dimethylformamide was added 2-amino-6-(2,6-dichlorophenyl)-pyrido[2,3-d]pyrimidin-7(8H)-one (319 mg, 1.04 mmol). The mixture was heated at 70° C. for 1.5 hours resulting in a clear solution. In a second flask containing NaH (60% in mineral oil, 68 mg) in 6 mL of dimethylformamide was added 3-dimethylaminopropyl chloride hydrochloride (248 mg, 1.56 mmol). This suspension was stirred at room temperature for 30 minutes, then heated at 70° C. for 10 minutes and added to the above solution of the sodium salt of 2-amino-6-(2,6-dichlorophenyl)-pyrido[2,3-d]pyrimidin-7(8H)-one. The resultant suspension was heated at 70° C. for 3 hours, then cooled to room temperature and filtered washing with ethyl acetate. The filtrate was concentrated in vacuo and ethyl acetate and hexane were added. The resulting solid was collected by filtration and dried in vacuo to provide 216 mg (53%) of 2-amino-6-(2,6-dichlorophenyl)-8-(3-dimethylaminopropyl)-8H-pyrido[2,3-d]pyrimidin-7-one; mp 136°–141° C.

Analysis calculated for $C_{18}H_{19}Cl_2N_5O$: C, 55.11; H, 4.88; N, 17.85. Found: C, 55.07; H, 5.00; N, 17.53.

EXAMPLE 35

[2-Amino-6-(2,6-dichlorophenyl)-7-oxo-7H-pyrido[2,3-d]-pyrimidin-8-yl]-acetic acid methyl ester To a suspension of NaH (60% in mineral oil, 38 mg) in 6 mL of dimethylformamide was added 2-amino-6-(2,6-dichlorophenyl)-pyrido[2,3-d]pyrimidin-7(8H)-one (203 mg, 0.66 mmol). The mixture was heated at 50° C. for 40 minutes resulting in a clear solution. Methyl chloroacetate (90 µL, 1.03 mmol) was added, and the solution was heated at 50° C. for 20 minutes, then cooled to room temperature and poured onto 30 mL of ice water. The resulting precipitate was removed by filtration and washed with water. The aqueous filtrate was extracted with ethyl acetate, and the organic layer was dried over magnesium sulfate, filtered, and concentrated. The solids were combined and purified by flash chromatography, eluting with a gradient of 1:1 hexane:ethyl acetate to all ethyl acetate to provide 152 mg (61%) of [2-amino-6-(2,6-dichlorophenyl)-7-oxo-7H-pyrido[2,3-d]pyrimidin-8-yl]-acetic acid methyl ester; mp 188°–190° C.

Analysis calculated for $C_{16}H_{12}Cl_2N_4O_3$: C, 50.68; H, 3.19; N, 14.77. Found: C, 50.74; H, 3.31; N, 14.39.

EXAMPLE 36

[2-Amino-6-(2,6-dichlorophenyl)-7-oxo-7H-pyrido[2,3-d]-pyrimidin-8-yl]-acetic acid tert-butyl ester To a suspension of NaH (60% in mineral oil, 67 mg) in 10 mL of dimethylformamide was added 2-amino-6-(2,6-dichlorophenyl)-pyrido[2,3-d]pyrimidin-7(8H)-one (398 mg, 1.30 mmol). The mixture was heated at 45° C. to 55° C. for 40 minutes resulting in a clear solution. Tert-butyl bromoacetate (250 µL, 1.69 mmol) was added, and the solution was stirred at 50° C. for several minutes, then cooled to room temperature and poured onto 60 mL of ice water. The resulting precipitate was removed by filtration and washed with water. The solid was purified by flash chromatography, eluting with a gradient of 1:2 hexane:ethyl acetate to all ethyl acetate to provide 165 mg (30%) of [2-amino-6-(2,6-dichlorophenyl)-7-oxo-7H-pyrido[2,3-d]pyrimidin-8-yl]-acetic acid tert-butyl ester; mp 171°–173° C.

Analysis calculated for $C_{19}H_{18}Cl_2N_4O_3$: C, 54.17; H, 4.31; N, 13.30. Found: C, 54.17; H, 4.34; N, 13.08.

EXAMPLE 37

6-(2,6-Dichlorophenyl)-8-methyl-2-methylsulfanyl-8H-pyrido[2,3-d]pyrimidin-7-one A solution of 0.20 g (0.51 mmol) of N-[6-(2,6-dichlorophenyl)-8-methyl-2-methylsulfanyl-8H-pyrido[2,3] pyrimidin-7-ylidene]-acetamide of Example 28 in 2.0 mL of 6[hydrochloric acid was heated with stirring to the boiling point. Crystals separated immediately. The thick mixture was heated an additional 2 minutes at the boiling point, cooled, and filtered. The cake was washed well with water and dried; wt 0.175 g (92%); mp 249°–251° C.

Mass spectrum (CI) 352 (M⁺).

Analysis calculated for $C_{15}H_{11}Cl_2N_3OS \cdot 1.4\ H_2O$; C, 47.58; H, 3.57; N, 11.16. Found: C, 47.60; H, 3.12; N, 11.14.

EXAMPLE 38

6-(2,6-Dichlorophenyl)-8-methyl-2-[3-(4-methylpiperazin-1-yl)-prolyamino]-8H-pyrido[2,3-d]pyrimidin-7-one A mixture of 0.152 g (0.43 mmol) of 6-(2,6-dichlorophenyl)-8-methyl-2-methylsulfanyl-8H-pyrido[2,3-d]pyrimidin-7-one of Example 37 and 1.0 g (6.40 mmol) of 1-(3-aminopropyl)-4-methylpiperazine was heated with stirring in a 170° C. oil bath (pot T=ca. 160° C.) for 3 hours. The excess amine was evaporated at reduced pressure. Water (5 mL) was added, and the separated gum was extracted into 50 mL of 10% methylene chloride-ether. The organic phase was washed three times with 10 mL of water, dried (potassium carbonate), charcoaled, filtered, and concentrated. The remaining gum was dissolved in 3 mL of ether. The crystals that separated on inducement were filtered and washed with ether; wt 0.033 g; mp 170°–172° C.

Mass spectrum (CI) 461 (M⁺).

Analysis calculated for $C_{22}H_{26}Cl_2N_6O$: C, 57.27; H, 5.68; N, 18.21. Found: C, 57.39; H, 5.70; N, 18.10.

EXAMPLE 39

6-(2,6-Dichlorophenyl)-2-methanesulfonyl-8-methyl-8H-pyrido[2,3-d]pyrimidin-7-one A quantity of 0.346 g (1.00 mmol) of 50% to 60% m-chloroperbenzoic acid (assuming 50% peracid was present) was added at 25° C. to a stirred solution of 0.165 g (0.47 mmol) of 6-(2,6-dichlorophenyl)-8-methyl-2-methylsulfanyl-8H-pyrido[2,3-d]pyrimidin-7-one of Example 37 in 15 mL of chloroform, and the solution was stirred overnight. A quantity of 0.25 g (3.20 mmol) of dimethylsulfoxide was added to reduce any excess peracid. After 15 minutes, the chloroform solution was washed with 30 mL of saturated sodium bicarbonate and then with water. The separated organic layer was dried over sodium sulfate, filtered, and concentrated to ca. 5 mL volume. Crystals separated. Added ca. 5 mL of petroleum ether and filtered; wt 0.165 g (92%); mp >290° C.

Mass spectrum (CI) 384 (M⁺).

Analysis calculated for $C_{15}H_{11}Cl_2N_3O_3S$: C, 46.89; H, 2.89; N, 10.94. Found: C, 47.14; H, 2.96; N, 10.87.

EXAMPLE 40

6-(2,6-Dichlorophenyl)-8-methyl-2-methylamino-8H-pyrido[2,3-d]pyrimidin-7-one

A quantity of 0.165 g (0.47 mmol) of 6-(2,6-dichlorophenyl)-8-methyl-2-methylsulfanyl-8H-pyrido[2,3-d]pyrimidin-7-one of Example 37 was placed in a pressure tube with a magnetic stirring bar. The tube was cooled in a dry ice-acetone bath and ca. 3 mL of monomethylamine gas was condensed in the tube. Dimethylformamide (1.0 mL) was added, and the tube was closed and allowed to warm to room temperature. With stirring, the reaction mixture was heated behind a shield in a 110° C. oil bath. After 10 minutes, all solid was in solution. The solution was heated in the oil bath for 20 hours. The tube was cooled in an ice-acetone bath, opened, and warmed to room temperature to vent the excess amine. Most of the dimethylformamide was evaporated at reduced pressure to yield crystals. The solid was triturated with 5 mL of water, filtered, washed with water and dried; wt 0.128 g. Purification was effected by recrystallization from ethyl acetate-petroleum ether to give 0.081 g of pure product; mp 243°–244° C.

Mass spectrum (CI) 335 (M$^+$).

Analysis calculated for $C_{15}H_{12}Cl_2N_4O$: C, 53.75; H, 3.61; N, 16.71. Found: C, 53.91; H, 3.64; N, 16.80.

EXAMPLE 41

6-(2,6-Dichlorophenyl)-2-dimethylamino-8-methyl-8H-pyrido[2,3-d]pyrimidin-7-one

This compound was prepared by a procedure similar to that described in Example 40 starting with 6-(2,6-dichlorophenyl)-8-methyl-2-methylsulfanyl-8H-pyrido[2,3-d]pyrimidin-7-one of Example 37 and dimethylamine gas; mp 256°–258° C.

Mass spectrum (CI) 349 (M$^+$).

Analysis calculated for $C_{16}H_{14}Cl_2N_4O$: C, 55.03; H, 4.04; N, 16.04. Found: C, 55.13; H, 4.06; N, 16.03.

EXAMPLE 42

6-(2,6-Dichlorophenyl)-2-ethylamino-8-methyl-8H-pyrido[2,3-d]pyrimidin-7-one

This compound was prepared by a procedure similar to that described in Example 40 starting with 6-(2,6-dichlorophenyl)-8-methyl-2-methylsulfanyl-8H-pyrido[2,3-d]pyrimidin-7-one of Example 37 and ethylamine gas; mp 180°–182° C.

Mass spectrum (CI) 349 (M$^+$).

Analysis calculated for $C_{16}H_{14}Cl_2N_4O$: C, 55.03; H, 4.04; N, 16.04. Found: C, 55.17; H, 4.08; N, 16.07.

EXAMPLE 43

6-(2,6-Dichlorophenyl)-2-(2-hydroxyethylamino)-8H-methyl-8H-pyrido[2,3-d]pyrimidin-7-one A mixture of 0.165 g (0.47 mmol) of 6-(2,6-dichlorophenyl)-8-methyl-2-methylsulfanyl-8H-pyrido[2,3-d]pyrimidin-7-one from Example 37, 1.0 g (16.4 mmol) of ethanolamine and 0.5 mL of dimethylformamide was heated in a 125° C. oil bath with stirring for 1.5 hours. The resulting solution was concentrated in vacuo, and the remaining gum was triturated with 5 mL of water. The tacky solid was filtered, washed well with water, and recrystallized from acetone/petroleum ether to give 0.071 g of pure product; mp 128°–131° C.

Mass spectrum (CI) 365 (M$^+$).

Analysis calculated for $C_{16}H_{14}Cl_2N_4O_2 \cdot 0.7\ C_3H_6O$: C, 53.56; H, 4.52; N, 13.81. Found: C, 53.88; H, 4.46; N, 14.17.

EXAMPLE 44

6-(2,6-Dichlorophenyl)-2-isopropylamino-8-methyl-8H-pyrido[2,3-d]pyrimidin-7-one This compound was prepared by a procedure similar to that described in Example 40 starting with 6-(2,6-dichlorophenyl)-8-methyl-2-methylsulfanyl-8H-pyrido[2,3-d]pyrimidin-7-one of Example 37 and isopropylamine; mp 194°–196° C.

Mass spectrum (CI) 363 (M$^+$).

Analysis calculated for $C_{17}H_{16}Cl_2N_4O$: C, 56.21; H, 4.44; N, 15.42. Found: C, 56.17; H, 4.48; N, 15.43.

EXAMPLE 45

3-Butylamino-6-(2,6-dichlorophenyl)-8-methyl-8H-pyrido[2,3-d]pyrimidin-7-one

A mixture of 0.177 g (0.50 mmol) of 6-(2,6-dichlorophenyl)-8-methyl-2-methylsulfanyl-8H-pyrido[2,3-d]pyrimidin-7-one of Example 37, 10 mL of n-butylamine and 1.0 mL of dimethylformamide was heated with stirring to reflux (110° C. oil bath). After 1 hour, solution was complete. After 20 hours reflux, the excess amine and dimethylformamide were evaporated, and the residue was triturated with water, filtered, washed with water, and dried; wt 0.180 g. Recrystallization from ethyl acetate/petroleum ether gave pure product; wt 0.116 g; mp 184°–186° C.

Mass spectrum (CI) 377 (M$^+$).

Analysis calculated for $C_{18}H_{18}Cl_2N_4O$: C, 57.31; H, 4.81; N, 14.85. Found: C, 57.41; H, 4.81; N, 14.83.

EXAMPLE 46

2-Benzylamino-6-(2,6-dichlorophenyl)-8-methyl-8H-pyrido[2,3-d]pyrimidin-7-one

A mixture of 0.165 g (0.47 mmol) of 6-(2,6-dichlorophenyl)-8-methyl-2-methylsulfanyl-8H-pyrido-[2,3-d]pyrimidin-7-one of Example 37, 0.50 g (4.70 mmol) of benzylamine and 0.5 mL of dimethylformamide was heated with stirring in a 120° C. oil bath. After 5 minutes, solution was complete. After 5 hours, the excess amine and dimethylformamide were evaporated at reduced pressure, and the residue was triturated with a solution of 1 mL of acetone and 2 mL of petroleum ether. The tacky solid was filtered and recrystallized from ethyl acetate/petroleum ether to give 0.092 g of pure product; mp 217°–219° C.

Mass spectrum (CI) 411 (M$^+$).

Analysis calculated for $C_{17}H_{14}Cl_2N_4O_5$: C, 61.33; H, 3.92; N, 13.62. Found: C, 61.30; H, 4.02; N, 13.59.

EXAMPLE 47

6-(2,6-Dichlorophenyl)-8-methyl-2-(3-morpholin-4-yl-propylamino)-8H-pyrido[2,3-d]pyrimidin-7-one A mixture of 0.165 g (0.47 mmol) of 6-(2,6-dichlorophenyl)-8-methyl-2-methylsulfanyl-8H-pyrido[2,3-d]pyrimidin-7-one of Example 37, 1.00 g (6.90 mmol) of N-(3-aminopropyl)morpholine and 0.5 mL of dimethylformamide was heated with stirring in a 125° C. oil bath. After 2 minutes, solution was complete. After 1.5 hours, the excess amine and dimethylformamide were evaporated at reduced pressure and the residue was triturated with 5 mL of water. The gum was dissolved in 25 mL of ethyl acetate, and the solution was washed with 2×5 mL of water, dried (potassium carbonate), and concentrated. Upon dissolution in 5 mL of ether, crystals of pure product separated; wt 0.101 g; mp 140°–142° C.

Mass spectrum (CI) 448 (M$^+$).

Analysis calculated for $C_{21}H_{23}Cl_2N_4O_2$: C, 56.26; H, 5.17; N, 15.62. Found: C, 56.48; H, 5.24; N, 15.53.

EXAMPLE 48

6-(2,6-Dichlorophenyl)-2-[2-(3,4-dimethoxyphenyl)-ethylamino]-8-methyl-8H-pyrido[2,3-d]pyrimidin-7-one A mixture of 0.165 g (0.47 mmol) of 6-(2,6-dichlorophenyl)-8-methyl-2-methylsulfanyl-8H-pyrido[2,3- d]pyrimidin-7-one of Example 37, 0.80 g (4.40 mmol) of 2-(3,4-dimethoxyphenyl)ethylamine and 0.5 mL of dimethylformamide was heated with stirring in a 125° C. oil bath. After 2 minutes, solution was complete. After 5 hours, the excess amine and dimethylformamide were evaporated at reduced pressure, and the residue was triturated with 10 mL of water. The gum was dissolved in 75 mL of ether, and the solution was washed with 2×10 mL of water and dried (potassium carbonate). The hydrochloride salt was prepared by passing hydrogen chloride gas into this ether solution to precipitate a gum. The ether was decanted>and the gum was dissolved in 2.0 mL of 2-propanol. Crystals separated on inducement. Ether (10 mL) was added, and the pure crystals were filtered and washed with ether; wt 0.034 g; mp 152°–155° C.

Mass spectrum (CI) 485 (M$^+$).

Analysis calculated for $C_{24}H_{22}Cl_2N_4O_3 \cdot HCl \cdot 0.75\ C_3H_8O$: C, 55.61; H, 5.16; N, 9.88. Found: C, 55.32; H, 5.28; N, 9.50.

EXAMPLE 49

6-(2,6-Dichlorophenyl)-8-methyl-2-[(pyridin-2-ylmethyl]-amino]-8H-pyrido[2,3-d]pyrimidin-7-one A mixture of 0.165 g (0.47 mmol) of 6-(2,6-dichlorophenyl)-8-methyl-2-methylsulfanyl-8H-pyrido[2,3-d]pyrimidin-7-one of Example 37, 1.08 g (10.0 mmol) of 2-(aminomethyl)pyridine and 0.5 mL of dimethylformamide was heated with stirring in a 130° C. oil bath. After 2 minutes, solution was complete. After 2 hours, the excess amine and dimethylformamide were evaporated at reduced pressure. Ether (5 mL) was added to the residue. Crystals immediately developed. Water (5 mL) was added, and the entire mixture was filtered. The cake was washed 5 mL of ether, 5 mL of water, and then dried; wt 0.164 g. Recrystallization from ethyl acetate gave 0.075 g of pure product; mp 198°–201° C.

Mass spectrum (CI) 412 (M$^+$).

Analysis calculated for $C_{20}H_{15}Cl_2N_5O$: C, 58.27; H, 3.67; N, 16.99. Found: C, 58.36; H, 3.82; N, 16.82.

EXAMPLE 50

6-(2,6-Dichlorophenyl)-8-methyl-2-[(pyridin-3-ylmethyl)-amino]-8H-pyrido[2,3-d]pyrimidin-7-one This compound was prepared by a procedure similar to that described in Example 49 starting with 0.165 g (0.47 mmol) of 6-(2,6-dichlorophenyl)-8-methyl-2-methylsulfanyl-8H-pyrido[2,3-d]pyrimidin-7-one of Example 37 and 1.08 g (10.0 mmol) of 3-(aminomethyl)-pyridine yielding 0.053 g of pure product; mp 224°–226° C.

Mass spectrum (CI) 412 (M$^+$).

Analysis calculated for $C_{20}H_{15}Cl_2N_5O$: C, 58.27; H, 3.67; N, 16.99. Found: C, 58.36; H, 3.78; N, 16.79.

EXAMPLE 51

6-(2,6-Dichlorophenyl)-8-methyl-2-(2-pyridin-2-yl-ethylamino)-8H-pyrido[2,3-d]pyrimidin-7-one This compound was prepared by a procedure similar to that described in Example 49 starting with 0.165 g (0.47 mmol) of 6-(2,6-dichlorophenyl)-8-methyl-2-methylsulfanyl-8H-pyrido[2,3-d]pyrimidin-7-one of Example 37 and 1.00 g (8.20 mmol) of 2-(2-aminoethyl)-pyridine yielding 0.082 g of pure product; mp 173°–174° C.

Mass spectrum (CI) 426 (M$^+$).

Analysis calculated for $C_{21}H_{17}Cl_2N_5O$: C, 59.17; H, 4.02; N, 16.43. Found: C, 59.28; H, 4.11; N, 16.29.

EXAMPLE 52

6-(2,6-Dichlorophenyl]-2-[3-[4-(2-methoxyphenyl)-piperazin-1-yl]-propylamino]-8-methyl-8H-pyrido[2,3-d]pyrimidin-7-one This compound was prepared by a procedure similar to that described in Example 49 starting with 0.165 g (0.47 mmol) of 6-(2,6-dichlorophenyl)-8-methyl-2-methylsulfanyl-8H-pyrido[2,3-d]pyrimidin-7-one of Example 37 and 1.00 g (4.00 mmol) of 1-(3-aminopropyl)-4-(2-methoxyphenyl)piperazine yielding 0.103 g of pure product; mp 187°–188° C.

Mass spectrum (CI) 553 (M$^+$).

Analysis calculated for $C_{28}H_{30}Cl_2N_6O_2$: C, 60.76; H, 5.46; N, 15.18. Found: C, 61.04; H, 5.41; N, 15.20.

EXAMPLE 53

6-(2,6-Dichlorophenyl)-2-methanesulfinyl-8-methyl-8H-pyrido[2,3-d]pyrimidin-7-one This compound was isolated as a byproduct in the m-chloroperbenzoic acid oxidation of 6-(2,6-dichlorophenyl)- 8-methyl-2-methylsulfanyl-8H-pyrido[2,3-d]-pyrimidin-7-one of Example 37 in one run that was similar to Example 39 but where the reaction time was shortened; mp 244°–247° C.

Mass spectrum (CI) 368 (M$^+$).

Analysis calculated for $C_{15}H_{11}Cl_2N_3O_2S$: C, 48.93; H, 3.01; N, 11.41. Found: C, 48.42; H, 3.20; N, 11.05.

EXAMPLE 54

6-(2,6-Dichlorophenyl)-8-methyl-2-phenylamino-8H-pyrido[2,3-d]pyrimidin-7-one

A solution of 0.113 g (0.29 mmol) of 6-(2,6-dichlorophenyl)-2-methanesulfonyl-8-methyl-8H-pyrido[2,3-d]pyrimidin-7-one of Example 39 in 1.00 g (10.70 mmol) of aniline was maintained at reflux (184° C.) for 3 minutes. Most of the excess aniline was evaporated at reduced pressure. The remaining gum was dissolved in 1.0 mL of ethyl acetate. Crystals developed on inducement; wt 0.088 g. Further purification to remove dark colors was effected by silica gel chromatography, eluting with chloroform and then 50% hexane-ethyl acetate to obtain pure crystalline product; wt 0.046 g; mp 247°–249° C.

Mass spectrum (CI) 397 (M$^+$).

Analysis calculated for $C_{20}H_{14}Cl_2N_4O$: C, 60.47; H, 3.55; N, 14.10. Found: C, 60.25; H, 3.64; N, 14.00.

EXAMPLE 55

2-(3-Bromophenylamino)-6-(2,6-dichlorophenyl)-8-methyl-8H-pyrido[(3-d]pyrimidin-7-one A solution of 0.155 g (0.40 mmol) of 6-(2,6-dichlorophenyl)-2-methanesulfonyl-8-methyl-8H-pyrido[2,3-d]pyrimidin-7-one of Example 39 in 0.50 g (2.90 mmol) of 3-bromoaniline was maintained at reflux (251° C.) for 5 minutes. Most of the excess 3-bromoaniline was evaporated at reduced pressure. The cooled remaining gum was triturated 1.0 mL of ether. The violet crystals that developed were filtered and washed with 2 mL of ether; wt 0.186 g. Further purification to remove dark colors was effected by silica gel chromatography, eluting with chloroform and then 50% hexane/ethyl acetate to obtain pure crystalline product; wt 0.104 g; mp 246°–248° C.

Mass spectrum (CI) 447 (M$^+$).

Analysis calculated for $C_{20}H_{13}BrCl_2N_4O$: C, 50.45; H, 2.75; N, 11.77. Found: C, 50.53; H, 2.76; N, 11.52.

EXAMPLE 56

2-(4-Chlorophenylamino)-6-(2,6-dichlorophenyl)-8-methyl-8H-pyrido[2,3-d]pyrimidin-7-one A mixture of 0.113 g (0.29 mmol) of 6-(2,6-dichlorophenyl)-2-methanesulfonyl-8-methyl-8H-pyrido[2,3-d]pyrimidin-7-one of Example 39 in 0.50 g (3.90 mmol) of 4-chloroaniline was heated, with stirring, at the boiling point (238° C.) for 5 minutes. Ethyl acetate (3 mL) was added to the cooled dark blue reaction solution. Petroleum ether (3 mL) was added to completed precipitation of a dark solid. This was filtered and washed with 50% hexane-ethyl acetate; wt 0.078 g. The crude solid was purified to remove dark colors by silica gel chromatography, eluting with chloroform and then 50% hexane-ethyl acetate to obtain pure crystalline product; wt 0.056 g; mp 255°–256° C.

Mass spectrum (CI) 431 (M$^+$).

Analysis calculated for $C_{20}H_{13}Cl_3N_4O$: C, 55.64; H, 3.04; N, 12.98. Found: C, 55.75; H, 3.04; N, 12.97.

EXAMPLE 57

2-(Benzo[1,3]dioxol-5-ylamino)-6-(2,6-dichlorophenyl)-8-methyl-8H-pyrido[2,3-d]pyrimidin-7-one A mixture of 0.113 g (0.29 mmol) of 6-(2,6-dichlorophenyl)-2-methanesulfonyl-8-methyl-8H-pyrido[2,3-d]pyrimidin-7-one of Example 39 and 0.50 g (3.70 mmol) of 3,4-methylenedioxyaniline was heated, with stirring, in a 200° C. oil bath. The resulting solution was heated for 5 minutes and cooled to room temperature. Ethyl acetate (2 mL) was added, and some traces of solids were filtered. The crystals that slowly developed in the filtrate were filtered and washed with 2 mL of ethyl acetate; wt 0.080 g. The solid was purified to remove dark colors by silica gel chromatography, eluting with chloroform and then 50% hexane/ethyl acetate to obtain pure crystalline product; wt 0.054 g; mp 240°–241° C.

Mass spectrum (CI) 441 (M$^+$).

Analysis calculated for $C_{21}H_{14}Cl_2N_4O_3$: C, 57.16; H, 3.20; N, 12.70. Found: C, 56.95; H, 3.11; N, 12.47

EXAMPLE 58

6-(2,6-Dichlorophenyl)-8-methyl-2-(pyridin-4-ylamino)-8H-pyrido[2,3-d]pyrimidin-7-one A mixture of 0.550 g (1.25 mmol) of 6-(2,6-dichlorophenyl)-2-methanesulfonyl-8-methyl-8H-pyrido[2,3-d]pyrimidin-7-one of Example 39 and 1.50 g (16.0 mmol) of 4-aminopyridine was heated, with stirring, in a 150° C. oil bath. The resulting solution was heated for 10 minutes and cooled to room temperature. The hardened melt was triturated with 3 mL of methanol. After 24 hours of standing, the granular solid that developed was filtered and washed with 2 mL of methanol and 2 mL of ether; wt 0.471 g. The hydrochloride salt was prepared as follows: The above crude base was suspended in 5 mL of methanol. With stirring, 1 mL of 2N hydrochloric acid was added to give a complete solution. Additional hydrochloric acid was added until the solution was slightly turbid. The crystals that separated on inducement were filtered and washed with 10 mL of 10% methanol-ether and then ether; wt 0.485 g. Recrystallization from methanol/ether gave pure crystalline product; wt 0.405 g; mp 338°–340° C.

Mass spectrum (CI) 398 (M$^+$).

Analysis calculated for $C_{19}H_{13}Cl_2N_5O \cdot HCl \cdot H_2O$: C, 50.40; H, 3.56; N, 15.47. Found: C, 50.78; H, 3.18; N, 15.50.

EXAMPLE 59

6-(2,6-Dichlorophenyl)-8-methyl-2-[4-(4-methylpiperazin-1-yl)-butylamino]-8H-pyrido[2,3-d]-pyrimidin-7-one A mixture of 0.152 g (0.43 mmol) of 6-(2,6-dichlorophenyl)-8-methyl-2-methylsulfanyl-8-pyrido[2,3-d]pyrimidin-7-one of Example 37 and 0.50 g (2.90 mmol) of 1-(4-aminobutyl)-4-methylpiperazine was heated with stirring in a 170° C. oil bath. After 2 minutes, solution was complete. After 2 hours, the solution was cooled to room temperature, and the dark gum was dissolved in 25 mL of ether. The solution was washed with 4×5 mL of water. Most of the color went into the water wash. The ether solution was dried over potassium carbonate, filtered, and concentrated to ca. 2 mL volume. The crystals that separated on inducement were filtered and washed with ether; wt 0.063 g; mp 130°–132° C.;

Mass spectrum (CI) 475 (M$^+$).

Analysis calculated for $C_{23}H_{28}Cl_2N_6O$: C, 58.11; H, 5.94; N, 17.68. Found: C, 58.39; H, 5.99; N, 17.53.

EXAMPLE 60

2-Cyclohexylamino-6-(2,6-dichlorophenyl)-8-methyl-8H-pyrido[2,3-d]pyrimidin-7-one A mixture of 0.100 g (0.26 mmol) of 6-(2,6-dichlorophenyl)-2-methanesulfonyl-8-methyl-8H-pyrido[2,3-d]pyrimidin-7-one of Example 39 and 0.300 g (3.00 mmol) of cyclohexylamine was heated to the boiling point (134° C.). The resulting solution was heated at reflux for 2 minutes. Most of the excess amine was evaporated at reduced pressure. The remaining gum was dissolved in 2 mL of ethyl acetate hot. Petroleum ether (2 mL) was added, and the crystals that separated from the cooled solution were filtered and washed with water; wt 0.090 g. Recrystallization from ethyl acetate gave pure crystalline product; 0.048 g; mp 242°–244° C.

Mass spectrum (CI) 403 (M$^+$).

Analysis calculated for $C_{20}H_{20}Cl_2N_4O$: C, 59.56; H, 5.00; N, 13.89. Found: C, 59.92; H, 5.03; N, 13.86.

EXAMPLE 61

6-[6-(2,6-Dichlorophenyl)-8-methyl-7-oxo-7,8-dihydro-pyrido[2,3-d]pyrimidin-2-ylamino]-hexanoic acid, tert-butyl ester A mixture of 0.152 g (0.40 mmol) of 6-(2,6-dichlorophenyl)-2-methanesulfonyl-8-methyl-8H-pyrido[2,3-d]pyrimidin-7-one of Example 39 and 0.750 g (4.00 mmol) of 5-aminohexanoic acid, tert-butyl ester was heated with stirring in a 120° C. oil bath to complete solution. After 10 minutes, the solution was cooled to room temperature and 20 mL of 10% potassium bisulfate solution was added with ice chips present. The separated gum was extracted into 30 mL of ether. The organic phase was washed with 3×5 mL of water, dried (magnesium sulfate), filtered, and concentrated to 2 mL volume. The crystals that separated on inducement were filtered and washed with 1 mL of ether; wt 0.150 g; mp 70°–75° C.

Mass spectrum (CI) 491 (M$^+$).

Analysis calculated for $C_{24}H_{28}Cl_2N_4O_3 \cdot 0.2\ H_2O$: C, 58.22; H, 5.78; N, 11.32. Found: C, 57.84; H, 5.71; N, 11.04.

EXAMPLE 62

6-[6-(2,6-Dichlorophenyl)-8-methyl-7-oxo-7,8-dihydro-pyrido[2,3-d]pyrimidin-2-ylamino]-hexanoic acid A solution of 0.095 g (0.19 mmol) of 6-[6-(2,6-dichlorophenyl)-8-methyl-7-oxo-7,8-dihydropyrido[2,3-d]pyrimidin-2-ylamino]-hexanoic acid, tert-butyl ester of Example 61 in 0.75 mL of trifluoroacetic acid at 25° C. was allowed to stand for 1 hour. Most of the trifluoroacetic acid was evaporated. The remaining gum was triturated with 2 mL of water and decanted. Methanol (1 mL) was added to dissolve most of the gum when well-defined crystals developed. Water (1 mL) was added, and the solid was filtered and dried; wt 0.100 g; mp 240°–242° C.

Mass spectrum (CI) 435 (M$^+$).

Analysis calculated for $C_{20}H_{20}Cl_2N_4O_3 \cdot CF_3CO_2H \cdot 0.75\ CH_3OH$: C, 47.65; H, 4.22; N, 9.77. Found: C, 47.38; H, 4.28; N, 9.72.

EXAMPLE 63

6-(2,6-Dichlorophenyl)-8-methyl-3-p-tolylamino-8H-pyrido[2,3-d]pyrimidin-7-one

A mixture of 0.113 g (0.29 mmol) of 6-(2,6-dichlorophenyl)-2-methanesulfonyl-8-methyl-8H-pyrido[2,3-d]pyrimidin-7-one of Example 39 and 0.50 g (4.70 mmol) of 4-methylaniline was heated, with stirring, in a 180° C. oil bath. The resulting solution was heated for 10 minutes. Much of the excess 4-methylaniline was evaporated at reduced pressure. The remainder was dissolved in 1 mL of ethyl acetate. The crystals that separated from the dark solution were filtered and washed with 2 mL of ethyl acetate and then ether; wt 0.111 g. Recrystallization from ethyl acetate gave pure product; wt 0.050 g; mp 243°–245° C.

Mass spectrum (CI) 411 (M$^+$).

Analysis calculated for $C_{21}H_{16}Cl_2N_4O$: C, 61.33; H, 3.92; N, 13.62.
Found: C, 61.11; H, 4.00; N, 13.41.

EXAMPLE 64

6-(2,6-Dichlorophenyl)-2-(4-methoxyphenylamino)-8-methyl-8H-pyrido[2,3-d]pyrimidin-7-one A mixture of 0.113 g (0.29 mmol) of 6-(2,6-dichlorophenyl)-2-methanesulfonyl-8-methyl-8H-pyrido[2,3-d]pyrimidin-7-one of Example 39 and 0.50 g (4.10 mmol) of 4-methoxyaniline was heated, with stirring, in a 180° C. oil bath. The resulting solution was heated for 10 minutes. Much of the excess aniline was evaporated at reduced pressure. The remainder was dissolved in 2 mL of ethyl acetate. The crystals that separated from the dark solution were filtered and washed with 2 mL of ethyl acetate, wt 0.102 g.

Recrystallization from ethyl acetate gave pure product; wt 0.047 g; mp 221°–223° C.

Mass spectrum (CI) 427 (M$^+$).

Analysis calculated for $C_{21}H_{16}Cl_2N_4O_2$: C, 59.03; H, 3.77; N, 13.11.
Found: C, 59.19; H, 3.84; N, 13.07.

EXAMPLE 65

6-(2,6-Dichlorophenyl)-8-ethyl-2-methylsulfanyl-8H-pyrido[2,3-d]pyrimidin-7-ylideneamine A quantity of 20 g of powdered anhydrous potassium carbonate was added to a solution of 4.95 g (0.025 mol) of 4-ethylamino-2-methylsulfanylpyrimidine-5-carbaldehyde and 5.25 g (0.028 mol) of 2,6-dichloro-phenylacetonitrile in 50 mL of dimethylformamide. The mixture was heated with stirring in a 130° C. oil bath (pot T=ca. 120° C.) for 16 hours. The mixture was cooled and filtered. The cake was washed with 30 mL of dimethylformamide. Water was added to the filtrate until slightly turbid. The crystals that separated on inducement were filtered, washed with 20 mL of 50% dimethylformamide/water, and then 20 mL of water, and dried; wt 4.30 g, mp 217°–219° C.

Mass spectrum (CI) 365 (M$^+$).

EXAMPLE 66

N-[6-(2,6-Dichlorophenyl)-8-ethyl-2-methylsulfanyl-8H-pyrido[2,3-d]pyrimidin-7-ylidene]-acetamide A mixture of 2.70 g (7.40 mmol) of 6-(2,6-dichlorophenyl)-8-ethyl-2-methylsulfanyl-8H-pyrido[2,3-d]pyrimidin-7-ylideneamine of Example 65 and 15 mL of acetic anhydride was heated with stirring to the boiling point. The resulting solution was heated at reflux for 5 minutes and concentrated at reduced pressure to ca. 8 mL volume. The solution was cooled and ether (8 mL) was added. The well-defined crystals that separated were filtered and washed with 5 mL of ether and 10 mL of petroleum ether; wt 2.68 g; mp 175°–177° C.

Mass spectrum (CI) 407 (M$^+$).

EXAMPLE 67

6-(2,6-Dichlorophenyl)-8-ethyl-2-methylsulfanyl-8H-pyrido[2,3-d]pyrimidin-7-one

A quantity of 2.40 g (5.90 mmol) of N-[6-(2,6-dichlorophenyl)-8-ethyl-2-methylsulfanyl-8H-pyrido[2,3-d]pyrimidin-7-ylidene]-acetamide of Example 66 was dissolved in 35 mL of 6N hydrochloric acid at 25° C. The solution was heated with stirring to the boiling point. After 1 minute, crystals of product separated. After another 5 minutes at the boiling point, the mixture was cooled, filtered, and the cake was washed successively with 5 mL of 6N hydrochloric acid, 15 mL of water, 5 mL of 2-propanol, and 5 mL of ether; wt 2.11 g (98%). Pure product was isolated using silica gel chromatography eluting with 50% chloroform/ethyl acetate; mp 233°–236° C.

Mass spectrum (CI) 366 (M$^+$).

Analysis calculated for $C_{16}H_{13}Cl_2N_3OS \cdot 0.1\ C_4H_8O_2 \cdot 0.25\ H_2O$: C, 51.89; H, 3.80; N, 11.07.
Found: C, 51.89; H, 3.58; N, 10.99.

EXAMPLE 68

6-(2,6-Dichlorophenyl)-8-ethyl-2-methanesulfonyl-8H-pyrido[2,3-d]pyrimidin-7-one A solution of 0.66 g (1.80 mmol) of 6-(2,6-dichlorophenyl)-8-ethyl-2-methylsulfanyl-8H-pyrido[2,3-d]

pyrimidin-7-one of Example 67 in 50 mL of chloroform was treated with stirring with 1.50 g (4.32 mmol) of 50% to 60% m-chloroperbenzoic acid (assuming 50% of peracid was present). The solution was allowed to stand at room temperature for 16 hours. A quantity of 0.50 g (6.80 mmol) of dimethylsulfoxide was added to reduce excess peracid. After 15 minutes, the solution was washed with 2×30 mL of saturated sodium bicarbonate solution and then with 30 mL of water. The chloroform solution was dried over anhydrous sodium sulfate, filtered, and concentrated to 10 mL volume. Petroleum ether was added until slightly turbid. The separated crystals were filtered and washed with ether; wt 0.401 g; mp 214°–216° C.
Mass spectrum (CI) 398 (M$^+$).
Analysis calculated for $C_{16}H_{13}Cl_2N_3O_3S.0.25\ H_2O$: C, 47.70; H, 3.38; N, 10.43.
Found: C, 47.41; H, 3.17; N, 10.23.

EXAMPLE 69

6-(2,6-Dichlorophenyl)-8-ethyl-2-phenylamino-8H-pyrido[2,3-d]pyrimidin-7-one

A mixture of 0.134 g (0.33 mmol) of 6-(2,6-dichlorophenyl)-8-ethyl-2-methanesulfonyl-8H-pyrido[2,3-d]pyrimidin-7-one of Example 68 and 0.500 g (5.40 mmol) of aniline was heated with stirring in a 195° C. oil bath to reflux. The resulting solution was maintained at reflux for 5 minutes. Most of the excess aniline was evaporated at reduced pressure. The residual gum was dissolved in 15 mL of ethyl acetate. After filtration of a relatively small amount of insoluble material, the solution was filtered through a layer of silica gel to remove violet color. The filtrate was concentrated to 2 mL volume. Petroleum ether was added until slight turbidity. The crystals that separated on inducement were filtered and washed with 50% ether/petroleum ether; wt 0.068 g; mp 223°–225° C.
Mass spectrum (CI) 411 (M$^+$).
Analysis calculated for $C_{21}H_{16}Cl_2N_4O.0.25\ C_4H_8O_2$: C, 60.98; H, 4.19; N, 12.93.
Found: C, 61.19; H, 4.29; N, 12.57.

EXAMPLE 70

6-(2,6-Dichlorophenyl)-8-ethyl-2-[3-(4-methyl-piperazin-1-yl)-propylamino]-8H-pyrido[2,3-d]pyrimidin-7-one A mixture of 0.150 g (0.41 mmol) of 6-(2,6-dichlorophenyl)-8-ethyl-2-methylsulfanyl-8H-pyrido[2,3-d]pyrimidin-7-one of Example 67 and 0.500 g (3.20 mmol) of 1-(3-aminopropyl)-4-methylpiperazine was heated in a 180° C. oil bath. The resulting solution was heated for 0.5 hour. Most of the excess amine was evaporated at reduced pressure. The remaining gum was triturated with 2 mL of water and decanted. The gum was dissolved in 15 mL of ether. The solution was washed with 3×5 mL of water, dried (sodium sulfate), filtered, and concentrated to 2 mL volume. Petroleum ether was added until slight turbidity. The crystals that separated on inducement were filtered and washed with 2 mL of 75% ether/petroleum ether; wt 0.90 g; mp 126°–128° C.
Mass spectrum (CI) 475 (M$^+$).
Analysis calculated for $C_{23}H_{28}Cl_2N_6O.0.4\ H_2O$: C, 57.24; H, 6.01; N, 17.42.
Found: C, 57.33; H, 6.04; N, 17.07.

EXAMPLE 71

6-(2,6-Dichlorophenyl)-2-(2-methoxyphenylamino)-8-methyl-8H-pyrido[2,3-d]pyrimidin-7-one A mixture of 0.113 g (0.29 mmol) of 6-(2,6-dichlorophenyl)-2-methanesulfonyl-8-methyl-8H-pyrido[2,3-d]pyrimidin-7-one of Example 39 and 0.50 g (4.10 mmol) of 2-methoxyaniline was heated, with stirring, in a 175° C. oil bath. The resulting solution was heated for 5 minutes and cooled to room temperature. Ether (2 mL) was added. The crystals that developed were filtered and washed with 1 mL of ether; wt 0.070 g. The solid was purified to remove dark colors by silica gel chromatography, eluting with chloroform. Recrystallization from ether gave pure product; wt 0.029 g; mp 200°–201° C.
Mass spectrum (CI) 427 (M$^+$).
Analysis calculated for $C_{21}H_{16}Cl_2N_4O_2$: C, 59.03; H, 3.77; N, 13.11.
Found: C, 59.09; H, 3.87; N, 13.02.

EXAMPLE 72

6-(2,6-Dichlorophenyl)-2-(3-methoxyphenylamino)-8-methyl-8H-pyrido[2,3-d]pyrimidin-7-one A mixture of 0.113 g (0.29 mmol) of 6-(2,6-dichlorophenyl)-2-methanesulfonyl-8-methyl-8H-pyrido[2,3-d]pyrimidin-7-one of Example 39 and 0.50 g (4.10 mmol) of 3-methoxyaniline was heated, with stirring, in a 175° C. oil bath. The resulting solution was heated for 5 minutes and cooled to room temperature. Ether (2 mL) was added. The crystals that developed were filtered and washed with 2 mL of ether; wt 0.083 g. The solid was purified to remove dark colors by silica gel chromatography, eluting with chloroform. Recrystallization from ether gave pure product; wt 0.037 g; mp 203°–204° C.
Mass spectrum (CI) 427 (M$^+$).
Analysis calculated for $C_{21}H_{16}Cl_2N_4O_2.0.5\ H_2O$: C, 57.81; H, 3.93; N, 12.84.
Found: C, 57.98; H, 3.82; N, 12.71.

EXAMPLE 73

6-(2,6-Dichlorophenyl)-2-(4-methoxy-3-methylphenylamino)-8-methyl-8H-pyrido[2,3-d]pyrimidin-7-one A mixture of 0.113 g (0.29 mmol) of 6-(2,6-dichlorophenyl)-2-methanesulfonyl-8-methyl-8H-pyrido[2,3-d]pyrimidin-7-one of Example 39 and 0.40 g (2.90 mmol) of 3-methyl-4-methoxyaniline was heated, with stirring, in a 165° C. oil bath. The resulting solution was heated for 5 minutes and cooled to room temperature. Ether (1 mL) was added. The crystals that developed were filtered and washed with 2 mL of ether; wt 0.109 g. The solid was purified to remove dark colors by silica gel chromatography, eluting with chloroform and then ethyl acetate. The ethyl acetate eluent was concentrated to 3 mL volume. On cooling, pure crystals of product separated; wt 0.060 g; mp 218°–220° C.
Mass spectrum (CI) 441 (M$^+$).
Analysis calculated for $C_{22}H_{18}Cl_2N_4O_2$: C, 59.88; H, 4.11; N, 12.70.
Found: C, 59.88; H, 4.14; N, 12.57.

EXAMPLE 74

6-(2,6-Dichlorophenyl)-8-ethyl-2-(4-methoxyphenylamino)-8H-pyrido[2,3-d]pyrimidin-7-one A solution of 0.100 g (0.25 mmol) of 6-(2,6-dichlorophenyl)-8-ethyl-2-methanesulfonyl-8H-pyrido[2,3-d]pyrimidin-7-one of Example 68 and 0.061 g (0.50 mmol) of 4-methoxyaniline in 0.5 mL of dimethylformamide was heated at reflux for 10 minutes. Three drops of water were added. Crystals separated on inducement. An additional 3 drops of water were added to precipitate additional tacky solid. After decantation, the solid was triturated with 0.5 mL of ethyl acetate and 0.5 mL of petroleum ether. The solids were filtered and washed with 50% ethyl acetate/petroleum ether and dried; wt 0.080 g. Purification was effected by filtering an ethyl acetate solution through a layer of silica gel. Concentration of the filtrate to 1 mL volume yielded pure crystalline product; wt 0.033 g; mp 213°–215° C.
Mass spectrum (CI) 441 (M$^+$).
Analysis calculated for $C_{22}H_{18}Cl_2N_4O_2$: C, 59.88; H, 4.11; N, 12.70.
Found: C, 59.52; H, 4.17; N, 12.56.

EXAMPLE 75

6-(2,6-Dichlorophenyl)-8-ethyl-2-(4-hydroxyphenylamino)-8H-pyrido[2,3-d]pyrimidin-7-one A mixture of 0.048 g (0.11 mmol) of 6-(2,6-dichlorophenyl)-8-ethyl-2-(4-methoxyphenylamino)-8H-pyrido[2,3-d]pyrimidin-7-one of Example 74 and 15 mL of concentrated (48%) hydrobromic acid was heated, with stirring, at reflux for 3 hours. The resulting solution yielded crystals on cooling; wt 0.033 g; mp 255°–258° C.
Mass spectrum (CI) 427 (M$^+$).
Analysis calculated for $C_{21}H_{16}Cl_2N_4O_2 \cdot HBr \cdot H_2O$: C, 47.93; H, 3.64; N, 10.65.
Found: C, 47.78; H, 3.29; N, 10.46.

EXAMPLE 76

6-(2,6-Dichlorophenyl)-2-(4-ethoxyphenylamino)-8-ethyl-8H-pyrido[2,3-d]pyrimidin-7-one A mixture of 0.150 g (0.38 mmol) of 6-(2,6-dichlorophenyl)-8-ethyl-2-methanesulfonyl-8H-pyrido[2,3-d]pyrimidin-7-one of Example 68 and 0.500 g (3.60 mmol) of 4-ethoxyaniline was fused in a 160° C. oil bath for 10 minutes. The dark violet melt was cooled and dissolved in 1 mL of warm glacial acetic acid. This solution was diluted to 10 mL volume with water to precipitate a solid. The solid was filtered, washed well with water, and dried; wt 0.140 g. Purification was effected by filtration of an ethyl acetate solution through a layer of silica gel and washing the silica gel with ethyl acetate. The filtrate was concentrated to 2 mL volume and 2 mL of petroleum ether was added. The crystals that separated on inducement were filtered and washed with ether; wt 0.094 g; mp 192°–194° C.
Mass spectrum (CI) 455 (M$^+$).
Analysis calculated for $C_{23}H_{20}Cl_2N_4O_2$: C, 60.67; H, 4.43; N, 12.30.
Found: C, 60.62; H, 4.53; N, 12.11.

EXAMPLE 77

6-(2,6-Dichlorophenyl)-2-(3,4-dimethoxyphenylamino)-8-ethyl-8H-pyrido[2,3-d]pyrimidin-7-one A mixture of 0.150 g (0.38 mmol) of 6-(2,6-dichlorophenyl)-8-ethyl-2-methanesulfonyl-8H-pyrido[2,3-d]pyrimidin-7-one of Example 68 and 0.500 g (3.30 mmol) of 3,4-dimethoxyaniline was heated in a 160° C. oil bath for 5 minutes. The dark blue solution was cooled and dissolved in 2 mL of warm glacial acetic acid. This solution was diluted to 10 mL volume with water to precipitate a solid. The solid was filtered, washed well with water, and dried; wt 0.200 g. Purification was effected by filtration of an ethyl acetate (25 mL) solution through a layer of silica gel and washing the silica gel with ethyl acetate. The filtrate was concentrated to 3 mL volume. The crystals that separated on inducement were filtered and washed with 1 mL of ethyl acetate and then 1 mL of ether; wt 0.116 g; mp 221°–223° C.
Mass spectrum (CI) 471 (M$^+$).
Analysis calculated for $C_{23}H_{20}Cl_2N_4O_3$: C, 58.61; H, 4.28; N, 11.89.
Found: C, 58.31; H, 4.31; N, 11.71.

EXAMPLE 78

6-(2,6-Dichlorophenyl)-8-ethyl-2-(3,4,5-trimethoxyphenylamino)-8H-pyrido[2,3-d]pyrimidin-7-one A mixture of 0.150 g (0.38 mmol) of 6-(2,6-dichlorophenyl)-8-ethyl-2-methanesulfonyl-8H-pyrido[2,3-d]pyrimidin-7-one of Example 68 and 0.500 g (2.70 mmol) of 3,4,5-trimethoxyaniline was heated in a 160° C. oil bath for 5 minutes. The dark solution was cooled and dissolved in 2 mL of warm glacial acetic acid. This solution was diluted to 15 mL volume with water to precipitate a violet solid. The solid was filtered, washed well with water, and dried; wt 0.140 g. Purification was effected by filtration of an ethyl acetate (30 mL) solution through a layer of silica gel and washing the silica gel with ethyl acetate. The filtrate was concentrated to 3 mL volume. The crystals that separated on inducement were filtered and washed with 1 mL of ethyl acetate and 1 mL of ether; wt 0.054 g; mp 275°–278° C.
Mass spectrum (CI) 501 (M$^+$).
Analysis calculated for $C_{24}H_{22}Cl_2N_4O_4$: C, 57.50; H, 4.42; N, 11.17.
Found: C, 57.41; H, 4.51; N, 10.98.

EXAMPLE 79

6-(2,6-Dichlorophenyl)-8-methyl-2-(pyridin-3-ylamino)-8H-pyrido[2,3-d]pyrimidin-7-one A mixture of 0.165 g (0.47 mmol) of 6-(2,6-dichlorophenyl)-8-methyl-2-methylsulfanyl-8H-pyrido[2,3-d]pyrimidin-7-one of Example 37, 0.500 g (5.30 mmol) of 3-aminopyridine base, and 0.066 g (0.50 mmol) of 3-aminopyridine hydrochloride was heated with stirring in a 210° C. oil bath for 1 hour. Water (5 mL) was added to the cooled reaction mixture to precipitate a solid. The solid was filtered, washed well with water, and dried; wt 0.147 g. Purification was effected by silica gel chromatography by eluting with chloroform and then ethyl acetate. The ethyl acetate eluent containing the pure product was concentrated to 2 mL volume. The crystals that separated on inducement were filtered and washed with 0.5 mL of ethyl acetate and 1 mL of ether; wt 0.810 g; mp 247°–248° C.
Mass spectrum (CI) 398 (M$^+$).
Analysis calculated for $C_{19}H_{13}Cl_2N_5O$: C, 57.30; H, 3.29; N, 17.59.
Found: C, 57.33; H, 3.38; N, 17.43.

EXAMPLE 80

6-(2,6-Dichlorophenyl)-2-[4-(2-diethylaminoethoxy)-phenylamino]-8-methyl-8H-pyrido[2,3-d]pyrimidin-7-one A mixture of 0.155 g (0.40 mmol) of 6-(2,6-dichlorophenyl)-8-methyl-2-methylsulfanyl-8H-pyrido[2,3- d]pyrimidin-7-one of Example 37, 0.167 g (0.80 mmol) of 4-(2-diethylaminoethoxy)aniline and 1 mL of (2-methoxyethyl)ether (bp 162° C.) was heated with stirring in a 150° C. oil bath. All solid gradually dissolved over a period of 10 minutes. The solution was heated another 10 minutes and cooled to 100° C. Water was added dropwise until slight turbidity. The crystals that separated on inducement were filtered, washed with 0.5 mL of ether and 2 mL of water, and dried; wt 0.105 g. Purification was effected by chromatography eluting with chloroform, then ethyl acetate and finally 10% methanol/chloroform to obtain fraction with pure product. The eluent was evaporated to dryness. The remaining amorphous solid was dissolved in 1 mL of warm ethyl acetate. The crystals that separated on inducement were filtered and washed sparingly with ethyl acetate and ether; wt 0.042 g; mp 141°–143° C.

Mass spectrum (CI) 512 (M$^+$).

Analysis calculated for $C_{26}H_{27}Cl_2N_5O_2$: C, 60.94; H, 5.31; N, 13.67.

Found: C, 60.96; H, 5.36; N, 13.52.

EXAMPLE 81

6-(2,6-Dichlorophenyl)-8-methyl-2-[5-(4-methylpiperazin-1-yl)-pentylamino]-8H-pyrido[2,3-d]pyrimidin-7-one A mixture of 0.165 g (0.47 mmol) of 6-(2,6-dichlorophenyl)-8-methyl-2-methylsulfanyl-8H-pyrido[2,3-d]pyrimidin-7-one of Example 37 and 0.50 g (2.70 mmol) of 1-(5-aminopentyl)-4-methylpiperazine was heated with stirring in a 180° C. to 185° C. oil bath. After 2 minutes, solution was complete. After 0.5 hour, the solution was cooled to room temperature, and 5 mL of water was added to precipitate a taffy-like gum. Decanted and triturated gum again with 5 mL of water. Decanted and took up gum into 35 mL of ether. The ether solution was washed with 2×50 mL of water, dried (potassium carbonate), and concentrated to 5 mL volume. Petroleum ether was added to slight turbidity. The crystals that separated on inducement were filtered and washed with 80% ether/petroleum ether; wt 0.060 g; mp 110°–112° C.;

Mass spectrum (CI) 489 (M$^+$).

Analysis calculated for $C_{24}H_{30}Cl_2N_6O$: C, 58.90; H, 6.18; N, 17.17.

Found: C, 58.75; H, 6.14; N, 16.96.

EXAMPLE 82

6-(2,6-Dichlorophenyl)-2-(3-hydroxymethylphenylamino)-8-methyl-8H-pyrido[2,3-d]pyrimidin-7-one A mixture of 0.155 g (0.40 mmol) of 6-(2,6-dichlorophenyl)-2-methanesulfonyl-8-methyl-8H-pyrido[2,3-d]pyrimidin-7-one of Example 39 and 0.500 g (4.10 mmol) of 3-(hydroxymethyl)aniline was heated in a 180° C. oil bath for 10 minutes. At ca. 120° C., 2 mL of glacial acetic acid were added to dissolve the gum. Water (20 mL) was added to precipitate a solid. The mixture was filtered. The cake was washed well with water and dried; wt 0.130 g. Purification was effected by silica gel chromatography eluting with chloroform and then with ethyl acetate to obtain the fraction containing the pure product. The ethyl acetate eluent was concentrated to 1 mL volume. The crystals that separated one inducement were filtered and washed with 0.5 mL of ethyl acetate and then 1 mL of ether; wt 0.059 g; mp 215°–217° C.

Mass spectrum (CI) 427 (M$^+$).

Analysis calculated for $C_{21}H_{16}Cl_2N_4O_2$: C, 59.03; H, 3.77; N, 13.11.

Found: C, 59.14; H, 3.91; N, 12.78.

EXAMPLE 83

6-(2,6-Dichlorophenyl)-2-(3,5-dimethoxyphenylamino)-8-methyl-8H-pyrido[2,3-d]pyrimidin-7-one A mixture of 0.155 g (0.40 mmol) of 6-(2,6-dichlorophenyl)-2-methanesulfonyl-8-methyl-8H-pyrido[2,3-d]pyrimidin-7-one of Example 39 and 0.400 g (2.60 mmol) of 3,5-dimethoxyaniline was heated in a 160° C. oil bath for 5 minutes. At ca. 100° C., 1 mL of glacial acetic acid was added to the melt to dissolve. Water (10 mL) was added to precipitate a gum. Decanted and dissolved gum in 35 mL of methylene chloride. The solution was washed with 2×20 mL of water, dried over magnesium sulfate, charcoaled, filtered, and concentrated. The remaining gum was purified silica gel chromatography eluting with chloroform and then with 2:1 hexane:ethyl acetate to obtain the fraction containing the pure product. The eluent was evaporated to near dryness when crystals separated. The crystals were filtered and washed with 0.5 mL of ether; wt 0.059 g; mp 228°–230° C.

Mass spectrum (CI) 457 (M$^+$).

Analysis calculated for $C_{22}H_{18}Cl_2N_4O_3$: C, 57.78; H, 3.97; N, 12.25.

Found: C, 57.93; H, 4.07; N, 12.16.

EXAMPLE 84

{4-[6-(2,6-Dichlorophenyl)-8-methyl-7-oxo-7,8-dihydro-pyrido[2,3-d]pyrimidin-2-ylamino]phenyl}-acetic acid, methyl ester A mixture of 0.226 g (0.58 mmol) of 6-(2,6-dichlorophenyl)-2-methanesulfonyl-8-methyl-8H-pyrido[2,3-d]pyrimidin-7-one of Example 39 and 0.40 g (2.80 mmol) of 4-aminophenylacetic acid, methyl ester base was heated in a 160° C. to 165° C. oil bath. The resulting solution was heated for 10 minutes and cooled to room temperature. The solution was treated with 1 mL of glacial acetic acid to dissolve. Water (10 mL) was added to precipitate a gum. The mixture was decanted, and the remaining gum was dissolved in 20 mL of chloroform. The chloroform solution was washed with 25 mL of water, dried (magnesium sulfate), filtered, and concentrated. Purification was effected by silica gel chromatography eluting with chloroform and then with 50% hexane/ethyl acetate to obtain the fraction containing pure product. The eluent was concentrated to dryness to obtain a solid; wt 0.141 g.

Recrystallization from ethyl acetate gave crystals; wt 0.054 g; mp 224°–226° C.

Mass spectrum (CI) 469 (M$^+$).

Analysis calculated for $C_{23}H_{18}Cl_2N_4O_3$: C, 58.86; H, 3.87; N, 11.94.

Found: C, 59.10; H, 3.94; N, 11.85.

EXAMPLE 85

6-(2,6-Dichlorophenyl)-2-(6-methoxypyridin-3-ylamino)-8-methyl-8H-pyrido[2,3-d]pyrimidin-7-one A mixture of 0.155 g (0.40 mmol) of 6-(2,6-dichlorophenyl)-2-methanesulfonyl-8-methyl-8H-pyrido[2,3-d]pyrimidin-7-one of Example 39 and 0.50 g (4.00 mmol)

of 5-amino-2-methoxypyridine was heated, with stirring, in a 160° C. oil bath. The resulting solution was heated for 10 minutes and cooled to room temperature. Water (10 mL) was added to precipitate a gum. The mixture was decanted, and the remaining gum was triturated with 5 mL of water. The brown solid that developed was filtered, washed well with water, and dried; wt 0.135 g. Purification was effected by silica gel chromatography eluting with chloroform and then with ethyl acetate to obtain the fraction containing pure product. The eluent was concentrated to 2 mL volume. The crystals that separated on inducement were filtered and washed with 0.2 mL of ethyl acetate and then 0.5 mL of ether; wt 0.045 g; mp 233°–235° C.

Mass spectrum (CI) 428 (M$^+$).

Analysis calculated for $C_{20}H_{15}Cl_2N_5O_2$: C, 56.09; H, 3.53; N, 16.35.

Found: C, 56.07; H, 3.53; N, 16.06.

EXAMPLE 86

{4-[6-(2,6-Dichlorophenyl)-8-methyl-7-oxo-7,8-dihydro-pyrido[2,3-d]pyrimidin-2-ylamino]phenyl}-acetic acid A quantity of 0.065 g (0.14 mmol) of {4-[6-(2,6-dichlorophenyl)-8-methyl-7-oxo-7,8-dihydro-pyrido[2,3-d]pyrimidin-2-ylamino]phenyl}-acetic acid, methyl ester of Example 84 was dissolved in 25 mL of hot methanol with stirring. At the boiling point, 1 mL of 2N sodium hydroxide was added. After 1 hour reflux, the solution was concentrated to 5 mL volume (solid was out of solution). Water (10 mL) was added to give a complete solution. Glacial acetic acid (0.25 mL) was added to precipitate the solid free acid product. The solid was filtered, washed well with water, and dried; wt 0.060 g. Purification was accomplished by dissolution in 60 mL of 50% methanol/methylene chloride. Traces of solids were filtered, and the filtrate was concentrated with stirring to 2 mL volume. The separated solid was filtered and washed with 0.5 mL of methanol and ether; wt 0.050 g; mp 286°–290° C.

Mass spectrum (CI) 455 (M$^+$).

Analysis calculated for $C_{22}H_{16}Cl_2N_4O_3$: C, 58.04; H, 3.54; N, 12.31.

Found: C, 58.28; H, 3.59; N, 12.19.

EXAMPLE 87

6-(2,6-Dichlorophenyl)-2-(3-hydroxyphenylamino)-8-methyl-8H-pyrido[2,3-d]pyrimidin-7-one A mixture of 0.155 g (0.40 mmol) of 6-(2,6-dichlorophenyl)-2-methanesulfonyl-8-methyl-8H-pyrido[2,3-d]pyrimidin-7-one of Example 39 and 0.50 g (4.60 mmol) of 3-aminophenol was fused in a 160° C. oil bath for 10 minutes. The melt was cooled to ca. 100° C., and 5 mL of glacial acetic acid was added to dissolve. Water was added until slight turbidity developed. The crystals that separated on inducement were filtered, washed well with water, and dried; wt 0.104 g. Recrystallization from ethyl acetate/petroleum ether gave pure crystalline product; wt 0.035 g; mp 290°–292° C.

Mass spectrum (CI) 413 (M$^+$).

Analysis calculated for $C_{20}H_{14}Cl_2N_4O_2$.0.25 $H_2O$: C, 57.50; H, 3.50; N, 13.41.

Found: C, 57.68; H, 3.50; N, 13.36.

EXAMPLE 88

4-[6-(2,6-Dichlorophenyl)-8-methyl-7-oxo-7,8-dihydro-pyrido[2,3-d]pyrimidin-2-ylamino]-benzoic acid, ethyl ester A mixture of 0.226 g (0.58 mmol) of 6-(2,6-dichlorophenyl)-2-methanesulfonyl-8-methyl-8H-pyrido[2,3-d]pyrimidin-7-one of Example 39 and 0.40 g (2.42 mmol) of 4-aminobenzoic acid, ethyl ester was fused in a 170° C. oil bath to give a clear melt. After 15 minutes, crystals began to separate in the hot melt. The reaction mixture was cooled and triturated with 2 mL of ethyl acetate. Petroleum ether (1 mL) was added. The mixture was filtered, and the cake was washed with 2 mL of ether; wt 0.200 g.

Recrystallization from ethyl acetate gave pure product; wt 0.078 g; mp 278°–280° C.

Mass spectrum (CI) 469 (M$^+$).

Analysis calculated for $C_{23}H_{18}Cl_2N_4O_3$.0.1 $H_2O$: C, 58.63; H, 3.89; N, 11.89.

Found: C, 58.43; H, 4.01; N, 11.61.

EXAMPLE 89

3-[6-(2,6-Dichlorophenyl)-8-methyl-7-oxo-7,8-dihydro-pyrido[2,3-d]pyrimidin-2-ylamino]-benzoic acid, ethyl ester A mixture of 0.226 g (0.58 mmol) of 6-(2,6-dichlorophenyl)-2-methanesulfonyl-8-methyl-8H-pyrido[2,3-d]pyrimidin-7-one of Example 39 and 0.40 g (2.42 mmol) of 3-aminobenzoic acid, ethyl ester was fused in a 170° C. oil bath to give a clear melt. After 6 minutes, the melt was cooled to ca. 100° C. Glacial acetic acid (1 mL) was added to dissolve the melt. Water (5 mL) was added to precipitate a solid. The solid was filtered, washed well with water, and triturated with 2 mL of methanol. The mixture was filtered, and the cake was washed with 1 mL of methanol and then ether; wt 0.194 g. Recrystallization from ethyl acetate gave pure product; wt 0.075 g; mp 238°–240° C.

Mass spectrum (CI) 469 (M$^+$).

Analysis calculated for $C_{23}H_{18}Cl_2N_4O_3$: C, 58.86; H, 3.87; N, 11.94.

Found: C, 58.91; H, 3.96; N, 11.87.

EXAMPLE 90

3-[6-(2,6-Dichlorophenyl)-8-methyl-7-oxo-7,8-dihydro-pyrido[2,3-d]pyrimidin-2-ylamino]-benzoic acid A quantity of 0.065 g (0.139 mmol) of 3-[6-(2,6-dichlorophenyl)-8-methyl-7-oxo-7,8-dihydro-pyrido[2,3-d]pyrimidin-2-ylamino]-benzoic acid, ethyl ester of Example 89 was dissolved in 75 mL of boiling methanol. 2N Sodium hydroxide (2 mL) was added, and the clear solution was maintained at reflux for 2 hours. The solution was concentrated with stirring to ca. 15 mL volume. The turbid solution was filtered hot to remove traces of solid. The filtrate was concentrated to ca. 4 mL volume. Water (5 mL) was added to give a turbid mixture. Glacial acetic acid (1 mL) was added to precipitate a flocculent solid. The solid was filtered, washed well with water, and dried; wt 0.048 g. Purification was accomplished by dissolution in 4 mL of warm dimethylformamide and addition of 20 mL of ether. The crystals that slowly separated from the clear solution were filtered and washed with ether and then water (to remove any traces of sodium acetate); wt 0.025 g; mp >300° C.

Mass spectrum (CI) 441 (M$^+$).

Analysis calculated for $C_{21}H_{14}Cl_2N_4O_3$: C, 57.16; H, 3.20; N, 12.70.

Found: C, 56.88; H, 3.42; N, 12.52.

EXAMPLE 91

4-{4-[6-(2,6-Dichlorophenyl)-8-methyl-7-oxo-7,8-dihydro-pyrido[2,3-d]pyrimidin-2-ylamino]-phenyl}-butyric acid, ethyl ester A mixture of 0.452 g (1.16 mmol) of 6-(2,6-dichlorophenyl)-2-methanesulfonyl-8-methyl-8H-pyrido[2, 3-d]pyrimidin-7-one of Example 39 and 1.00 g (4.83 mmol) of 4-aminophenylbutyric acid, ethyl ester base was heated in a 160° C. to 165° C. oil bath. After 1 minute, solution was complete. After 10 minutes, the reaction was cooled to ca. 100° C., and 2 mL of glacial acetic acid was added to dissolve the viscous material. Water (20 mL) was added to precipitate a gum. The mixture was decanted, and the remaining gum was triturated with 3×10 mL of water. The gum was dissolved in 25 mL of methylene chloride, and the solution was washed with 25 mL of water, dried (magnesium sulfate), filtered, and evaporated. The remaining material was dissolved in 2 mL of hot ethyl acetate. The crystals that separated on inducement were filtered and washed with 2 mL of ether; wt 0.358 g. Further purification by silica gel chromatography was necessary to remove a trace of impurity. A chloroform solution of the compound was placed on a column, and the product was eluted with 50% hexane/ethyl acetate. The eluent was concentrated, and the gum was dissolved in 5 mL of warm ether. Pure crystals separated on seeding; wt 0.256 g; mp 169°–170° C.

Mass spectrum (CI) 511 ($M^+$).

Analysis calculated for $C_{26}H_{24}Cl_2N_4O_3$: C, 61.06; H, 4.73; N, 10.96.

Found: C, 61.19; H, 4.76; N, 10.86.

EXAMPLE 92

4-{4-[6-(2,6-Dichlorophenyl)-8-methyl-7-oxo-7,8-dihydro-pyrido[2,3-d]pyrimidin-2-ylamino]-phenyl}-butyric acid A volume of 5 mL of 2N sodium hydroxide was added to a hot stirred solution of 0.170 g (0.33 mmol) of 4-[4-{6-(2,6-dichlorophenyl)-8-methyl-7-oxo-7,8-dihydro-pyrido[2,3-d]pyrimidin-2-ylamino]-phenyl}-butyric acid, ethyl ester of Example 91. The solution was maintained at reflux for 1 hour. Glacial acetic acid (1 mL) was added, and the reaction solution was evaporated to ca. 25 mL volume. Water (50 mL) was added to precipitate a solid. The mixture was filtered, and the cake was washed well with water and dried; wt 0.130 g. Hydrolysis did not go to completion under these conditions. The product was purified to remove starting ester by silica gel chromatography eluting with 1:20 methanol:chloroform to obtain 55 mg of pure acid; mp 169°–171° C.

Mass spectrum (CI) 483 ($M^+$).

Analysis calculated for $C_{24}H_{20}Cl_2N_4O_3$: C, 59.64; H, 4.17; N, 11.59.

Found: C, 59.77; H, 4.24; N, 11.44.

EXAMPLE 93

(2,6-Dichlorophenyl)-8-ethyl-2-(pyridin-4-ylamino)-8H-pyrido[2,3-d]pyrimidin-7-one A mixture of 0.126 g (0.31 mmol) of 6-(2,6-dichlorophenyl)-2-methanesulfonyl-8-ethyl-8H-pyrido[2,3-d]pyrimidin-7-one, 0.25 mol hydrate, of Example 68 and 0.300 g (3.20 mmol) of 4-aminopyridine was heated, with stirring, in a 150° C. oil bath for 10 minutes. After 3 minutes, crystals had separated. The mixture was cooled, and 1 mL of methanol was added. The solid was filtered, washed with 1 mL of methanol and then ether; wt 0.100 g. The hydrochloride salt was prepared as follows: The above crude base was suspended in 2 mL of methanol. One mL of 2N hydrochloric acid was added, and the mixture was warmed to complete solution. Another 2 mL of 2N hydrochloric acid was added. The crystals that separated on inducement were filtered and washed successively with 1 mL of 2N hydrochloric acid, 2 mL of ethyl acetate, and then ether; wt 0.110 g. Recrystallization from methanol/ether gave pure crystalline product; wt 0.063 g; mp 325°–330° C.

Mass spectrum (CI) 412 ($M^+$).

Analysis calculated for $C_{20}H_{15}Cl_2N_5O\cdot HCl$: C, 53.53; H, 3.59; N, 15.61.

Found: C, 53.48; H, 3.74; N, 15.38.

EXAMPLE 94

4-Ethylamino-2-methylthio-5-pyrimidinecarboxylate ethyl ester

To a room temperature solution of 4-chloro-2-methylthio-5-pyrimidinecarboxylate ethyl ester (10.00 g, 43.10 mmol) in 150 mL of tetrahydrofuran was added triethylamine (18.5 mL, 133 mmol) followed by 9 mL of a 70% aqueous solution of ethylamine. The solution was stirred for 30 minutes, then concentrated in vacuo and partitioned between chloroform and saturated aqueous sodium bicarbonate. The organic layer was dried over magnesium sulfate, filtered, and concentrated to provide 9.32 g (90%) of 4-ethylamino-2-methylthio-5-pyrimidinecarboxylate ethyl ester as an oil.

Analysis calculated for $C_{10}H_{15}N_3O_2S$: C, 49.77; H, 6.27; N, 17.41.

Found: C, 49.77; H, 6.24; N, 17.30.

EXAMPLE 95

4-Ethylamino-2-methylthio-5-pyrimidinemethanol

A solution of 4-ethylamino-2-methylthio-5-pyrimidinecarboxylate ethyl ester (8.93 g, 37.1 mmol) in 100 mL of tetrahydrofuran was added dropwise to a room temperature suspension of lithium aluminum hydride (2.30 g, 60.5 mmol) in 100 mL of tetrahydrofuran. After 10 minutes, the reaction was carefully quenched with 4.5 mL of water, 4.5 mL of 15% NaOH, and 16 mL of water, and the mixture was stirred for 1.5 hours. The white precipitate was removed by filtration washing with ethyl acetate. The filtrate was concentrated in vacuo and 1:1 hexane:ethyl acetate was added. The solids were collected to give 6.77 g (92%) of 4-ethylamino-2-methylthio-5-pyrimidinemethanol; mp 152°–156° C.

Analysis calculated for $C_8H_{13}N_3OS$: C, 48.22; H, 6.58; N, 21.09.

Found: C, 48.14; H, 6.61; N, 20.85.

EXAMPLE 96

4-Ethylamino-2-methylthio-5-formylpyrimidine

To 4-ethylamino-2-methylthio-5-pyrimidinemethanol (6.44 g, 32.4 mmol) in 600 mL of chloroform was added manganese oxide (21.0 g, 241 mmol) over 3 minutes. The suspension was stirred at room temperature for 2 hours, and an additional 5.5 g of manganese oxide was added. Stirring was continued for 4.5 hours. The mixture was then filtered through celite washing with chloroform. The filtrate was concentrated in vacuo to give 6.25 g (97%) of 4-ethylamino-2-methylthio-5-formylpyrimidine; mp 58°–61° C.

Analysis calculated for $C_8H_{11}N_3OS$: C, 48.71; H, 5.62; N, 21.30.

Found: C, 48.62; H, 5.60; N, 21.28.

EXAMPLE 97

4-Ethylamino-2-methanesulfinyl-pyrimidine-5-carboxylic acid ethyl ester

To a room temperature solution of 4-ethylamino-2-methylthio-5-pyrimidinecarboxylate ethyl ester (2.011 g, 8.34 mmol) in 70 mL of chloroform was added (±)-trans-2-(phenylsulfonyl)-3-phenyloxaziridine (2.70 g, 10.34 mmol). The solution was stirred at room temperature for 7 hours, then concentrated in vacuo. The residue was purified by flash chromatography eluting with a gradient of ethyl acetate to 3% methanol in ethyl acetate to provide 2.07 g (97%) of 4-ethylamino-2-methanesulfinyl-pyrimidine-5-carboxylic acid ethyl ester; mp 54°–56° C.
Analysis calculated for $C_{10}H_{15}N_3O_3S$: C, 46.68; H, 5.88; N, 16.33.
Found: C, 46.56; H, 5.68; N, 16.23.

EXAMPLE 98

4-Ethylamino-2-phenylamino-pyrimidine-5-carboxylic acid ethyl ester

A solution of 4-ethylamino-2-methanesulfinyl-pyrimidine-5-carboxylic acid ethyl ester (166 mg, 0.65 mmol) in 4 mL of aniline was heated to 110° C. for 30 minutes. The solution was cooled to room temperature and concentrated in vacuo. Flash chromatography eluting with 2:1 hexane:ethyl acetate gave 158 mg (87%) of a white solid, which by NMR was predominately the desired product.

EXAMPLE 99

(4-Ethylamino-2-phenylamino-pyrimidin-5-yl) methanol

A solution of 4-ethylamino-2-phenylamino-pyrimidine-5-carboxylic acid ethyl ester (109 mg, 0.38 mmol) in 6 mL of tetrahydrofuran was added dropwise to a room temperature suspension of lithium aluminum hydride (35 mg, 0.92 mmol) in 5 mL of tetrahydrofuran. After 25 minutes, an additional 30 mg of lithium aluminum hydride was added, and stirring was continued for 30 minutes. The reaction was carefully quenched with 120 μL of water, 200 μL of 15% NaOH, and 300 μL of water. After stirring for 1 hour, the white precipitate was removed by filtration washing with ethyl acetate. The filtrate was concentrated in vacuo, and the crude material was purified by flash chromatography eluting with ethyl acetate to provide 36 mg (39%) of (4-ethylamino-2-phenylamino-pyrimidin-5-yl)methanol; mp 174°–176° C.
Analysis calculated for $C_{13}H_{16}N_4O$: C, 63.92; H, 6.60; N, 22.93.
Found: C, 63.97; H, 6.58; N, 22.79.

EXAMPLE 100

4-Ethylamino-2-phenylamino-pyrimidine-5-carbaldehyde

To a solution of (4-ethylamino-2-phenylamino-pyrimidin-5-yl)methanol (173 mg, 0.71 mmol) in 15 mL of chloroform was added manganese oxide (600 mg, 6.89 mmol). After stirring at room temperature overnight, the mixture was filtered through a pad of Celite, washing with chloroform. The filtrate was concentrated in vacuo to give 170 mg (99%) of 4-ethylamino-2-phenylamino-pyrimidine-5-carbaldehyde; mp 155°–157° C.
Analysis calculated for $C_{13}H_{14}N_4O$: C, 64.45; H, 5.82; N, 23.12.
Found: C, 64.31; H, 6.01; N, 22.98.

EXAMPLE 101

(8-Ethyl-7-imino-6-thiophen-3-yl-7,8-dihydro-pyrido[2,3-d]pyrimidin-2-yl)-phenylamine To a suspension of NaH (60% in mineral oil, 27 mg) in 5 mL of 2-ethoxyethanol was added 3-thiopheneacetonitrile (168 mg, 1.36 mmol). After stirring for 5 minutes at room temperature, 4-ethylamino-2-phenylamino-pyrimidine-5-carbaldehyde (300 mg, 1.24 mmol) was added, and the reaction heated at 120° C. for 2 hours, resulting in a dark brown solution. Upon cooling, the solution was poured into water which caused precipitation. The resulting precipitate was removed by filtration and washed with water. The crude product was purified by flash chromatography, eluting with 5% methanol/methylene chloride, followed by 10% methanol/methylene chloride. Concentration of product fractions yielded 340 mg (78%) of (8-ethyl-7-imino-6-thiophen-3-yl-7,8-dihydro-pyrido[2,3-d]pyrimidin-2-yl)-phenylamine; mp 220°–222° C.
Mass spectrum (CI) 348 (M⁺).
Analysis calculated for $C_{19}H_{17}N_5S$: C, 65.68; H, 4.93; N, 20.16.
Found: C, 64.42; H, 4.86; N, 19.78.

EXAMPLE 102

8-Ethyl-2-phenylamino-6-thiophen-3-yl-8H-pyrido [2,3-d]pyrimidin-7-one

Compound was prepared from (8-ethyl-7-imino-6-thiophen-3-yl-7,8-dihydro-pyrido[2,3-d]pyrimidin-2-yl)-phenylamine following the procedure of Example 116. The product was purified by flash chromatography, eluting with 5% methanol/methylene chloride, followed by 10% methanol/methylene chloride; mp 223°–225° C.
Mass spectrum (CI) 349 (M⁺).
Analysis calculated for $C_{19}H_{16}N_4OS$: C, 65.49; H, 4.63; N, 16.08.
Found: C, 65.33; H, 4.49; N, 15.73.

EXAMPLE 103

(8-Ethyl-7-imino-6-thiophen-2-yl-7,8-dihydro-pyrido[2,3-d]pyrimidin-2-yl)-phenylamine To a suspension of NaH (60% in mineral oil, 27 mg) in 5 mL of 2-ethoxyethanol was added 2-thiopheneacetonitrile (168 mg, 1.36 mmol). After stirring for 5 minutes at room temperature, 4-ethylamino-2-phenylamino-pyrimidine-5-carbaldehyde (300 mg, 1.24 mmol) was added, and the reaction heated at 120° C. for 2 hours, resulting in a dark brown solution. Upon cooling, the solution was poured into water which caused precipitation. The resulting precipitate was removed by filtration and washed with water. The crude product was purified by flash chromatography, eluting with 5% methanol/methylene chloride, followed by 10% methanol/methylene chloride. Concentration of product fractions yielded 370 mg (85%) of (8-ethyl-7-imino-6-thiophen-2-yl-7,8-dihydro-pyrido[2,3-d]pyrimidin-2-yl)-phenylamine; mp 204°–205° C.
Mass spectrum (CI) 348 (M⁺).
Analysis calculated for $C_{19}H_{17}N_5S$: C, 65.68; H, 4.93; N, 20.16.
Found: C, 64.38; H, 4.90; N, 19.78.

EXAMPLE 104

8-Ethyl-2-phenylamino-6-thiophen-2-yl-8H-pyrido [2,3-d]pyrimidin-7-one

Compound was prepared from (8-ethyl-7-imino-6-thiophen-2-yl-7,8-dihydro-pyrido[2,3-d]pyrimidin-2-yl)-phenylamine following the procedure of Example 116. The product was purified by flash chromatography, eluting with 5% methanol/methylene chloride, followed by 10% methanol/methylene chloride; mp 223°–225° C.

Mass spectrum (CI) 349 (M⁺).
Analysis calculated for $C_{19}H_{16}N_4OS$: C, 65.49; H, 4.63; N, 16.08.
Found: C, 65.36; H, 4.78; N, 15.72.

EXAMPLE 105

(6-(2-Bromo-6-chlorophenyl)-8-ethyl-7-imino-7,8-dihydro-pyrido[2,3-d]pyrimidin-2-yl)-phenylamine To a suspension of NaH (60% in mineral oil, 12 mg) in 5 mL of 2-ethoxyethanol was added 2-bromo-6-chlorophenylacetonitrile (286 mg, 1.24 mmol). After stirring for 5 minutes at room temperature, 4-ethylamino-2-phenylamino-pyrimidine-5-carbaldehyde (200 mg, 0.83 mmol) was added, and the reaction heated at 130° C. for 3 hours, resulting in a dark brown solution. Upon cooling, a precipitate formed which was triturated with 20 mL of water. The precipitate was removed by filtration and washed with ether to yield 178 mg of (6-(2-bromo-6-chlorophenyl)-8-ethyl-7-imino-7,8-dihydro-pyrido[2,3-d]pyrimidin-2-yl)-phenylamine.

EXAMPLE 106

6-(2-Bromo-6-chlorophenyl)-8-ethyl-2-phenylamino-8H-pyrido[2,3-d]pyrimidin-7-one (6-(2-Bromo-6-chlorophenyl)-8-ethyl-7-imino-7,8-dihydro-pyrido[2,3-d]pyrimidin-2-yl)-phenylamine (150 mg) was added to 1 mL of acetic anhydride and heated at reflux for 5 minutes. The reaction was cooled and concentrated resulting in an oil which was heated at reflux with 10 mL of 6N HCl for 10 minutes. The reaction was cooled, and 30 mL of water was added causing precipitation. The precipitate was removed by filtration and washed with water. The resulting solid was dried to give 130 mg of 6-(2-bromo-6-chlorophenyl)-8-ethyl-2-phenylamino-8H-pyrido[2,3-d]pyrimidin-7-one; mp softens at 195° C. and melts at 210°–214° C.
Mass spectrum (CI) 457 (M⁺).
Analysis calculated for $C_{21}H_{16}N_4OBrCl·HCl$: C, 51.24; H, 3.48; N, 11.38.
Found: C, 50.58; H, 3.51; N, 11.32.

EXAMPLE 107

[2-Amino-6-(2,6-dichlorophenyl)-7-oxo-7H-pyrido[2,3-d]-pyrimidin-8-yl]-acetic acid To a solution of [2-amino-6-(2,6-dichlorophenyl)-7-oxo-7H-pyrido[2,3-d]pyrimidin-8-yl]-acetic acid tert-butyl ester (157 mg, 0.37 mmol) from Example 36 in 4 mL of methylene chloride was added 2 mL of trifluoroacetic acid. The solution was stirred at room temperature for 5 hours, then concentrated in vacuo. The resultant oil was partitioned between methylene chloride and brine. The aqueous layer was washed with ethyl acetate, and the organic layers were combined, dried over magnesium sulfate, filtered, and concentrated in vacuo to give a gummy solid. Diethyl ether was added, and the resultant precipitate was collected. Hexane was added to the filtrate, and once again the resultant precipitate was collected. The solids were combined and dried in vacuo at 80° C. to give 71 mg (52%) of [2-amino-6-(2,6-dichlorophenyl)-7-oxo-7H-pyrido[2,3-d]pyrimidin-8-yl]-acetic acid that was >97% pure by HPLC; mp 297°–300° C. dec.
Analysis calculated for $C_{15}H_{10}Cl_2N_4O_3$: C, 49.34; H, 2.76; N, 15.34.

Found: C, 46.01; H, 2.77; N, 13.28.

EXAMPLE 108

2-Amino-8-benzyl-6-(2,6-dichlorophenyl)-8H-pyrido[2,3-d]pyrimidin-7-one

To a suspension of NaH (60% in mineral oil, 34 mg) in 6 mL of dimethylformamide was added 2-amino-6-(2,6-dichlorophenyl)-pyrido[2,3-d]pyrimidin-7(8H)-one (200 mg, 0.65 mmol). The mixture was heated to 50° C. resulting in a clear solution. Benzyl bromide (110 µL, 0.92 mmol) was added, and the solution was heated at 50° C. for 5 minutes, stirred at room temperature for 2 hours, then poured onto 40 mL of ice water. The resulting precipitate was removed by filtration and washed with water. The solid was purified by flash chromatography, eluting with ethyl acetate to provide 181 mg of product. A second chromatography eluting with ethyl acetate followed by drying in vacuo gave 110 mg (43%) of 2-amino-8-benzyl-6-(2,6-dichlorophenyl)-8H-pyrido[2,3-d]pyrimidin-7-one; mp 220°–222° C.
Analysis calculated for $C_{20}H_{14}Cl_2N_4O$: C, 60.47; H, 3.55; N, 14.10.
Found: C, 60.55; H, 3.69; N, 13.93.

EXAMPLE 109

2-Amino-8-(3-bromobenzyl)-6-(2,6-dichlorophenyl)-8H-pyrido[2,3-d]pyrimidin-7-one To a suspension of NaH (60% in mineral oil, 38 mg) in 8 mL of dimethylformamide was added 2-amino-6-(2,6-dichlorophenyl)-pyrido[2,3-d]pyrimidin-7(8H)-one (200 mg, 0.65 mmol). The mixture was heated at 50° C. for 20 minutes resulting in a clear solution. The heating mantle was removed, and 3-bromobenzyl bromide (240 µL, 0.96 mmol) was added. After 10 minutes, the reaction mixture was poured onto 30 mL of ice water. The resulting precipitate was removed by filtration and washed with water. The solid was purified by flash chromatography, eluting with 1:1 hexane:ethyl acetate, then dried in vacuo to provide 178 mg (58%) of 2-amino-8-(3-bromobenzyl)-6-(2,6-dichlorophenyl)-8H-pyrido[2,3-d]pyrimidin-7-one; mp softens at 195° C., melts at 215° C.
Analysis calculated for $C_{20}H_{13}BrCl_2N_4O$: C, 50.45; H, 2.75; N, 11.77.
Found: C, 50.82; H, 2.91; N, 11.63.

EXAMPLE 110

4-[2-Amino-6-(2,6-dichlorophenyl)-7-oxo-7H-pyrido[2,3-d]pyrimidin-8-yl-methyl]-benzoic acid methyl ester To a suspension of NaH (60% in mineral oil, 36 mg) in 7 mL of dimethylformamide was added 2-amino-6-(2,6-dichlorophenyl)-pyrido[2,3-d]pyrimidin-7(8H)-one (195 mg, 0.64 mmol). The mixture was heated at 40° C. to 50° C. for 20 minutes, resulting in a clear solution. Methyl 4-(bromomethyl) benzoate (206 mg, 0.90 mmol) was added, and the reaction mixture was heated at 40° C. to 50° C. for 15 minutes, then poured onto 30 mL of ice water. The resulting precipitate was removed by filtration and washed with water. The solid was purified by flash chromatography, eluting with a gradient of 1:1 hexane:ethyl acetate to 1:2 hexane: ethyl acetate, then dried in vacuo to provide 204 mg of 4-[2-amino-6-(2,6-dichlorophenyl)-7-oxo-7H-pyrido[2,3-d]pyrimidin-8-ylmethyl]-benzoic acid methyl ester containing 0.16 equivalents of ethyl acetate; mp 235°–237° C.

Analysis calculated for $C_{22}H_{16}Cl_2N_4O_3 0.16\ C_4H_8O_2$: C, 57.95; H, 3.68; N, 11.93.
Found: C, 57.87; H, 3.74; N, 11.67.

EXAMPLE 111

2-Amino-8-(2,6-dichlorobenzyl)-6-(2,6-dichlorophenyl)-8H-pyrido[2,3-d]pyrimidin-7-one To a suspension of NaH (60% in mineral oil, 36 mg) in 8 mL of dimethylformamide was added 2-amino-6-(2,6-dichlorophenyl)-pyrido[2,3-d]pyrimidin-7(8H)-one (208 mg, 0.68 mmol). The mixture was heated at 70° C. for 10 minutes and then at 50° C. for 30 minutes, resulting in a clear solution. α-Bromo-2,6-dichlorotoluene (215 mg, 0.90 mmol) was added, and the reaction mixture was heated at 50° C. for 25 minutes, then poured onto ice water. The resulting precipitate was removed by filtration and washed with water. The solid was purified by flash chromatography, eluting with 1:1 hexane:ethyl acetate then dried in vacuo to provide 112 mg (35%) of 2-amino-8-(2,6-dichlorobenzyl)-6-(2,6-dichlorophenyl)-8H-pyrido[2,3-d]pyrimidin-7-one; mp 274°–276° C.
Analysis calculated for $C_{20}H_{12}C_{14}N_4O$: C, 51.53; H, 2.59; N, 12.02.
Found: C, 51.92; H, 2.68; N, 11.84.

EXAMPLE 112

2-Amino-6-(2,6-dichlorophenyl)-8-(4-methoxybenzyl)-8H-pyrido[2,3-d]pyrimidin-7-one To a suspension of NaH (60% in mineral oil, 38 mg) in 8 mL of dimethylformamide was added 2-amino-6-(2,6-dichlorophenyl)-pyrido[2,3-d]pyrimidin-7(8H)-one (208 mg, 0.68 mmol). The mixture was heated at 50° C. for 1 hour, resulting in a clear solution. 4-Methoxybenzyl chloride (130 μL, 0.95 mmol) was added, and the reaction mixture was heated at 50° C. for 30 minutes, then poured onto ice water. The resulting precipitate was removed by filtration and washed with water. The solid was purified by flash chromatography, eluting with 1:1 hexane:ethyl acetate, then dried in vacuo to provide 208 (72%) mg of 2-amino-6-(2,6-dichlorophenyl)-8-(4-methoxybenzyl)-8H-pyrido[2,3-d]pyrimidin-7-one; mp 208°–209° C.
Analysis calculated for $C_{21}H_{16}Cl_2N_4O_2$: C, 59.03; H, 3.77; N, 13.11.
Found: C, 59.39; H, 3.92; N, 12.88.

EXAMPLE 113

2-Amino-6-(2,6-dichlorophenyl)-8-pyridin-4-ylmethyl-8H-pyrido[2,3-d]pyrimidin-7-one To a suspension of NaH (60% in mineral oil, 32 mg) in 6 mL of dimethylformamide was added 2-amino-6-(2,6-dichlorophenyl)-pyrido[2,3-d]pyrimidin-7(8H)-one (200 mg, 0.65 mmol) and the mixture heated to 70° C. In a second flask containing triethyl amine (220 μL, 1.59 mmol) in 4 mL of dimethylformamide was added 4-picolyl chloride hydrochloride (137 mg, 0.84 mmol). This dark red mixture was added to the above solution of the sodium salt of 2-amino-6-(2,6-dichlorophenyl)-pyrido[2,3-d]pyrimidin-7(8H)-one. The mixture was heated to 70° C., then cooled to room temperature. The mixture was poured into 20 mL of ice water, and the resulting precipitate was removed by filtration and washed with water. This solid was washed with 10% methanol in ethyl acetate to provide 96 mg of crude product. The filtrate was concentrated to provide an additional 77 mg of crude product. An analytical sample was obtained by purification by flash chromatography, eluting with a gradient of ethyl acetate to 10% methanol in ethyl acetate to provide 2-amino-6-(2,6-dichlorophenyl)-8-pyridin-4-ylmethyl-8H-pyrido[2,3-d]pyrimidin-7-one; mp 268°–270° C. dec.
Analysis calculated for $C_{19}H_{13}Cl_2N_5O$: C, 57.30; H, 3.29; N, 17.59.
Found: C, 57.62; H, 3.57; N, 17.31.

EXAMPLE 114

2-Amino-6-(2,6-dichlorophenyl)-8-(3-phenylpropyl)-8H-pyrido[2,3-d]pyrimidin-7-one To a suspension of NaH (60% in mineral oil, 58 mg) in 10 mL of dimethylformamide was added 2-amino-6-(2,6-dichlorophenyl)-pyrido[2,3-d]pyrimidin-7(8H)-one (320 mg, 1.04 mmol). The mixture was heated to 60° C. resulting in a clear solution. 1-Chloro-3-phenylpropane (260 μL, 1.81 mmol) was added, and the reaction mixture was heated at 60° C. for 35 minutes, then poured onto ice water. The resulting gummy solid was dissolved in ethyl acetate, washed with water, and dried over magnesium sulfate. Filtration, followed by concentration in vacuo, gave an oil that was purified by flash chromatography, eluting with 1:3 hexane:ethyl acetate to provide 345 mg of crude product. Recrystallization from ethyl acetate and hexane followed by drying in vacuo provided 253 mg (57%) of 2-amino-6-(2,6-dichlorophenyl)-8-(3-phenylpropyl)-8H-pyrido[2,3-d]pyrimidin-7-one; mp 161°–163° C.
Analysis calculated for $C_{22}H_{18}Cl_2N_4O$: C, 62.13; H, 4.27; N, 13.17.
Found: C, 62.08; H, 4.37; N, 13.15.

EXAMPLE 115

(8-Ethyl-7-imino-6-phenyl-7,8-dihydro-pyrido[2,3-d]-pyrimidin-2-yl)-2-phenylamine To a suspension of NaH (60% in mineral oil, 8 mg) in 5 mL of 2-ethoxyethanol was added phenylacetonitrile (100 μL, 0.87 mmol). After stirring for 5 minutes at room temperature, 4-ethylamino-2-phenylamino-pyrimidine-5-carbaldehyde (200 mg, 0.83 mmol) was added, and the reaction heated at 90° C. for 24 hours, resulting in a dark brown solution. This was cooled to room temperature and then poured into 20 mL of water. The resulting precipitate was removed by filtration and washed with water. The residue was dried and purified by flash chromatography, eluting with 3% methanol/methylene chloride to provide 145 mg (51%) of (8-ethyl-7-imino-6-phenyl-7,8-dihydropyrido[2,3-d]-pyrimidin-2-yl)-2-phenylamine; mp 196°–197° C.
Mass spectrum (CI) 342 (M⁺).
Analysis calculated for $C_{21}H_{19}N_5$: C, 73.88; H, 5.61; N, 20.51.
Found: C, 73.22; H, 5.59; N, 20.29.

EXAMPLE 116

8-Ethyl-6-phenyl-2-phenylamino-8H-pyrido[2,3-d]-pyrimidin-7-one (8-Ethyl-7-imino-6-phenyl-7,8-dihydro-pyrido[2,3-d] pyrimidin-2-yl)-2-phenylamine (150 mg) was added to 2 mL of acetic anhydride and heated at reflux for 2 minutes. The reaction was cooled and concentrated, resulting in an oil which was heated at reflux with 10 mL of 6N HCl for 10 minutes. The reaction was cooled, and 20 mL of water was added causing precipitation. The precipitate was removed by filtration and washed with water. The resulting solid was dried in a vacuum oven at 45° C. for 2 hours to provide 122 mg (81%) of 8-ethyl-6-phenyl-2-phenylamino-8H-pyrido[2,3-d]pyrimidin-7-one; mp 197°–200° C. dec.
Mass spectrum (CI) 343 (M$^+$).
Analysis calculated for $C_{21}H_{18}N_4O \cdot 0.5$ HCl: C, 69.94; H, 5.17; N, 15.53; Cl, 4.92.
Found: C, 69.30; H, 5.07; N, 15.44; Cl, 5.21.

EXAMPLE 117

(6-(3,5-Dimethylphenyl)-8-ethyl-7-imino-7,8-dihydro-pyrido[2,3-d]pyrimidin-2-yl)-2-phenylamine To a suspension of NaH (60% in mineral oil, 16 mg) in 5 mL of 2-ethoxyethanol was added 3,5-dimethylphenylacetonitrile (126 mg, 0.87 mmol). After stirring for 5 minutes at room temperature, 4-ethylamino-2-phenylamino-pyrimidine-5-carboxaldehyde (200 mg, 0.83 mmol) was added and the reaction heated at 115° C. for 2 hours, resulting in a dark brown solution. Upon cooling, the solution solidified and was triturated with 30 mL of water. The resulting precipitate was removed by filtration and washed with diethyl ether. The residue was dried to provide 232 mg (76%) of (6-(3,5-dimethylphenyl)-8-ethyl-7-imino-7,8-dihydro-pyrido[2,3-d]pyrimidin-2-yl)-2-phenylamine; mp 243°–244° C.
Analysis calculated for $C_{23}H_{23}N_5$: C, 74.77; H, 6.27; N, 18.95.
Found: C, 73.84; H, 6.30; N, 18.72.

EXAMPLE 118

6-(3,5-Dimethylphenyl)-8-ethyl-2-phenylamino-8H-pyrido[2,3-d]pyrimidin-7-one (6-(3,5-Dimethylphenyl)-8-ethyl-7-imino-7,8-dihydro-pyrido[2,3-d]pyrimidin-2-yl)-2-phenylamine (150 mg) was added to 1 mL of acetic anhydride and heated at reflux for 2 minutes. The reaction was cooled and concentrated resulting in an oil which was heated at reflux with 10 mL of 6N HCl for 10 minutes. The reaction was cooled, and 20 mL of water was added causing precipitation. The precipitate was removed by filtration and washed with water. The resulting solid was dried in a vacuum oven at 45° C. for 2 hours to provide 140 mg (93%) of 6-(3,5-dimethylphenyl)-8-ethyl-2-phenylamino-8H-pyrido[2,3-d]pyrimidin-7-one; mp 220°–223° C.
Mass spectrum (CI) 371 (M$^+$).
Analysis calculated for $C_{23}H_{22}N_4O \cdot HCl$: C, 67.89; H, 5.70; N, 13.77.
Found: C, 67.58; H, 5.68; N, 13.59.

EXAMPLE 119

(8-Ethyl-7-imino-6-pyridin-4-yl-7,8-dihydro-pyrido[2,3-d]pyrimidin-2-yl)-2-phenylamine Prepared in 80% yield from 4-pyridylacetonitrile and 4-ethylamino-2-phenylamino-pyrimidine-5-carbaldehyde following the procedure of Example 115.

EXAMPLE 120

8-Ethyl-2-phenylamino-6-pyridin-4-yl-8H-pyrido[2,3-d]-pyrimidin-7-one

Prepared in 60% yield from (8-ethyl-7-imino-6-pyridin-4-yl-7,8-dihydro-pyrido[2,3-d]pyrimidin-2-yl)-2-phenylamine following the procedure of Example 116; mp softens at 230° C.
Mass spectrum (CI) 344 (M$^+$).
Analysis calculated for $C_{20}H_{17}N_5O \cdot HCl$: C, 63.24; H, 4.78; N, 18.44.
Found: C, 63.92; H, 4.70; N, 18.66.

EXAMPLE 121

(8-Ethyl-7-imino-6-naphthalen-2-yl-7,8-dihydro-pyrido[2,3-d]pyrimidin-2-yl)-phenylamine To a suspension of NaH (60% in mineral oil, 27 mg) in 5 mL of 2-ethoxyethanol was added 2-naphthyl-acetonitrile (227 mg, 1.36 mmol). After stirring for 5 minutes at room temperature, 4-ethylamino-2-phenylamino-pyrimidine-5-carbaldehyde (300 mg, 1.24 mmol) was added and the reaction heated at 110° C. for 1 hour, resulting in a dark brown solution. Upon cooling, the solution was poured into 30 mL of water which caused precipitation. The resulting precipitate was removed by filtration and washed with water. The crude product was purified by flash chromatography, eluting with 5% methanol/methylene chloride, followed by 10% methanol/methylene chloride. Concentration of product fractions yielded 400 mg (82%) of yellow solid, (8-ethyl-7-imino-6-naphthalen-2-yl-7,8-dihydro-pyrido[2,3-d]pyrimidin-2-yl)-phenylamine; mp 236°–242° C.
Mass spectrum (CI) 392 (M$^+$).
Analysis calculated for $C_{25}H_{21}N_5$: C, 76.70; H 5.41; N, 17.89.
Found: C, 75.58; H 5.49; N, 17.58.

EXAMPLE 122

8-Ethyl-6-naphthalen-2-yl-2-phenylamino-8H-pyrido[2,3-d]pyrimidin-7-one (8-Ethyl-7-imino-6-naphthalen-2-yl-7,8-dihydro-pyrido[2,3-d]pyrimidin-2-yl)-phenylamine (150 mg) was added to 1 mL of acetic anhydride and heated at reflux for 2 minutes. The reaction was cooled and concentrated, resulting in an oil which was heated at reflux with 10 mL of 6N HCl for 10 minutes. The reaction was cooled, and 40 mL of water was added causing precipitation. The precipitate was removed by filtration and washed with water. The resulting solid was dried in a vacuum oven to provide 8-ethyl-6-naphthalen-2-yl-2-phenylamino-8H-pyrido[2,3-d]-pyrimidin-7-one; mp 254°–256° C.
Mass spectrum (CI) 393 (M$^+$).
Analysis calculated for $C_{25}H_{20}N_4O \cdot HCl$: C, 70.00; H, 4.94; N, 13.06.
Found: C, 68.61; H, 4.97; N, 12.83.

EXAMPLE 123

(6-Biphenyl-4-yl-8-ethyl-7-imino-7,8-dihydro-pyrido[2,3-d]pyrimidin-2-yl)-phenylamine To a suspension of NaH (60% in mineral oil, 27 mg) in 5 mL of 2-ethoxyethanol was added 4-biphenylacetonitrile (263 mg, 1.36 mmol). After stirring for 5 minutes at room temperature, 4-ethylamino-2-phenylamino-pyrimidine-5-carboxaldehyde (300 mg, 1.24 mmol) was added and the reaction heated at 110° C. for 1 hour, resulting in a dark brown solution. Upon cooling, the solution was poured into water which caused precipitation. The resulting precipitate was removed by filtration and washed with water. The crude product was purified by flash chromatography, eluting with 5% methanol/methylene chloride, followed by 10% methanol/methylene chloride. Concentration of product fractions yielded 427 mg (83%) of (6-biphenyl-4-yl-8-ethyl-7-imino-7,8-dihydro-pyrido[2,3-d]pyrimidin-2-yl)-phenylamine; mp 245°–249° C.

Mass spectrum (CI) 418 ($M^+$).

Analysis calculated for $C_{27}H_{23}N_5$: C, 77.67; H, 5.55; N, 16.78.

Found: C, 76.16; H, 5.54; N, 16.36.

EXAMPLE 124

6-Biphenyl-4-yl-8-ethyl-2-phenylamino-8H-pyrido[2,3-d]-pyrimidin-7-one

Prepared from (6-biphenyl-4-yl-8-ethyl-7-imino-7,8-dihydro-pyrido[2,3-d]pyrimidin-2-yl)-phenylamine following the procedure of Example 116; mp softens at 235° C.

Mass spectrum (CI) 419 ($M^+$).

Analysis calculated for $C_{27}H_{22}N_4O \cdot HCl$: C, 71.28; H, 5.10; N, 12.32.

Found: C, 69.22; H, 5.10; N, 11.85.

The compounds of Formula I are valuable inhibitors of protein tyrosine kinases and possess therapeutic value as cellular antiproliferative agents for the treatment of proliferative disorders. These compounds are potent inhibitors of one or more of the protein kinases, PDGF, FGF, EGF, viral-src (V-src), and cellular-src (C-src). The invention compounds are thus useful in treating atherosclerosis, restenosis, and cancer. Specific tumors to be treated with the compounds include small-cell lung carcinoma such as that described in *An. Rev. Respir. Dis.*, 142:554–556 (1990); human breast cancer as described in *Cancer Research*, 52:4773–4778 (1992); low grade human bladder carcinomas of the type described in *Cancer Research*, 52:1457–1462 (1992); human colorectal cancer as discussed in *J. Clin. Invest.*, 91:53–60 (1993); and in *J. Surg. Res.*, 54:293–294 (1993).

The compounds of this invention have been evaluated in standard assays which are utilized to determine inhibition of tyrosine kinases. The assays were conducted as follows:

Purification of Epidermal Growth Factor Receptor Tyrosine Kinase

Human EGF receptor tyrosine kinase was isolated from A431 epidermoid carcinoma cells by the following methods. Cells were grown in roller bottles in 50% Dulbecco's Modified Eagle medium and 50% HAM F-12 nutrient media (Gibco) containing 10% fetal calf serum. Approximately $10^9$ cells were lysed in two volumes of buffer containing 20 mM 2-(4N-[2-hydroxymethyl]-piperazin-1-yl)ethanesulfonic acid, pH 7.4, 5 mM ethylene glycol bis(2-aminoethyl ether) N,N,N',N'-tetraacetic acid, 1% Triton X-100, 10% glycerol, 0.1 mM sodium orthovanadate, 5 mM sodium fluoride, 4 mM pyrophosphate, 4 mM benzamide, 1 mM dithiothreitol, 80 µg/mL aprotinin, 40 µg/mL leupeptin, and 1 mM phenylmethylsulfonyl fluoride. After centrifugation at 25,000×g for 10 minutes, the supernatant was equilibrated for 2 hours at 4° C. with 10 mL of wheat germ agglutinin sepharose that was previously equilibrated with 50 mM Hepes, 10% glycerol, 0.1% Triton X-100 and 150 mM NaCl, pH 7.5, (equilibration buffer). Contaminating proteins were washed from the resin with 1M NaCl in equilibration buffer, and the enzyme was eluted with 0.5M N-acetyl-1-D-glucosamine in equilibration buffer.

Determination of $IC_{50}$ Values

Enzyme assays for $IC_{50}$ determinations were performed in a total volume of 0.1 mL, containing 25 mM Hepes, pH 7.4, 5 mM $MgCl_2$, 2 mM $MnCl_2$, 50 µM sodium vanadate, 5–10 ng of EGF receptor tyrosine kinase, 200 µM of a substrate peptide (Ac-Lys-His-Lys-Lys-Leu-Ala-Glu-Gly-Ser-Ala-$Tyr^{472}$-Glu-Glu-Val-$NH_2$, derived from the amino acid ($Tyr^{472}$ has been shown to be 1 of 4 tyrosines in PLC-g that are phosphorylated by the EGF receptor tyrosine kinase (Wahl M. I., et al., *J. Biol. Chem.*, 265:3944–3948 (1990)), and peptides derived from the enzyme sequence surrounding this site are excellent substrates for the enzyme), 10 µM ATP containing 1 µCi of [$^{32}P$]ATP and incubated for 10 minutes at room temperature. The reaction was terminated by the addition of 2 mL of 75 mM phosphoric acid and passed through a 2.5-cm phosphocellulose filter disc to bind the peptide. The filter was washed 5 times with 75 mM phosphoric acid and placed in a vial along with 5 mL of scintillation fluid (Ready gel Beckman).

PDGF and FGF Receptor Tyrosine Kinase Assays

Full length cDNAs for the mouse PDGF-β and human FGF-1 (flg) receptor tyrosine kinases were obtained from J. Escobedo and prepared as described in *J. Biol. Chem.*, 262:1482–1487 (1991), and PCR primers were designed to amplify a fragment of DNA that codes for the intracellular tyrosine kinase domain. The fragment was melded into a baculovirus vector, cotransfected with AcMNPV DNA, and the recombinant virus isolated. SF9 insect cells were infected with the virus to overexpress the protein, and the cell lysate was used for the assay. The assay was performed in 96-well plates (100 µL/incubation/well), and conditions were optimized to measure the incorporation of $^{32}P$ from $\gamma^{32}P$-ATP into a glutamate-tyrosine co-polymer substrate. Briefly, to each well was added 82.5 µL of incubation buffer containing 25 mM Hepes (pH 7.0), 150 mM NaCl, 0.1% Triton X-100, 0.2 mM PMSF, 0.2 mM $Na_3VO_4$, 10 mM $MnCl_2$, and 750 µg/mL of Poly (4:1) glutamate-tyrosine followed by 2.5 µL of inhibitor and 5 µL of enzyme lysate (7.5 µg/µL FGF-TK or 6.0 µg/µL PDGF-TK) to initiate the reaction. Following a 10 minute incubation at 25° C., 10 µL of $\gamma^{32}$ P-ATP (0.4 µCi plus 50 µM ATP) was added to each well and samples were incubated for an additional 10 minutes at 25° C. The reaction was terminated by the addition of 100 µL of 30% trichloroacetic acid (TCA) containing 20 mM sodium pyrophosphate and precipitation of material onto glass fiber filter mats (Wallac). Filters were washed 3 times with 15% TCA containing 100 mM sodium pyrophosphate and the radioactivity retained on the filters counted in a Wallac 1250 Betaplate reader. Nonspecific activity was defined as radioactivity retained on the filters following incubation of samples with buffer alone (no enzyme). Specific enzymatic activity was defined as total activity (enzyme plus buffer) minus nonspecific activity. The concentration of a compound that inhibited specific activity by 50% ($IC_{50}$) was determined based on the inhibition curve.

V-src and C-src Kinase Assays

V-src or C-src kinase is purified from baculovirus infected insect cell lysates using an antipeptide monoclonal antibody directed against the N-terminal 2–17 amino acids. The antibody, covalently linked to 0.65-µm latex beads, is added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 µg/mL each of leupeptin, pepstatin, and aprotinin. Insect cell lysate containing either the C-src or V-src protein is incubated with these beads for 3–4 hours at 4° C. with rotation. At the end of the lysate incubation, the beads are rinsed 3 times in lysis buffer, resuspended in lysis buffer containing 10% glycerol, and frozen. These latex beads are thawed, rinsed 3 times in assay buffer which is comprised of 40 mM tris pH 7.5, 5 mM $MgCl_2$, and suspended in the same buffer. In a Millipore 96-well plate with a 0.65 µm polyvinylidine membrane bottom are added the reaction components: 10-μL V-src or C-src beads, 10 μL of 2.5 mg/mL poly GluTyr substrate, 5 μM ATP containing 0.2 μCi labeled $^{32}$P-ATP, 5 μL DMSO containing inhibitors or as a solvent control, and buffer to make the final volume 125 μL. The reaction is started at room temperature by addition of the ATP and quenched 10 minutes later by the addition of 125 μL of 30% TCA, 0.1M sodium pyrophosphate for 5 minutes on ice. The plate is then filtered and the wells washed with two 250-μL aliquots of 15% TCA, 0.1M pyrophosphate. The filters are punched, counted in a liquid scintillation counter, and the data examined for inhibitory activity in comparison to a known inhibitor such as erbstatin. The method is described more fully in *J. Med. Chem.*, 37:598–609 (1994).

Cell Culture

Rat aorta smooth muscle cells (RASMC) were isolated from the thoracic aorta of rats and explanted according to the method of Ross, *J. Cell. Biol.*, 30:172–186 (1971). Cells were grown in Dulbecco's modified Eagle's medium (DMEM, Gibco) containing 10% fetal calf serum (FBS, Hyclone, Logan, Utah), 1% glutamine (Gibco) and 1% penicillin/streptomycin (Gibco). Cells were identified as smooth muscle cells by their "hill and valley" growth pattern and by fluorescent staining with a monoclonal antibody specific for SMC ∝-actin (Sigma). RASMC were used between passages 5 and 20 for all experiments. Test compounds were prepared in dimethylsulfoxide (DMSO) in order to achieve consistency in the vehicle and to ensure compound solubility. Appropriate DMSO controls were simultaneously evaluated with the test compounds.

[$^{3}$H]-Thymidine Incorporation Assay

RASMC were plated into a 24-well plate (30,000 cells/well) in DMEM with 10% FBS. After 4 days, cells reached confluence and were made quiescent by incubation in DMEM/F12 medium (Gibco) containing 0.2% FBS for another 2 days. DNA synthesis was induced by incubating cells for 22 hours with either PDGF-BB, bFGF, or FBS, plus test compound in 0.5 mL/well serum-substituted medium (DMEM/F12+1% CPSR-2 from Sigma). After 18 hours, 0.25 μCi/well [$^{3}$H]-thymidine was added. Four hours later, the incubation was stopped by removing the radioactive media, washing the cells twice with 1 mL cold phosphate-buffered saline, and then washing 2 times with cold 5% trichloroacetic acid. The acid-insoluble fraction was lysed in 0.75 mL 0.25N NaOH and the radioactivity determined by liquid scintillation counting. IC$_{50}$ values were determined graphically.

PDGF Receptor Autophosphorylation

RASMC were grown to confluency in 100 mm dishes. Growth medium was removed and replaced with serum-free medium and cells were incubated at 37° C. for an additional 24 hours. Test compounds were then added directly to the medium and cells incubated for an additional 2 hours. After 2 hours, PDGF-BB was added at a final concentration of 30 ng/mL for 5 minutes at 37° C. to stimulated autophosphorylation of the PDGF receptor. Following growth factor treatment, the medium was removed, and cells were washed with cold phosphate-buffered saline and immediately lysed with 1 mL of lysis buffer (50 mM HEPES[pH 7.5], 150 mM NaCl, 10% glycerol, 1% Triton X-100, 1 mM EDTA, 1 mMEGTA, 50 mM NaF, 1 mM sodium orthovanadate, 30 mM p-nitrophenyl phosphate, 10 mM sodium pyrophosphate, 1 mM phenylmethyl sulfonyl fluoride, 10 μg/mL aprotinin, and 10 μg/mL leupeptin). Lysates were centrifuged at 10,000×g for 10 minutes. Supernatants were incubated with 10 μL of rabbit anti-human PDGF type AB receptor antibody (1:1000) for 2 hours. Following the incubation, protein-A-sepharose beads were added for 2 hours with continuous mixing, and immune complexes bound to the beads washed four times with 1 mL lysis wash buffer. Immune complexes were solubilized in 30 μL of Laemmli sample buffer and electrophoresed in 4–20% SDS polyacrylamide gels. Following electrophoresis, separated proteins were transferred to nitrocellulose and immunoblotted with anti-phosphotyrosine antiserum. Following incubation with [$^{125}$I]-protein-A, the levels tyrosine phosphorylated proteins were detected by phosphorimage analysis and protein bands quantitated via densitometry. IC$_{50}$ values were generated from the densitometric data.

Transplanted Tumor Assay

Several of the invention compounds (e.g., compounds of Examples 54 and 80) have increased the life span of animals infected with transplanted tumors. F1 hybrid mice were used in the assay. The mice receive ascites fluid or dilutions of tumor brei on Day 0. A sample of the inocula is incubated in thioglycolate media as a check for gross contamination of the tumor material. After all test animals are inoculated with tumors, they are randomized for the assay. Control animals receive vehicle, while treated animals receive an invention compound dissolved in the vehicle, generally by infusion by tail tether. All animals are monitored daily for acute toxicity and other clinical signs. Survival is checked daily for the control group and treated group. The assay generally is continued for 60 days, at which time all surviving animals are euthanized.

The following Tables I and II present biological data for representative compounds of the invention when analyzed in the foregoing assays.

TABLE I

Inhibition of Protein Tyrosine Kinases
(IC$_{50}$ μM or % Inhibition at 50 μM)

| Example | PDGFr-TK | FGFr-TK | C-src TK | EGF-FL |
|---|---|---|---|---|
| 7 | 42% | 28% | | |
| 8 | 48.0 | 48.0 | | |
| 9 | 35% | 34% | | |
| 10 | 21.2 | 3.0 | 0.225 | |
| 12 | 4.87 | 1.32 | 0.262 | 5.6 |
| 13 | 2.56 | 6.20 | 0.29 | 88% |
| 14 | 1.41 | 7.65 | 3.92 | 65% |
| 15 | 5.18 | 5.79 | 4.22 | |
| 16 | 5.45 | 6.49 | 3.1 | |
| 17 | 16.5 | 56.7 | | |
| 19 | 16% | 20% | | |
| 20 | 27% | 21.9 | | |
| 21 | 8.85 | 1.97 | 0.963 | 93% |
| 22 | 13% | 17% | | |
| 23 | 16% | 34% | | |
| 24 | 13% | 16% | | |
| 26 | 11.3 | 19.8 | | |
| 28 | 0% | 0% | | |
| 29 | 32% | 17.2 | | |
| 30 | 0.98 | 0.54 | 0.155 | 77% |
| 31 | 1.2 | 0.46 | 100% | 100% |
| 32 | 0.875 | 0.737 | 33% | 100% |
| 33 | 1.84 | 0.426 | 0.89 | 95% |
| 34 | 2.73 | 1.2 | 0.037 | 2.9 |
| 35 | 3.57 | 1.91 | 0.34 | 1.2 |
| 36 | 7.53 | 1.45 | 0.56 | |
| 37 | 33% | 29% | 33% | 42% |
| 38 | 1.09 | 0.23 | 0.003 | 8.7 |
| 39 | 19% | 5.5 | 26% | 24% |
| 40 | 3.22 | 1.45 | | |
| 41 | 16% | 0% | 12% | 52% |
| 42 | 4.49 | 0.8 | 0.588 | 82% |
| 43 | 5.35 | 1.35 | 0.325 | 67% |
| 44 | 2.09 | 0.88 | 1.57 | 64% |
| 45 | 5.68 | 4.04 | 2.39 | 85% |

TABLE I-continued

Inhibition of Protein Tyrosine Kinases
($IC_{50}$ μM or % Inhibition at 50 μM)

| Example | PDGFr-TK | FGFr-TK | C-src TK | EGF-FL |
|---|---|---|---|---|
| 46 | 17.6 | 18.1 | | |
| 47 | 5.98 | 1.26 | 36% | 70% |
| 48 | 17.9 | 19.6 | 2.54 | 64% |
| 49 | 4.65 | 4.01 | 0.813 | 61% |
| 50 | 7.31 | 4.17 | 3.24 | 59% |
| 51 | 7.16 | 8.03 | 1.57 | 55% |
| 52 | 5.36 | 3.61 | 1.05 | 46% |
| 53 | 20% | 45% | 15% | 0.85 |
| 54 | 0.231 | 0.84 | 0.024 | 0.078 |
| 55 | 1.8 | 2.20 | 0.059 | 0.308 |
| 56 | 1.68 | 3.01 | 0.070 | |
| 57 | 0.44 | 0.646 | 0.050 | 0.089 |
| 58 | 0.071 | 0.159 | 0.023 | 0.119 |
| 59 | 0.853 | 0.201 | 0.12 | 0.21 |
| 60 | 9.38 | 6.52 | 1.64 | |
| 61 | 26.5 | 8.6 | 64% | |
| 62 | 0.736 | 0.453 | 0.365 | 1.0 |
| 63 | 1.01 | 1.05 | 0.033 | 0.14 |
| 64 | 0.546 | 0.403 | 0.020 | 0.065 |
| 67 | 31% | 27% | | |
| 68 | 29% | 12.5 | | |
| 69 | 0.593 | 0.214 | 0.079 | 0.12 |
| 70 | 0.475 | 0.109 | 0.070 | |
| 71 | 1.14 | 3.46 | 6.0 | 0.54 |
| 72 | 0.259 | 0.365 | 0.052 | 0.033 |
| 73 | 1.3 | 0.45 | 0.037 | 0.16 |
| 74 | 0.76 | 0.277 | 0.079 | 0.13 |
| 75 | 0.353 | 0.141 | 0% | 0.021 |
| 76 | 2.38 | 0.466 | 33% | 0.3 |
| 77 | 1.11 | 0.124 | 0.019 | 0.094 |
| 78 | 1.69 | 0.143 | 46% | 0.097 |
| 79 | 0.102 | 0.172 | 0.044 | 0.11 |
| 80 | 0.105 | 0.045 | 0.006 | 0.035 |
| 81 | 0.743 | 0.279 | 94% | 4.5 |
| 82 | 0.14 | 0.122 | 0.004 | |
| 83 | 1.18 | 0.333 | 0.019 | 0.059 |
| 84 | 0.39 | 0.25 | 0.023 | 0.63 |
| 85 | 0.37 | 0.56 | 0.013 | 1.32 |
| 86 | 0.07 | 0.061 | 0.009 | 0.13 |
| 87 | 0.35 | 0.17 | 0.020 | 0.14 |
| 88 | 38.0 | 69.0 | 0.095 | |
| 89 | 1.48 | 1.49 | 0.014 | |
| 90 | 0.14 | 0.11 | 0.006 | 0.15 |
| 93 | 0.076 | 0.087 | 0.009 | 0.25 |
| 102 | 0.355 | 28% | | |
| 103 | 0.15 | 1.06 | | |
| 104 | 0.373 | 58.0 | | |
| 106 | 1.23 | 0.415 | | |
| 107 | 43% | 9.24 | 52% | |
| 108 | 5.05 | 1.19 | 0.158 | 87% |
| 109 | 9.29 | 3.37 | 0.240 | 0.062 |
| 110 | 25% | 20.3 | 17.19 | 64% |
| 111 | 3.15 | 1.5 | 0.041 | 1.4 |
| 112 | 11.2 | 9.1 | 1.16 | 19% |
| 113 | 1.76 | 0.97 | 87% | 6.7 |
| 114 | 5.17 | 3.31 | 1.09 | 3.2 |
| 115 | 0.17 | 0.097 | | |
| 116 | 0.152 | 1.96 | 1.38 | 0.18 |
| 117 | 38.0 | 0.8 | | |
| 118 | 12% | 29% | | |
| 120 | 1.83 | 2% | 29% | |
| 121 | 44% | 29.0 | | |
| 122 | 33.0 | 20.0 | | |
| 123 | 24% | 26% | | |
| 124 | 38% | 15% | 11% | |

TABLE II

Cellular Assays ($IC_{50} = $ μM)

| Example | Inhibition of PDGF-Stimulated Receptor Auto Phosphorylation in Rat Aortic Smooth Muscle Cells |
|---|---|
| 12 | 9.4 |
| 54 | 0.016 |
| 55 | 0.06 |
| 58 | 0.013 |
| 80 | 0.026 |

The invention compounds also have been evaluated in assays utilizing cells from various human colon adenocarcinomas. Three such human cell lines were identified as HCT-8, SW-620, and HT-29. In a typical assay, the cells are suspended in 0.3% soft agar containing an invention compound at various concentration levels, and are plated into six-well plates, each plate containing a 1% agar plug. The cell plates are incubated at 37° C. in a humidified carbon dioxide (5%) incubator, generally for 2 weeks. At the end of the incubation period, colonies of cells are detected by staining the wells with 1 mg/mL of p-iodonitrotetrazolium violet. The cells are counted on an optical colony counter. The concentration of test compound required to inhibit the formation of cell colonies at a level of 50% relative to control plates containing no test compound is recorded as the $IC_{50}$. The $IC_{50}$s for several invention compounds against human colon adenocarcinoma cells are listed in Table III.

TABLE III

Inhibition of Human Colon Adenocarcinoma $IC_{50}$ (μM)

| Compound of Example No. | HCT-8 | SW-620 | HT-29 |
|---|---|---|---|
| 38 | 3.15 | | |
| 54 | 0.52 | 0.14 | 0.49 |
| 55 | 0.11 | 0.12 | 0.43 |
| 56 | | 1.1 | |
| 57 | 0.25 | 0.52 | 0.74 |
| 58 | 0.17 | 0.13 | 0.38 |
| 63 | 1.0 | | |
| 69 | | | 1.11 |
| 70 | | | 3.5 |

As noted above, the compounds of Formula I are useful for treating cancer and other proliferative diseases such as psoriasis, restenosis, and atherosclerosis.

The invention compounds are especially useful for treating restenosis following balloon angioplasty of occluded arteries. Restenosis occurs in about 40% of individuals undergoing angioplasty of calcified arteries and is a major problem associated with this form of treatment of patients suffering from such cardiac condition. The invention compounds demonstrate good activity when evaluated in standard tests such as described below.

Balloon Angioplasty of Rat Carotid Arteries

Male Sprague-Dawley rats (350–450 g) are divided into 2 treatment groups: 1 group of rats (n=10) are treated with drug (100 mg/kg PO, BID) and the second group received vehicle (2 mL/kg PO, BID (n=10)). All animals were pretreated for 2 days prior to surgery and continued to receive daily drug treatment postinjury until sacrificed.

Balloon injury in rat carotid arteries were performed according to the following protocol. Rats were anesthetized with Telazol (0.1 mL/100 g IM), and the carotid artery exposed via an anterior mid-line incision on the neck. The carotid artery was isolated at the bifurcation of the internal and external carotid arteries. A 2F embolectomy catheter was inserted in the external carotid artery and advanced down the common carotid to the level of the aortic arch. The balloon was inflated and the catheter is dragged back to the point of entry and then deflated. This procedure is repeated 2 more times. The embolectomy catheter was then removed and the external carotid artery was ligated leaving flow intact through the internal carotid artery. Surgical incisions were closed, and the animal was allowed to recover from anesthesia before being returned to its home cage.

At various time points postinjury animals were euthanized with $CO_2$ inhalation, and the carotid artery was perfusion fixed and processed for histologic examination. Morphologic determination of lesion size was made by measuring the area of the carotid artery intima expressed as a ratio of the media in individual animals. Up to 16 sections were prepared from each animal to give a uniform representation of lesion size down the length of the carotid artery. The cross-sectional areas of the blood vessels were quantified using an image analysis program from Princeton Gamma Tech (Princeton, N.J.).

The compounds of the present invention can be formulated and administered in a wide variety of oral and parenteral dosage forms, including transdermal and rectal administration. It will be recognized to those skilled in the art that the following dosage forms may comprise as the active component, either a compound of Formula I or a corresponding pharmaceutically acceptable salt or solvate of a compound of Formula I.

A further embodiment of this invention is a pharmaceutical formulation comprising a compound of Formula I together with a pharmaceutically acceptable carrier, diluent, or excipient therefor. For preparing pharmaceutical compositions with the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component.

In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water-propylene glycol solutions. For parenteral injection, liquid preparations can be formulated in solution in aqueous polyethylene glycol solution, isotonic saline, 5% aqueous glucose, and the like.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with a viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The therapeutically effective dose of a compound of Formula I will generally be from about 1 mg to about 100 mg/kg of body weight per day. Typical adult doses will be about 50 to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formula I will be administered a dosage of about 1 to about 500 mg per day, either singly or in multiple doses over a 24-hour period.

EXAMPLE 125

A pharmaceutical formulation in the form of hard gelatin capsules for oral administration are prepared using the following ingredients:

|  | Quantity (mg/capsule) |
| --- | --- |
| Active compound | 250 |
| Starch powder | 200 |
| Magnesium stearate | 10 |
| Total | 460 mg |

The above ingredients are mixed and filled into hard gelatin capsules in 460 mg quantities. A typical active ingredient is 6-(2-methyl-1-naphthyl)-7-imino-8-isopropyl-7,8-dihydro-pyrido[2,3-d]pyrimidine-2-ylamine. The composition is administered from 2 to 4 times a day for treatment of postsurgical restenosis.

EXAMPLE 126

| Formulation for Oral Suspension | |
|---|---|
| Ingredient | Amount |
| 2-(cyclopropylamino)-6-(2-bromo-4-methoxy-5-ethylthiophenyl)-8-n-hexyl-pyrido[2,3-d]pyrimidine-7(8H)-one | 500 mg |
| Sorbitol solution (70% N.F.) | 40 mL |
| Sodium benzoate | 150 mg |
| Saccharin | 10 mg |
| Cherry Flavor | 50 mg |
| Distilled water q.s. ad | 100 mL |

The sorbitol solution is added to 40 mL of distilled water and the pyridopyrimidine is suspended therein. The saccharin, sodium benzoate, and flavoring are added and dissolved. The volume is adjusted to 100 mL with distilled water. Each milliliter of syrup contains 5 mg of active ingredient.

EXAMPLE 127

Tablets each containing 60 mg of active ingredient

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1.0 mg |
| Total | 150 mg |

The active ingredients, starch, and cellulose, are passed through a No. 45 mesh U.S. sieve and mixed thoroughly. The solution of polyvinylpyrrolidone is mixed with the resultant powders and then passed through a No. 14 mesh U.S. sieve. The granules are dried at 50° C. to 60° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

A typical active ingredient utilized in the above preparation is the compound of Example 12.

EXAMPLE 128

A parenteral composition suitable for administration by injection is prepared by dissolving 100 mg of 2-amino-6-(2,6-dichlorophenyl)-7-thioxo-pyrido[2,3-d]pyrimidine in 250 mL of 0.9% aqueous sodium chloride solution and adjusting the pH of the solution to about 7.0. This formulation is well suited for the treatment of breast cancer.

EXAMPLE 129

Preparation for Suppositories

A mixture of 500 mg of 2-methylsulfanyl-6-(2,6-dichlorophenyl)-pyrido[2,3-d]pyrimidin-7(8H)-one and 1500 mg of theobroma oil are blended to uniformity at 60° C. The mixture is cooled to 24° C. in tapered molds. Each suppository will weigh about 2 g and can be administered from 1 to 2 times each day for treatment of bacterial infections.

| Topical Preparation | |
|---|---|
| Ingredient | Amount (mg) |
| 2-Acetamido-6-(2-naphthyl)-8-ethyl-pyrido[2,3-d]pyrimidin-7(8H)-one | 20 |
| Propylene Glycol | 100 |
| White Petrolatum | 500 |
| Cetearyl Alcohol | 50 |
| Glyceryl Stearate | 100 |
| PEG 100 Stearate | 100 |
| Ceteth-20 | 50 |
| Monobasic Sodium Phosphate | 80 |
| TOTAL | 1000 |

EXAMPLE 131

Slow Release Preparation

Five hundred milligrams of 6-(2,6-dichlorophenyl)-2-[4-(2-diethylaminoethoxy)-phenylamino]-8-methoxy-8H-pyrido[2,3-d]pyrimidin-7-one hydrochloride was placed in an osmotic pump tablet and administered orally for treatment and prevention of restenosis.

What is claimed is:

1. A compound of the formula wherein

X is NH, N-Acyl, O, or S;

$R_1$ is $SOR_3$ or $SO_2R_3$, $R_2$, $R_3$, and $R_4$ independently are hydrogen, $(CH_2)_n Ph$ where Ph is phenyl or substituted phenyl and n is 0, 1, 2, or 3, heteroaromatic, cycloalkyl, $C_1$–$C_6$ alkanoyl, $C_1$–$C_6$ alkyl, $C_2$–$C_6$ alkenyl, or $C_2$–$C_6$ alkynyl, where the alkyl, alkenyl, and alkynyl groups may be substituted by $NR_5R_6$, phenyl, substituted phenyl, thioalkyl, alkyloxy, hydroxy, carboxy, halogen, or cycloalkyl, and where $R_5$ and $R_6$ are independently hydrogen, $C_1$–$C_6$ alkyl, $C_2$–$C_6$ alkenyl, $C_2$–$C_6$ alkynyl, $(CH_2)_n Ph$ where Ph is phenyl or substituted phenyl and n is 0, 1, 2, or 3, cycloalkyl, or heteroaromatic, and $R_5$ and $R_6$ taken together with the nitrogen to which they are attached can complete a ring having 3 to 7 carbon atoms and optionally containing 1, 2, or 3 heteroatoms selected from nitrogen, oxygen, and sulfur;

$R_4$ can additionally be —C(=O)$R_3$, —C(=O)O$R_3$, —SO$_2R_3$, —SO$_2NR_5R_6$, —C(=O)NR$_5$R$_6$, —C(=S)NR$_5$R$_6$, —C(=NH)R$_3$, —C(=NH)NR$_5$R$_6$, and $R_3$ and $R_4$ can be taken together with the nitrogen to which they are attached to complete a ring having 3 to 7 carbon atoms and optionally containing 1, 2, or 3 heteroatoms selected from nitrogen, oxygen, and sulfur;

Ar is phenyl, substituted phenyl, or heteroaromatic;

and the pharmaceutically acceptable salts thereof.

2. A compound of claim 1 having the formula

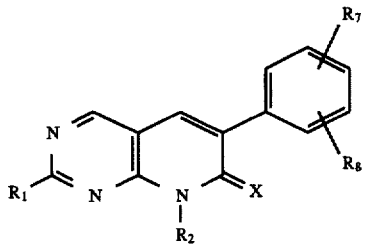

wherein R₇ and R₈ independently are C₁–C₆ alkoxy and R₁, R₂, and X are as defined above.

3. A compound of claim 2 wherein R₂ is C₁–C₆ alkyl or substituted C₁–C₆ alkyl.

4. A compound of claim 2 wherein X is NH.

5. A compound which is 6-(2,6-Dichlorophenyl)-8-methyl-2-[3-(4-methylpiperazin-1-yl)-propyiamino]-8H-pyrido[2,3-d]pyrimidin-7-one;

6-(2,6-Dichlorophenyl)-8-methyl-2-methylamino-8H-pyrido[2,3-d]pyrimidin-7-one;

6-(2,6-Dichlorophenyl)-2-dimethylaminomethyl-8H-pyrido[2,3-d]pyrimidin-7-one;

6-(2,6-Dichlorophenyl)-2-ethylamino-8-methyl-8H-pyrido[2,3-d]pyrimidin-7-one;

6-(2,6-Dichlorophenyl)-2-(2-hydroxyethylamino)-8-methyl-8H-pyrido[2,3-d]pyrimidin-7-one;

6-(2,6-Dichlorophenyl)-2-isopropylaminomethyl-8H-pyrido[2,3-d]pyrimidin-7-one;

2-Butylamino-6-(2,6-dichlorophenyl)-8-methyl-8H-pyrido[2,3-d]pyrimidin-7-one;

2-Benzylamino-6-(2,6-dichlorophenyl)-8-methyl-8H-pyrido[2,3-d]pyrimidin-7-one;

6-(2,6-Dichlorophenyl)-8-methyl-2-(3-morpholin-4-yl-propylamino)-8H-pyrido[2,3-d]-pyrimidin-7-one;

6-(2,6-Dichlorophenyl)-2-[2-(3,4-dimethoxyphenyl)-ethylamino]-8-methyl-8H-pyrido[2,3-d]-pyrimidin-7-one;

6-(2,6-Dichlorophenyl)-8-methyl-2-[(pyridinylmethyl)-amino]-8H-pyrido[2,3-d]pyrimidin-7-one;

6-(2,6-Dichlorophenyl)-8-methyl-2-[(pyridin-3-ylmethyl)-amino]-8H-pyrido[2,3-d]pyrimidin-7-one;

6-(2,6-Dichlorophenyl)-8-methyl-2-(2-pyridin-2-yl-ethylamino)-8H-pyrido[2,3-d]pyrimidin-7-one;

6-(2,6-Dichlorophenyl)-2-[3-[4-(2-methoxyphenyl)-piperazin-1-yl]-propylamino]-8-methyl-8H-pyrido[2,3-d]pyrimidin-7-one;

6-(2,6-Dichlorophenyl)-8-methyl-2-[4-(4-methylpiperazin-1-yl)-butylamino]-8H-pyrido[2,3-d]pyrimidin-7-one;

6-[6-(2,6-Dichlorophenyl)-8-methyl-7-oxo-7,8-dihydropyrido[2,3-d]pyrimidin-2-ylamino]-hexanoic acid, tert-butyl ester;

6-[6-(2,6-Dichlorophenyl)-8-methyl-7-oxo-7,8-dihydropyrido[2,3-d]pyrimidin-2-ylamino]-hexanoic acid;

6-(2,6-Dichlorophenyl)-8-ethyl-2-[3-(4-methylpiperazin-1-yl)-propylamino]-8H-pyrido[2,3-d]pyrimidin-7-one;

6-(2,6-Dichlorophenyl)-8-methyl-2-[5-(4-methylpiperazin-1-yl)-pentylamino]-8H-pyrido[2,3-d]pyrimidin-7-one;

4-{4-[6-(2,6-Dichlorophenyl)-8-methyl-7-oxo-7,8-dihydropyrido[2,3-d]pyrimidin-2-ylamino]-phenyl}-butyric acid, ethyl ester; or 4-{4-[6-(2,6-Dichlorophenyl)-8-methyl-7-oxo-7,8-dihydropyrido[2,3-d]pyrimidin-2-ylamino]-phenyl}-butyric acid.

6. A compound of claim 2 wherein X is O.

7. The compound which is

2-Amino-6-(2,6-dichlorophenyl)-8-propyl-8H-pyrido[2,3-d]pyrimidin-7-one;

2-Amino-8-butyl-6-(2,6-dichlorophenyl)-8H-pyrido[2,3-d]pyrimidin-7-one;

2-Amino-6-(2,6-dichlorophenyl)-8-isobutyl-8H-pyrido[2,3-d]pyrimidin-7-one;

2-Amino-6-(2,6-dichlorophenyl)-8-(3-dimethylaminopropyl)-8H-pyrido[2,3-d]pyrimidin-7-one;

[2-Amino-6-(2,6-dichlorophenyl)-7-oxo-7H-pyrido[2,3-d]pyrimidin-8-yl]-acetic acid methyl ester;

[2-Amino-6-(2,6-dichlorophenyl)-7-oxo-7H-pyrido[2,3-d]pyrimidin-8-yl]-acetic acid tert-butyl ester;

[2-Amino-6-(2,6-dichlorophenyl)-7-oxo-7H-pyrido[2,3-d]pyrimidin-8-yl]-acetic acid;

2-Amino-8-benzyl-6-(2,6-dichlorophenyl)-8H-pyrido[2,3-d]pyrimidin-7-one;

2-Amino-8-(3-bromobenzyl)-6-(2,6-dichlorophenyl)-8H-pyrido[2,3-d]pyrimidin-7-one;

4-[2-Amino-6-(2,6-dichlorophenyl)-7-oxo-7H-pyrido[2,3-d]pyrimidin-8-ylmethyl]-benzoic acid methyl ester;

2-Amino-8-(2,6-dichlorobenzyl)-6-(2,6-dichlorophenyl)-8H-pyrido[2,3-d]pyrimidin-7-one;

2-Amino-6-(2,6-dichlorophenyl)-8-(4-methoxybenzyl)-8H-pyrido[2,3-d]pyrimidin-7-one;

2-Amino-6-(2,6-dichlorophenyl)-8-pyridin-4-ylmethyl-8H-pyrido[2,3-d]pyrimidin-7-one; or 2-Amino-6-(2,6-dichlorophenyl)-8-(3-phenylpropyl)-8H-pyrido[2,3-d]pyrimidin-7-one.

8. A compound of claim 2 wherein R₄ is C₁–C₆ alkyl substituted with NR₅R₆.

9. A compound of claim 8 wherein R₅ and R₆ both are C₁–C₆ alkyl.

10. A compound of claim 9 wherein X is NH.

11. A compound of claim 9 wherein X is O.

12. A compound of claim 2 wherein X is S.

13. A compound of claim 2 wherein X is O.

14. The compound which is 6-(2,6-Dichlorophenyl)-2-methanesulfinyl-8-methyl-8H-pyrido[2,3-d]pyrimidin-7-one;

6-(2,6-Dichlorophenyl)-8-methyl-2-methylsulfanyl-8H-pyrido[2,3-d]pyrimidin-7-one;

6-(2,6-Dichlorophenyl)-2-methanesulfonyl-8-methyl-8H-pyrido[2,3-d]pyrimidin-7-one;

6-(2,6-Dichlorophenyl)-8-methyl-2-methylsulfanyl-8H-pyrido[2,3-d]pyrimidin-7-one; or 6-(2,6-Dichlorophenyl)-8-ethyl-2-methanesulfonyl-8H-pyrido[2,3-d]pyrimidin-7-one.

15. A compound of claim 2 wherein X is N-Acyl.

16. The compound which is

N-[6-(2,6-Dichlorophenyl)-8-ethyl-2-methylsulfanyl-8H-pyrido[2,3-d]pyrimidin-7-ylidene]-acetamide.

17. A compound of the formula

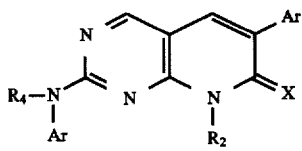

wherein:

X is NH, N-Acyl, O, or S;

$R_2$ is $(CH_2)_n$Ph where Ph is phenyl or substituted phenyl and n is 0, 1, 2, or 3, heteroaromatic, cycloalkyl, $C_1$–$C_6$ alkanoyl, $C_1$–$C_6$ alkyl, $C_2$–$C_6$ alkenyl, and $C_2$–$C_6$ alkynyl, where the alkyl, alkenyl, and alkynyl groups may be substituted by $NR_5R_6$, phenyl, substituted phenyl, thioalkyl, alkyloxy, hydroxy, carboxy, halogen, cycloalkyl, and where $R_5$ and $R_6$ are independently hydrogen, $C_1$–$C_6$ alkyl, $C_2$–$C_6$ alkenyl, $C_2$–$C_6$ alkynyl, $(CH_2)_n$Ph where Ph is phenyl or substituted phenyl and n is 0, 1, 2, or 3, cycloalkyl, heteroaromatic, and $R_5$ and $R_6$ taken together with the nitrogen to which they are attached can complete a ring having 3 to 7 carbon atoms and optionally containing 1, 2, or 3 heteroatoms selected from nitrogen, oxygen, and sulfur, $R_4$ is hydrogen, $(CH_2)_n$Ph where Ph is phenyl or substituted phenyl and n is 0, 1, 2, or 3, heteroaromatic, cycloalkyl, $C_1$–$C_6$ alkanoyl, $C_1$–$C_6$ alkyl, $C_2$–$C_6$ alkenyl, and $C_2$–$C_6$ alkynyl, where the alkyl, alkenyl, and alkynyl groups may be substituted by $NR_5R_6$, phenyl, substituted phenyl, thioalkyl, alkyloxy, hydroxy, carboxy, halogen, cycloalkyl, and where $R_5$ and $R_6$ are independently hydrogen, $C_1$–$C_6$ alkyl, $C_2$–$C_6$ alkenyl, $C_2$–$C_6$ alkynyl, $(CH_2)_n$Ph where Ph is phenyl or substituted phenyl and n is 0, 1, 2, or 3, cycloalkyl, heteroaromatic, and $R_5$ and $R_6$ taken together with the nitrogen to which they are attached can complete a ring having 3 to 7 carbon atoms and optionally containing 1, 2, or 3 heteroatoms selected from nitrogen, oxygen, and sulfur, $R_4$ can additionally be —C(=O)$R_3$, —C(=O)O$R_3$, —SO$_2R_3$, —SO$_2$NR$_5$R$_6$, —C(=O)NR$_5$R$_6$, —C(=S) NR$_5$R$_6$, —C(=NH)$R_3$, —C(=NH)NR$_5$R$_6$, and $R_3$ and $R_4$ can be taken together with the nitrogen to which they are attached to complete a ring having 3 to 7 carbon atoms and optionally containing 1, 2, or 3 heteroatoms selected from nitrogen, oxygen, and sulfur;

Ar is phenyl, substituted phenyl, or heteroaromatic; and the pharmaceutically acceptable salts thereof.

18. A method for treating cancer selected from small-cell lung carcinoma, human breast cancer, low grade human bladder carcinoma and human colorectal cancer comprising administering an anti-cancer amount of a compound of claim 17.

19. A compound having the formula

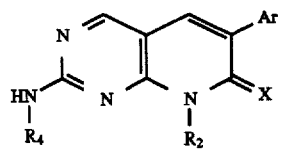

where $R_2$ is $C_1$–$C_6$ alkyl or substituted $C_1$–$C_6$ alkyl, X is NH or O, and $R_4$ is phenyl or substituted phenyl.

20. A compound of claim 19 which is

8-Ethyl-2-phenylamino-6-thiophen-3-yl-8H-pyrido[2,3-d]pyrimidin-7-one;

8-Ethyl-7-imino-6-thiophen-2-yl-7,8-dihydro-pyrido[2,3-d]pyrimidin-2-yl)-phenylamine;

8-Ethyl-2-phenylamino-6-thiophen-2-yl-8H-pyrido[2,3-d]pyrimidin-7-one;

(8-Ethyl-7-imino-6-pyridin-4-yl-7,8-dihydro-pyrido[2,3-d]pyrimidin-2-yl)-2-phenylamine;

8-Ethyl-2-phenylamino-6-pyridin-4-yl-8H-pyrido[2,3-d]pyrimidin-7-one;

(8-Ethyl-7-imino-6-naphthalen-2-yl-7,8-dihydro-pyrido[2,3-d]pyrimidin-2-yl)-phenylamine;

8-Ethyl-6-naphthalen-2-yl-2-phenylamino-8H-pyrido[2,3-d]pyrimidin-7-one;

(6-Biphenyl-4-yl-8-ethyl-7-imino-7,8-dihydro-pyrido[2,3-d]pyrimidin-2-yl)-phenylamine; or 6-Biphenyl-4-yl-8-ethyl-2-phenylamino-8-H-pyrido[2,3-d]pyrimidin-7-one.

21. A compound which is 2-Cyclohexylamino-6-(2,6-dichlorophenyl)-8-methyl-8H-pyrido[2,3-d]pyrimidin-7-one.

22. A pharmaceutical formulation comprising a compound of claim 1 together with a pharmaceutically acceptable carrier therefor.

23. A formulation of claim 22 employing a compound wherein Ar is phenyl or substituted phenyl.

24. A formulation of claim 23 employing a compound wherein X is NH or N-Acyl.

25. A formulation of claim 23 employing a compound wherein X is O.

26. A formulation of claim 23 employing a compound wherein X is S.

27. A method for treating atherosclerosis comprising administering an effective amount of a compound of claim 1 to a mammal in need of treatment.

28. A method for treating psoriasis comprising administering to a mammal in need of treatment an anti-psoriatic amount of a compound of claim 1.

29. A method for treating restenosis comprising administering to a mammal in need of treatment an effective amount of a compound of claim 1.

30. A compound of claim 17 having the formula

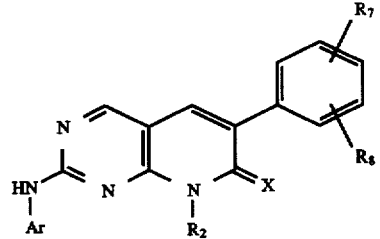

wherein $R_2$ is $C_1$–$C_6$ alkyl or substituted $C_1$–$C_6$ alkyl, X is O or NH, and Ar is phenyl, substituted phenyl, pyridyl or substituted pyridyl.

31. A compound of claim 30 which is 6-(2,6-Dichlorophenyl)-8-methyl-2-phenylamino-8H-pyrido[2,3-d]pyrimidin-7-one;

2-(3-Bromophenylamino)-6-(2,6-dichlorophenyl)-8-methyl-8H-pyrido[2,3-d]-pyrimidin-7-one;

2-(4-Chlorophenylamino)-6-(2,6-dichlorophenyl)-8-methyl-8H-pyrido[2,3-d]pyrimidin-7-one;

2-(Benzo[1,3]dioxol-5-ylamino)-6-(2,6-dichlorophenyl)-8-methyl-8H-pyrido[2,3-d]-pyrimidin-7-one;

6-(2,6-Dichlorophenyl)-8-methyl-2-(pyridinylamino)-8H-pyrido[2,3-d]pyrimidin-7-one;

6-(2,6-Dichlorophenyl)-8-methyl-2-p-tolylamino-8H-pyrido[2,3-d]pyrimidin-7-one;

6-(2,6-Dichlorophenyl)-2-(4-methoxyphenylamino)-8-methyl-8H-pyrido[2,3-d]pyrimidin-7-one;

6-(2,6-Dichlorophenyl)-8-ethyl-2-phenylamino-8H-pyrido[2,3-d]pyrimidin-7-one;

6-(2,6-Dichlorophenyl)-2-(2-methoxyphenylamino)-8-methyl-8H-pyrido[2,3-d]pyrimidin-7-one;

6-(2,6-Dichlorophenyl)-2-(3-methoxyphenylamino)-8-methyl-8H-pyrido[2,3-d]pyrimidin-7-one;

6-(2,6-Dichlorophenyl)-2-(4-methoxy-3-methylphenylamino)-8-methyl-8H-pyrido[2,3-d]pyrimidin-7-one;

6-(2,6-Dichlorophenyl)-8-ethyl-2-(4-methoxyphenylamino)-8H-pyrido[2,3-d]pyrimidin-7-one;

6-(2,6-Dichlorophenyl)-8-ethyl-2-(4-hydroxyphenylamino)-8H-pyrido[2,3-d]pyrimidin-7-one;

6-(2,6-Dichlorophenyl)-2-(4-ethoxyphenylamino)-8-ethyl-8H-pyrido[2,3-d]pyrimidin-7-one;

6-(2,6-Dichlorophenyl)-2-(3,4-dimethoxyphenylamino)-8-ethyl-8H-pyrido[2,3-d]pyrimidin-7-one;

6-(2,6-Dichlorophenyl)-8-ethyl-2-(3,4,5-trimethoxyphenylamino)-8H-pyrido[2,3-d]pyrimidin-7-one;

6-(2,6-Dichlorophenyl)-8-methyl-2-(pyridinylamino)-8H-pyrido[2,3-d]pyrimidin-7-one;

6-(2,6-Dichlorophenyl)-2-[4-(2-diethylaminoethoxy)phenylamino]-8-methyl-8H-pyrido[2,3-d]pyrimidin-7-one;

6-(2,6-Dichlorophenyl)-2-(3-hydroxymethylphenylamino)-8-methyl-8H-pyrido[2,3-d]pyrimidin-7-one;

6-(2,6-Dichlorophenyl)-2-(3,5-dimethoxyphenylamino)-8-methyl-8H-pyrido[2,3-d]pyrimidin-7-one;

{4-[6-(2,6-Dichlorophenyl)-8-methyl-7-oxo-7,8-dihydropyrido[2,3-d]pyrimidin-2-ylamino]-phenyl}-acetic acid, methyl ester;

6-(2,6-Dichlorophenyl)-2-(6-methoxypyridinylamino)-8-methyl-8H-pyrido[2,3-d]pyrimidin-7-one;

{4-[6-(2,6-Dichlorophenyl)-8-methyl-7-oxo-7,8-dihydropyrido[2,3-d]pyrimidin-2-ylamino]-phenyl}-acetic acid;

6-(2,6-Dichlorophenyl)-2-(3-hydroxyphenylamino)-8-methyl-8H-pyrido[2,3-d]pyrimidin-7-one;

4-[6-(2,6-Dichlorophenyl)-8-methyl-7-oxo-7,8-dihydropyrido[2,3-d]pyrimidin-2-ylamino]-benzoic acid, ethyl ester;

3-[6-(2,6-Dichlorophenyl)-8-methyl-7-oxo-7,8-dihydropyrido[2,3-d]pyrimidin-2-ylamino]-benzoic acid, ethyl ester;

3-[6-(2,6-Dichlorophenyl)-8-methyl-7-oxo-7,8-dihydropyrido[2,3-d]pyrimidin-2-ylamino]-benzoic acid;

6-(2,6-Dichlorophenyl)-8-ethyl-2-(pyridin-4-ylamino)-8H-pyrido[2,3-d]pyrimidin-7-one;

(6-(2-Bromo-6-chlorophenyl)-8-ethyl-7-imino-7,8-dihydro-pyrido[2,3-d]pyrimidin-8-yl]-phenylamine;

6-(2-Bromo-6-chlorophenyl)-8-ethyl-2-phenylamino-8H-pyrido[2,3-d]pyrimidin-7-one;

(8-Ethyl-7-imino-6-phenyl-7,8-dihydro-pyrido[2,3-d]pyrimidin-2-yl)-2-phenylamine;

8-Ethyl-6-phenyl-2-phenylamino-8H-pyrido[2,3-d]pyrimidin-7-one;

(6-(3,5-Dimethylphenyl)-8-ethyl-7-imino-7,8-dihydropyrido[2,3-d]pyrimidin-2-yl)-2-phenylamine; or 6-(3,5-Dimethylphenyl)-8-ethyl-2-phenylamino-8H-pyrido[2,3-d]pyrimidin-7-one.

\* \* \* \* \*